(12) United States Patent
Wikswo et al.

(10) Patent No.: US 10,532,354 B2
(45) Date of Patent: Jan. 14, 2020

(54) MULTICOMPARTMENT LAYERED AND STACKABLE MICROFLUIDIC BIOREACTORS AND APPLICATIONS OF SAME

(71) Applicant: Vanderbilt University, Nashville, TN (US)

(72) Inventors: John P. Wikswo, Brentwood, TN (US); Dmitry A. Markov, Nashville, TN (US); Ronald S. Reiserer, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 15/776,524

(22) PCT Filed: Nov. 23, 2016

(86) PCT No.: PCT/US2016/063586
§ 371 (c)(1),
(2) Date: May 16, 2018

(87) PCT Pub. No.: WO2017/091718
PCT Pub. Date: Jun. 1, 2017

(65) Prior Publication Data
US 2018/0326417 A1    Nov. 15, 2018

Related U.S. Application Data

(63) Continuation-in-part of application No. 15/191,092, filed on Jun. 23, 2016, now Pat. No. 10,023,832, and
(Continued)

(51) Int. Cl.
*B01L 3/00*      (2006.01)
*B01L 9/00*      (2006.01)
(Continued)

(52) U.S. Cl.
CPC ... *B01L 3/502715* (2013.01); *B01L 3/502707* (2013.01); *B01L 9/00* (2013.01);
(Continued)

(58) Field of Classification Search
CPC ..... B01L 2300/0816; B01L 2300/0874; B01L 2400/0415; B01L 2400/0472;
(Continued)

(56) References Cited

U.S. PATENT DOCUMENTS 6,536,477 B1    3/2003    O'Connor et al.
8,308,452 B2 *  11/2012   Amirouche ........... F04B 43/046
                                                    417/413.2
(Continued)

FOREIGN PATENT DOCUMENTS

WO      2014-081840 A1    5/2014

OTHER PUBLICATIONS

Denney,D and Stevens,JR. Clozapine and Seizures, Biol.Psychiatry, 37, 427-433, 1995.
(Continued)

*Primary Examiner* — Jennifer Wecker
(74) *Attorney, Agent, or Firm* — Locke Lord LLP; Tim Tingkang Xia, Esq.

(57) ABSTRACT

In certain aspects of the invention, a stackable device includes multiple elements stacked sequentially. A chamber is formed in each of the elements or between adjacent two of the elements, and each chamber is in fluid communication with an input channel and an output channel. The chambers are aligned with each other, and adjacent two chambers are separated from each other by a membrane. In certain aspects of the invention, a system includes at least one stackable device, each stackable device having multiple chambers; and at least one of a perfusion controller, a microformulator, and a microclinical analyzer in fluid communication with the
(Continued)

at least one stackable device. In other aspects of the invention, the use of four microformulators, electrodes and an impedance analyzer can measure the impedance spectrum of each barrier in a multi-transwell plate.

10 Claims, 59 Drawing Sheets

Related U.S. Application Data a continuation-in-part of application No. 14/651,174, filed on Jun. 10, 2015, now Pat. No. 9,618,129, and a continuation-in-part of application No. 14/646,300, filed on May 20, 2015, now Pat. No. 9,874,285, and a continuation-in-part of application No. 14/363,074, filed on Jun. 5, 2014, now Pat. No. 10,078,075, and a continuation-in-part of application No. 13/877,925, filed on Jul. 16, 2013, now abandoned.

(60) Provisional application No. 62/259,327, filed on Nov. 24, 2015.

(51) Int. Cl.

| | |
|---|---|
| *C12M 1/00* | (2006.01) |
| *C12M 3/06* | (2006.01) |
| *G01N 33/543* | (2006.01) |
| *G01N 35/08* | (2006.01) |
| *G01N 27/02* | (2006.01) |
| *G01N 27/00* | (2006.01) |

(52) U.S. Cl.
CPC ............ *C12M 23/16* (2013.01); *C12M 23/34* (2013.01); *C12M 29/04* (2013.01); *C12M 29/10* (2013.01); *G01N 27/026* (2013.01); *G01N 33/54366* (2013.01); *G01N 35/08* (2013.01); *B01L 2300/0816* (2013.01); *B01L 2300/0874* (2013.01); *B01L 2400/0415* (2013.01); *B01L 2400/0472* (2013.01); *B01L 2400/0487* (2013.01); *G01N 27/00* (2013.01)

(58) Field of Classification Search
CPC ....... B01L 2400/0487; B01L 3/502707; B01L 3/502715; B01L 9/00; C12M 23/16; C12M 23/34; C12M 29/04; C12M 29/10; G01N 27/00; G01N 33/54366; G01N 35/08

See application file for complete search history.

(56) References Cited

U.S. PATENT DOCUMENTS

| | | | |
|---|---|---|---|
| 2012/0145277 A1 | 6/2012 | Bruneaux et al. | |
| 2012/0288417 A1* | 11/2012 | Bisson ............... | B81C 1/00119 422/240 |
| 2015/0202625 A1 | 7/2015 | Hong et al. | |

OTHER PUBLICATIONS

Jutkiewicz,EM, Baladi,MG, Folk,JE, Rice,KC, Woods,JH. The Convulsive and Electroencephalographic Changes Produced by Nonpeptidic Delta-Opioid Agonists in Rats: Comparison With Pentylenetetrazol, J.Pharmacol.Exp.Ther., 317, 1337-1348, 2006.
Antinori,A, Perno,CF, Giancola,ML, Forbici,F, Ippolito,G, Hoetelmans,RM, Piscitelli,SC. Efficacy of Cerebrospinal Fluid (CSF)-Penetrating Antiretroviral Drugs Against HIV in the Neurological Compartment: Different Patterns of Phenotypic Resistance in CSF and Plasma, Clin.Infect.Dis., 41, 1787-1793, 2005.
Enders,JR, Goodwin,CR, Marasco,CC, Seale,KT, Wikswo,JP, McLean,JA. Advanced Structural Mass Spectrometry for Systems Biology: Pulling the Needles From Haystacks, Spectroscopy Supp. Curr.Trends Mass Spectrometry, Jul. 18-23, 2011.
Enders,JR, Marasco,CC, Wikswo,JP, McLean,JA. A Dual-Column Solid Phase Extraction Strategy for Online Collection and Preparation of Continuously Flowing Effluent Streams for Mass Spectrometry, Anal.Chem., 84, 8467-8474, 2012. PMCID: PMC3518407.
Hines,KM, Ashfaq,S, Davidson,JM, Opalenik,SR, Wikswo,JP, McLean,JA. Biomolecular Signatures of Diabetic Wound Healing by Structural Mass Spectrometry, Anal.Chem., 85, 3651-3659, 2013. PMCID: PMC3622049.
Brown,JA, Sherrod,SD, Goodwin,CR, Brewer,B, Yang,L, Garbett,KA, Li,D, McLean,JA, Wikswo,JP, Mirnics,K. Metabolic Consequences of Interleukin-6 Challenge in Developing Neurons and Astroglia, J.Neuroinflamm., 11, Article 183, 2014. PMCID: PMC4233071.
Goodwin,CR, Sherrod,SD, Marasco,CC, Bachmann,BO, Schramm-Sapyta,N, Wikswo,JP, McLean,JA. Phenotypic Mapping of Metabolic Profiles Using Self-Organizing Maps of High-Dimensional Mass Spectrometry Data, Anal.Chem., 86, 6563-6571, 2014. PMCID: PMC4082383.
Grover,WH, Skelley,AM, Liu,CN, Lagally,ET, Mathies,RA. Monolithic Membrane Valves and Diaphragm Pumps for Practical Large-Scale Integration into Glass Microfluidic Devices, SensorActuat.B-Chem., 89, 315-323, 2003.
Lagally,ET, Scherer,JR, Blazej,RG, Toriello,NM, Diep,BA, Ramchandani,M, Sensabaugh,GF, Riley,LW, Mathies,RA. Integrated Portable Genetic Analysis Microsystem for Pathogen/Infectious Disease Detection, Anal.Chem., 76, 3162-3170, 2004.
Lagally,ET and Mathies,RA. Integrated Genetic Analysis Microsystems, Journal of Physics D-Applied Physics, 37, R245-R261, 2004.
Skelley,AM, Scherer,R, Aubrey,AD, Grover,WH, Ivester,RHC, Ehrenfreund,P, Grunthaner,FJ, Bada,JL, Mathies,RA. Development and Evaluation of a Microdevice for Amino Acid Biomarker Detection and Analysis on Mars, PNAS, 102, 1041-1046, 2005.
Grover,WH, Ivester,RHC, Jensen,EC, Mathies,RA. Development and Multiplexed Control of Latching Pneumatic Valves Using Microfluidic Logical Structures, Lab Chip, 6, 623-631, 2006.
Sip,CG, Bhattacharjee,N, Folch,A. Microfluidic Transwell Inserts for Generation of Tissue Culture-Friendly Gradients in Well Plates, Lab Chip, 14, 302-314, 2014.
Domenech,M, Yu,HM, Warrick,J, Badders,NM, Meyvantsson,I, Alexander,CM, Beebe,DJ. Cellular Observations Enabled by Microculture: Paracrine Signaling and Population Demographics, Integrative Biology, 1, 267-274, 2009.
Prokop,A, Prokop,Z, Schaffer,D, Kozlov,E, Wikswo,JP, Cliffel,D, Baudenbacher,F. NanoLiterBioReactor: Long-Term Mammalian Cell Culture at Nanofabricated Scale, Biomed.Microdevices, 6, 325-339, 2004.
Wikswo,JP Prokop,A, Baudenbacher,F, Cliffel,D, Csukas,B, Velkovsky,M. Engineering Challenges of BioNEMS: the Integration of Microfluidics, and Micro- and Nanodevices, Models, and External Control for Systems Biology, IEE Proc.-Nanobiotechnol., 153, 81-101, 2006.
Darby,S, Moore, M, Wikswo,JP, Reiserer,R, Friedlander,T, Schaffer,DK, Seale,KT. A Metering Rotary Nanopump for Microfluidic Systems, Lab Chip, 10, 3218-3226, 2010. PMCID: PMC4156019.
Eklund,SE, Taylor,D, Kozlov,E, Prokop,A, Cliffel,DE. A Microphysiometer for Simultaneous Measurement of Changes in Extracellular Glucose, Lactate, Oxygen, and Acidification Rate, Anal.Chem., 76, 519-527, 2004.
Eklund,SE, Snider,RM, Wikswo,J, Baudenbacher,F, Prokop,A, Cliffel,DE. Multianalyte Microphysiometry As a Tool in Metabolomics and Systems Biology, J.Electroanal.Chem., 587, 333-339, 2006.
Wilburn, J.P., Ciobanu, M., Cliffel, D.E., Scanning Electrochemical Microscopy of Individual Pancreatic Islets, J. Electrochemical Society, 163 (4) H3077-H3082, 2016.
Eklund,SE, Thompson,RG, Snider,RM, Camey,CK, Wright,DW, Wikswo,J, Cliffel,DE. Metabolic Discrimination of Select List Agents by Monitoring Cellular Responses in a Multianalyte Microphysiometer, Sensors, 9, 2117-2133, 2009. PMCID: PMC3345856.

(56) References Cited

OTHER PUBLICATIONS

Snider,RM, McKenzie,JR, Kraft,L, Kozlov,E, Wikswo,JP, Cliffel,DE. The Effects of Cholera Toxin on Cellular Energy Metabolism, Toxins, 2, 632-648, 2010. PMCID: PMC3153216.

Velkovsky,M, Snider,R, Cliffel,DE, Wikswo,JP. Modeling the Measurements of Cellular Fluxes in Microbioreactor Devices Using Thin Enzyme Electrodes, Journal of Mathematical Chemistry, 49, 251-275, 2011. PMCID: PMC3768171.

Harry,RS, Hiatt,LA, Kimmel,DW, Carney,CK, Halfpenny,KC, Cliffel,DE, Wright,DW. Metabolic Impact of 4-Hydroxynonenal on Macrophage-Like RAW 264.7 Function and Activation, Chem.Res. Toxicol., 25, 1643-1651, 2012. PMCID: PMC3444243.

Hiatt,LA, McKenzie,JR, Deravi,LF, Harry,RS, Wright,DW, Cliffel,DE. A Printed Superoxide Dismutase Coated Electrode for the Study of Macrophage Oxidative Burst, Biosens.Bioelectron., 33, 128-133, 2012. PMCID: PMC3291099.

Kimmel,DW, LeBlanc,G, Meschievitz,ME, Cliffel,DE. Electrochemical Sensors and Biosensors, Anal.Chem., 84, 685-707, 2012.

McKenzie,JR, Palubinsky,AM, Brown,JE, McLaughlin,B, Cliffel,DE. Metabolic Multianalyte Microphysiometry Reveals Extracellular Acidosis Is an Essential Mediator of Neuronal Preconditioning, ACS Chem.Neurosci., 3, 510-518, 2012. PMCID: PMC3399578.

Kimmel,DW, Dole,WP, Cliffel,DE. Application of Multianalyte Microphysiometry to Characterize Macrophage Metabolic Responses to Oxidized LDL and Effects of an ApoA-1 Mimetic, Biochem. Biophys.Res.Commun., 431, 181-185, 2013. PMCID: PMC3576722.

Kimmel,DW, Meschievitz,ME, Hiatt,LA, Cliffel,DE. Multianalyte Microphysiometry of Macrophage Responses to Phorbol Myristate Acetate, Lipopolysaccharide, and Lipoarabinomannan, Electroanalysis, 25, 1706-1712, 2013. PMC21607.

Lima,EA, Snider,RM, Reiserer,RS, McKenzie,JR, Kimmel,DW, Eklund,SE, Wikswo,Jp, Cliffel,De. Multichamber Multipotentiostat System for Cellular Microphysiometry, Sensor.Actuat.B-Chem., 204, 536-543, 2014. PMCID: PMC4167374.

Koomen,JM, Ruotolo,BT, Gillig,KJ, McLean,JA, Russell,DH, Kang,MJ, Dunbar,KR, Fuhrer,K, Gonin,M, Schultz,JA. Oligonucleotide Analysis With MALDI-Ion-Mobility-TOFMS, Anal.Bioanal.Chem., 373, 612-617, 2002.

Mclean,JA, Ruotolo,BT, Gillig,KJ, Russell,DH. Ion Mobility-Mass Spectrometry: a New Paradigm for Proteomics, Int.J.Mass Spectrom., 240, 301-315, 2005.

Mclean,JA, Ridenour,WB, Caprioli,RM. Profiling and Imaging of Tissues by Imaging Ion Mobility-Mass Spectrometry, J. Mass Spectrom., 42, 1099-1105, 2007.

Enders,JR and McLean,JA. Chiral and Structural Analysis of Biomolecules Using Mass Spectrometry and Ion Mobility-Mass Spectrometry, Chirality, 21, E253-E264, 2009.

Fenn,LS and McLean,JA. Simultaneous Glycoproteomics on the Basis of Structure Using Ion Mobility-Mass Spectrometry, Mol. Biosyst., 5, 1298-1302, 2009.

Fenn,LS, Kliman,M, Mahsut,A, Zhao,SR, McLean,JA. Characterizing Ion Mobility-Mass Spectrometry Conformation Space for the Analysis of Complex Biological Samples, Anal.Bioanal.Chem., 394, 235-244, 2009. PMCID: PMC2762638.

Enders,JR, Marasco,CC, Kole,A, Nguyen,B, Sundarapandian,S, Seale,KT, Wikswo,JP, McLean,JA. Towards Monitoring Real-Time Cellular Response Using an Integrated Microfluidics-MALDI/NESI-Ion Mobility-Mass Spectrometry Platform, IET Syst.Biol., 4, 416-427, 2010. PMCID: PMC4254925.

Kliman,M, Vijayakrishnan,N, Wang,L, Tapp,JT, Broadie,K, McLean,JA. Structural Mass Spectrometry Analysis of Lipid Changes in a Drosophila Epilepsy Model Brain, Mol.Biosyst., 6, 958-966, 2010. PMCID: PMC3848785.

McLean,JA, Schultz,JA, Woods,AS. Ion Mobility-Mass Spectrometry for Biological and Structural Mass Spectrometry. In: Electrospray and MALDI mass spectrometry: fundamentals, instrumentation, practicalities, and biological applications, Cole,RB, ed. Wiley, Hoboken, N.J., 411-439, 2010.

Goodwin,CR, Fenn,LS, Derewacz,DK, Bachmann,BO, McLean,JA. Structural Mass Spectrometry: Rapid Methods for Separation and Analysis of Peptide Natural Products, J.Nat.Prod., 75:48-53, 2012.

Fenn,LS and McLean,JA. Structural Separations by Ion Mobility-Mass Spectrometry for Glycomics and Glycoproteomics. In: Mass Spectrometry of Glycoproteins: Methods and Protocols, Kohler,JJ, eds. Humana Press, In press, 2011.

Fenn,LS and McLean,JA. Structural Resolution of Carbohydrate Positional and Structural Isomers Based on Gas-Phase Ion Mobility-Mass Spectrometry, Phys.Chem.Chem.Phys., 13, 2196-2205, 2011.

Kliman,M, May,JC, McLean,JA. Lipid Analysis and Lipidomics by Structurally Selective Ion Mobility-Mass Spectrometry, Biochimica Et Biophysica Acta (BBA)—Molecular and Cell Biology of Lipids, 1811, 935-945, 2011. PMCID: PMC3326421.

May,JC, Goodwin,CR, McLean,JA. Gas-Phase Ion Mobility-Mass Spectrometry(IM-MS)and Tandem IM-MS/MS Strategies for Metabolism Studies and Metabolomics. In: Encyclopedia of drug metabolism and interactions, Lyubimov, AV, ed. Wiley, Hoboken, N.J., 257-285, 2012.

Matusch,A, Fenn,LS, Depboylu,C, Klietz,M, Strohmer,S, McLean,JA, Becker,JS. Combined Elemental and Biomolecular Mass Spectrometry Imaging (MSI) for Probing the Inventory of Tissue at the Micrometer Scale, Anal. Chem., 84, 3170-3178, 2012.

Fenn,LS and McLean,JA. Structural Separations by Ion Mobility-MS for Glycomics and Glycoproteomics. In: Mass spectrometry of glycoproteins: methods and protocols, Kohler,J, eds. Humana Press, New York, 171-193, 2013.

Shi,M, Majumdar,D, Gao,Y, Brewer,BM, Goodwin,CR, McLean,JA, Li,D, Webb,DJ. Glia Co-Culture With Neurons in Microfluidic Platforms Promotes the Formation and Stabilization of Synaptic Contacts, Lab Chip, 13, 3008-3021, 2013. PMCID: PMC3712871.

Xu,L, Kliman,M, Forsythe,JG, Korade,Z, Hmelo,AB, Porter,NA, McLean,JA, Profiling and Imaging Ion Mobility-Mass Spectrometry Analysis of Cholesterol and 7-Dehydrocholesterol in Cells Via Sputtered Silver MALDI, J. Am. Soc. Mas Spectrom., 26:924-933, 2015.

May,JC and McLean,JA. Ion Mobility-Mass Spectrometry: Time-Dispersive Instrumentation, Anal.Chem., 87, 1422-1436, 2015.

May,JC, Goodwin,CR, McLean,JA. Ion Mobility-Mass Spectrometry Strategies for Untargeted Systems, Synthetic, and Chemical Biology, Curr.Opin.Biotechnol., 31, 117-121, 2015.

Goodwin,CR, Covington,BC, Derewacz,D, K, McNees,CR, Wikswo,JP, McLean,JA, Bachmann,BO. Structuring Microbial Metabolic Responses to Multiplexed Stimuli Via Self-Organizing Metabolomics Maps, Chem.Biol., In press, DOI:10.1016/j.chembiol.2015.03.020, 2015.

Daneman,R and Prat,A. The Blood-Brain Barrier, Cold Spring Harb.Perspect.Biol., 7, Article a020412, 2015.

Rubin,LL, Hall,DE, Porter,S, Barbu,K, Cannon,C, Horner,HC, Janatpour,M, Liaw,CW, Manning,K, Morales,J, Tanner, LI, Tomaselli,KJ, Bard,F. A Cell-Culture Model of the Blood-Brain-Barrier, J.Cell Biol., 115, 1725-1735, 1991.

Abbott,NJ, Hughes,CCW, Revest,PA, Greenwood,J. Development and Characterization of a Rat-Brain Capillary Endothelial Culture—Towards an Invitro Blood-Brain-Barrier, J.Cell Sci., 103, 23-37, 1992.

Vajandar,SK, Xu,DY, Markov,DA, Wikswo,JP, Hofmeister,W, Li,DY. SiO2-Coated Porous Anodic Alumina Membranes for High Flow Rate Electroosmotic Pumping, Nanotechnology, 18, 275705, 2007.

Vajandar,SK, Xu,DY, Sun,JS, Markov,DA, Hofmeister,WH, Li,DY. Field-Effect Control of Electroosmotic Pumping Using Porous Silicon-Silicon Nitride Membranes, J.Microelectromech.S., 18, 1173-1183, 2009.

Prabhakarpandian,B, Shen,MC, Nichols,JB, Mills,IR, Sidoryk-Wegrzynowicz,M, Aschner,M, Pant,K. SyM-BBB: A Microfluidic Blood Brain Barrier Model, Lab Chip, 13, 1093-1101, 2013.

Berdondini,L, Imfeld,K, Maccione,A, Tedesco,M, Neukom,S, Koudelka-Hep,M, Martinoia,S. Active Pixel Sensor Array for High Spatio-Temporal Resolution Electrophysiological Recordings From Single Cell to Large Scale Neuronal Networks, Lab Chip, 9, 2644-2651, 2009.

(56) References Cited

OTHER PUBLICATIONS

Imfeld,K, Maccione,A, Gandolfo,M, Martinoia,S, Farine,PA, Koudelka-Hep,M, Berdondini,L. Real-Time Signal Processing for High-Density Microelectrode Array Systems, Int.J.Adapt.Control Signal Process., 23, 983-998, 2009.

Shi,YC, Kirwan,P, Livesey,FJ. Directed Differentiation of Human Pluripotent Stem Cells to Cerebral Cortex Neurons and Neural Networks, Nat.Protoc., 7, 1836-1846, 2012.

Shi,YC, Kirwan,P, Smith,J, Robinson,HPC, Livesey,FJ. Human Cerebral Cortex Development From Pluripotent Stem Cells to Functional Excitatory Synapses, Nat.Neurosci., 15, 477-486, 2012.

Cucullo,L, McAllister,MS, Kight,K, Krizanac-Bengez,L, Marroni,M, Mayberg,MR, Stanness,KA, Janigro,D. A New Dynamic in Vitro Model for the Multidimensional Study of Astrocyte-Endothelial Cell Interactions at the Blood-Brain Barrier, Brain Res., 951, 243-254, 2002.

Cucullo,L, Hossain,M, Tiemey,W, Janigro,D. A New Dynamic in Vitro Modular Capillaries-Venules Modular System: Cerebrovascular Physiology in a Box, BMC Neurosci., 14, Article 18, 2013. PMCID: PMC3598202.

Griep,LM, Wolbers,F, de Wagenaar,B, ter Braak,PM, Weksler,BB, Romero,IA, Couraud,PO, Vermes,l, van der Meer, AD, van den Berg,A. BBB on CHIP: Microfluidic Platform to Mechanically and Biochemically Modulate Blood-Brain Barrier Function, Biomed. Microdevices, 15, 145-150, 2013.

Alendor,DJ, Block,FE, Cliffel,DE, Daniels,JS, Ellacoll,KLJ, Goodwin,CR, Hofmeister,LJ, Li,D, Markov,DA, May,JC, McCawley, LJ, McLaughlin,B, McLean,JA, Niswender,KD, Pensabene,V, SealeKT, Sherrod,SD, Sung,H, Tabb,DL, Webb,DJ, Wikswo,JP. Neurovascular Unit on a Chip: Implications for Translational Applications, Stem Cell Res. Ther., 4(Suppl 1), Article S18, 2013. PMCID: PMC4029462.

Wikswo,JP, Block III,FE, Cliffel,DE, Goodwin,CR, Marasco,CC, Markov,DA, McLean,DL, McLean,JA, McKenzie,JR, Reiserer,RS, Samson,PC, Schaffer,DK, Seale,KT, Sherrod,SD. Engineering Challenges for Instrumenting and Controlling Integrated Organ-on-Chip Systems, IEEE Trans.Biomed.Eng., 60, 682-690, 2013. PMCID: PMC3696887.

Mitaka,T, Sato,F, Mizuguchi,T, Yokono,T, Mochizuki,Y. Reconstruction of Hepatic Organoid by Rat Small Hepatocytes and Hepatic Nonparenchymal Cells, Hepatology, 29, 111-125, 1999.

Kusumi,T, Ishihara,K, Mizumoto,H, Nakazawa,K, Ijima,H, Funatsu,K, Kajiwara,T. Evaluation of a Bioreactor With Stacked Sheet Shaped Organoids of Primary Hepatocytes, J.Bio.Sci.Bioeng., 107, 552-555, 2009.

Sonntag,F, Schilling,N, Mader,K, Gruchow,M, Klotzbach,U, Lindner,G, Horland,R, Wagner,l, Lauster,R, Howitz,S, Hoffmann,S, Marx,U. Design and Prototyping of a Chip-Based Multi-Micro-Organoid Culture System for Substance Testing, Predictive to Human (Substance) Exposure, J.Biotechnol., 148, 70-75, 2010.

Lancaster,MA, Renner,M, Martin,CA, Wenzel,D, Bicknell,LS, Hurles,ME, Homfray,T, Penninger,JM, Jackson,AP, Knoblich,JA. Cerebral Organoids Model Human Brain Development and Microcephaly, Nature, 501, 373-379, 2013.

Watson,CL, Mahe,MM, Munera,J, Howell,JC, Sundaram,N, Poling,HMM, Schweitzer,JI, Vallance,JE, Mayhew,CN, Sun, Y, Grabowski,G, Finkbeiner,SR, Spence,JR, Shroyer,NF, Wells,JM, Helmrath,MA. An in Vivo Model of Human Small Intestine Using Pluripotent Stem Cells, Nat.Med., 20, 1310-1314, 2014.

Beebe,DJ, Ingber,DE, den Toonder,J. Organs on Chips 2013, Lab Chip, 13, 3447-3448, 2013.

Huh,D, Torisawa,YS, Hamilton,GA, Kim,HJ, Ingber,DR. Microengineered Physiological Biomimicry: Organs-on-Chips, Lab Chip, 12, 2156-2164, 2012.

Kim,HJ, Huh,D, Hamilton, G, Ingber,DE. Human Gut-on-a-Chip Inhabited by Microbial Flora That Experiences Intestinal Peristalsis-Like Motions and Flow, Lab Chip, 12, 2165-2174, 2012.

Huh,D, Matthews,BD, Mammoto,A, Montoya-Zavala,M, Hsin,HY, Ingber,DE. Reconstituting Organ-Level Lung Functions on a Chip, Science, 328, 1662-1668, 2010.

van der Meer,AD and van den Berg,A. Organs-on-Chips: Breaking the in Vitro Impasse, Integr.Biol., 4, 461-470, 2012.

Moraes,C, Mehta,G, Lesher-Perez,SC, Takayama,S. Organs-on-a-Chip: A Focus on Compartmentalized Microdevices, Ann.Biomed. Eng., 40, 1211-1227, 2012.

Wikswo,JP and Porter,AP. Biology Coming Full Circle: Joining the Whole and the Parts, Exp.Biol.Med., 240, 3-7, 2015. PMC4391629.

Wikswo,JP. The Relevance and Potential Roles of Microphysiological Systems in Biology and Medicine, Exp.Biol.Med., 239, 1061-1072, 2014. PMC4330974.

Wikswo,J, Curtis,EL, Eagleton,ZE, Evans,BC, Kole,A, Hofmeister,LH, Matloff,WJ. Scaling and Systems Biology for Integrating Multiple Organs-on-a-Chip, Lab Chip, 13, 3496-3511, 2013. PMCID: PMC3818688.

Achyuta,AKH, Conway,AJ, Crouse,RB, Bannister,EE, Lee,RN, Katnik,CP, Behensky,AA, Cuevas,J, Sundaram,SS. A Modular Approach to Create a Neurovascular Unit-on-a-Chip, Lab Chip, 13, 542-553, 2013.

Aboud,AA, Tidball,AM, Kumar,KK, Neely,MD, ESS,KC, Erikson,KM, Bowman,AB. Genetic Risk for Parkinson's Disease Correlates With Alterations in Neuronal Manganese Sensitivity Between Two Human Subjects, Neurotoxicology, 33, 1443-1449, 2012. PMCID: PMC3518601.

Aboud,AA, Tidball,AM, Kumar,KK, Neely,MD, Han,BY, Ess,KC, Hong,CC, Erikson,KM, Hedera,P, Bowman,AB. PARK2 Patient Neuroprogenitors Show Increased Mitochondrial Sensitivity to Copper, Neurobiol.Dis., 73, 204-212, 2015. PMCID: PMC4394022.

Kumar,KK, Lowe,EW, Aboud,AA, Neely,MD, Redha,R, Bauer,JA, Odak,M, Weaver,CD, Meiler,J, Aschner,M, Bowman, AB. Cellular Manganese Content Is Developmentally Regulated in Human Dopaminergic Neurons, Sci.Rep., 4, Article 6801, 2014. PMCID: PMC4210885.

Neely,MD, Litt,NJ, Tidball,AM, Li,GG, Aboud,AA, Hopkins,CR, Chamberlin,R, Hong,CC, Ess,KC, Bowman,AB. DMH1, a Highly Selective Small Molecule BMP Inhibitor Promotes Neurogenesis of HiPSCs: Comparison of PAX6 and SOX1 Expression During Neural Induction, ACS Chem.Neurosci., 3, 482-491, 2012. PMCID: PMC3400384.

Tidball,AM, Bryan,MR, Uhouse,MA, Kumar,KK, Aboud,AA, Feist,JE, Ess,KC, Neely,MD, Aschner,M, Bowman,AB. A Novel Manganese-Dependent ATM-P53 Signaling Pathway Is Selectively Impaired in Patient-Based Neuroprogenitor and Murine Striatal Models of Huntington's Disease, Hum.Mol.Genet., 24, 1929-1944, 2015. PMCID: PMC4355025.

Chambers,SM, Fasano,CA, Papapetrou,EP, Tomishima,M, Sadelain,M, Studer,L. Highly Efficient Neural Conversion of Human ES and IPS Cells by Dual Inhibition of SMAD Signaling, Nat.Biotechnol., 27, 275-280, 2009.

Neely,MD, Tidball,AM, Aboud,AA, Ess,KC, Bowman,AB. Induced Pluripotent Stem Cells (IPSCs): An Emerging Model System for the Study of Human Neurotoxicology. In: Cell culture techniques, Aschner,M, eds. Humana Press, New York, 27-61, 2011.

Molyneaux,BJJ, Arlotta,P, Menezes,JRL, Macklis,JD. Neuronal Subtype Specification in the Cerebral Cortex, Nat.Rev. Neurosci., 8, 427-437, 2007.

Bedogni,F, Hodge,RD, Elsen,GE, Nelson,BR, Daza,RAM, Beyer,RP, Bammler,TK, Rubenstein,JLR, Hevner,RF. Tbr1 Regulates Regional and Laminar Identity of Postmitotic Neurons in Developing Neocortex, PNAS (US), 107, 13129-13134, 2010.

Leone,DP, Srinivasan,K, Chen,B, Alcamo,E, McConnell,SK. The Determination of Projection Neuron Identity in the Developing Cerebral Cortex, Curr.Opin.Neurobiol., 18, 28-35, 2008.

Simi,A, Amin,H, Maccione,A, Nieus,T, Berdondini,L. Integration of Microstructured Scaffolds, Neurons, and Multielectrode Arrays. In: Brain Extracellular Matrix in Health and Disease, Dityatev,A, eds. Elsevier, Amsterdam, Netherlands, 415-442, 2014.

Berdondini,L, Bosca,A, Nieus,T, Maccione,A. Active Pixel Sensor Multielectrode Array for High Spatiotemporal Resolution. In: Nanotechnology and Neuroscience: Nano-electronic, Photonic and Mechanical Neuronal Interfacing, De Vittorio,M, eds. Springer, New York, 207-238, 2014.

Maccione,A, Garofalo,M, Nieus,T, Tedesco,M, Berdondini,L, Martinoia,S. Multiscale Functional Connectivity Estimation on Low-

(56) References Cited

OTHER PUBLICATIONS

Density Neuronal Cultures Recorded by High-Density CMOS Micro Electrode Arrays, J.Neurosci.Methods, 207, 161-171, 2012.
Ullo,S, Nieus,TR, Sona,D, Maccione,A, Berdondini,L, Murino,V. Functional Connectivity Estimation Over Large Networks at Cellular Resolution Based on Electrophysiological Recordings and Structural Prior, Front.Neuroanatomy, 8, Article 137, 2014.
Mata,A, Fleischman,AJ, Roy,S. Characterization of Polydimethylsiloxane (PDMS) Properties for Biomedical Micro/Nanosystems, Biomed.Microdevices, 7, 281-293, 2005.
Zhou JW, Ellis,AV, Voelcker,NH. Recent Developments in PDMS Surface Modification for Microfluidic Devices, Electrophoresis, 31, 2-16, 2010.
van Poll,ML, Zhou,F, Ramstedt,M, Hu,L, Huck,WTS. A Self-Assembly Approach to Chemical Micropatterning of Poly (Dimethylsiloxane), Angew.Chem., 119, 6754-6757, 2007.
Wong,I and Ho,CM. Surface Molecular Property Modifications for Poly(Dimethylsiloxane) (PDMS) Based Microfluidic Devices, Microfluid.Nanofluid., 7, 291-306, 2009.
Toepke,MW and Beebe,DJ. PDMS Absorption of Small Molecules and Consequences in Microfluidic Applications, Lab Chip, 6, 1484-1486, 2006.
Robinson,T, Schaerli,Y, Wootton,R, Hollfelder,F, Dunsby,C, Baldwin,G, Neil,M, French,P, Demello,A. Removal of Background Signals From Fluorescence Thermometry Measurements in PDMS Microchannels Using Fluorescence Lifetime Imaging, Lab Chip, 9, 3437-3441, 2009.
Wang,JD, Douville,NJ, Takayama,S, ElSayed,M. Quantitative Analysis of Molecular Absorption into PDMS Microfluidic Channels, Ann.Biomed.Eng., 40, 1862-1873, 2012.
Gorecki,T, Yu,XM, Pawliszyn,J. Theory of Analyte Extraction by Selected Porous Polymer SPME Fibres, Analyst, 124, 643-649, 1999.
Wang,Y, Lin,WY, Liu,K, Lin,RJ, Selke,M, Kolb,HC, Zhang,N, Zhao,XZ, Phelps,ME, Shen,CK, Faull,KF, Tseng,HR. An Integrated Microfluidic Device for Large-Scale in Situ Click Chemistry Screening, Lab Chip, 9, 2281-2285, 2009.
Berthier,E, Young,EWK, Beebe,D. Engineers Are From PDMS-Land, Biologists Are From Polystyrenia, Lab Chip, 12, 1224-1237, 2012.
Peterson,SL, McDonald,A, Gourley,PL, Sasaki,DY. Poly(Dimethylsiloxane) Thin Films As Biocompatible Coatings for Microfluidic Devices: Cell Culture and Flow Studies With Glial Cells, J.Biomed.Mater.Res.A, 72A, 10-18, 2005.
Vickers,JA, Caulum,MM, Henry,CS. Generation of Hydrophilic Poly(Dimethylsiloxane) for High-Performance Microchip Electrophoresis, Anal.Chem., 78, 7446-7452, 2006.
Markov,DA, Lillie,EM, Garbett,SP, McCawley,LJ. Variation in Diffusion of Gases Through PDMS Due to Plasma Surface Treatment and Storage Conditions, Biomed.Microdevices, 16, 91-96, 2014. PCMID: PMC3945670.
Ren,XQ, Bachman,M, Sims,C, Li,GP, Allbriton,N. Electroosmotic Properties of Microfluidic Channels Composed of Poly(Dimethylsiloxane), J.Chromatogr.B, 762, 117-125, 2001.
Tan,HML, Fukuda,H, Akagi,T, Ichiki,T. Surface Modification of Poly(Dimethylsiloxane) for Controlling Biological Cells' Adhesion Using a Scanning Radical Microjet, Thin Solid Films, 515, 5172-5178, 2007.
Makamba,H, Kim,JH, Lim,K, Park,N, Hahn,JH. Surface Modification of Poly(Dimethylsiloxane) Microchannels, Electrophoresis, 24, 3607-3619, 2003.
Barbier,V, Tatoulian,M, Li,H, Arefl-Khonsari,F, Ajdari,A, Tabeling,P. Stable Modification of PDMS Surface Properties by Plasma Polymerization: Application to the Formation of Double Emulsions in Microfluidic Systems, Langmuir, 22, 5230-5232, 2006.
Martin,IT, Dressen,B, Boggs,M, Liu,Y, Henry,CS, Fisher,ER. Plasma Modification of PDMS Microfluidic Devices for Control of Electroosmotic Flow, Plasma Processes and Polymers, 4, 414-424, 2007.

Berdichevsky,Y, Khandurina,J, Guttman,A, Lo,YH. UV/Ozone Modification of Poly(Dimethylsiloxane) Microfluidic Channels, Sensor. Actuat.B-Chem., 97, 402-408, 2004.
Efimenko,K Wallace,WE, Genzer,J. Surface Modification of Sylgard-184 Poly(Dimethyl Siloxane) Networks by Ultraviolet and Ultraviolet/Ozone Treatment, J.Colloid Interface Sci., 254, 306-315, 2002.
Bhushan,B, Hansford,D, Lee,KK. Surface Modification of Silicon and Polydimethylsiloxane Surfaces With Vapor-Phase-Deposited Ultrathin Fluorosilane Films for Biomedical Nanodevices, J.Vac. Sci.& Tech.A, 24, 1197-1202, 2006.
Chen,HY, Elkasabi,Y, Lahann,J. Surface Modification of Confined Microgeometries Via Vapor-Deposited Polymer Coatings, J.Am. Chem.Soc., 128, 374-380, 2006.
Chen,HY, McClelland,AA, Chen,Z, Lahann,J. Solventless Adhesive Bonding Using Reactive Polymer Coatings, Anal. Chem., 80, 4119-4124, 2008.
Makamba,H, Hsieh,YY, Sung,WC, Chen,SH. Stable Permanently Hydrophilic Protein-Resistant Thin-Film Coatings on Poly(Dimethylsiloxane) Substrates by Electrostatic Self-Assembly and Chemical Cross-Linking, Anal.Chem., 77, 3971-3978, 2005.
Mehta,G, Kiel,MJ, Lee,JW, Kotov,N, Linderman,JJ, Takayama,S. Polyelectrolyte-Clay-Protein Layer Films on Microfluidic PDMS Bioreactor Surfaces for Primary Murine Bone Marrow Culture, Adv.Funct.Mater., 17, 2701-2709, 2007.
Wang,AJ, Xu,JJ, Zhang,Q, Chen,HY. The Use of Poly(Dimethylsiloxane) Surface Modification With Gold Nanoparticles for the Microchip Electrophoresis, Talanta, 69, 210-215, 2006.
Qiu,JD, Hu,PF, Liang,RP. Separation and Simultaneous Determination of Uric Acid and Ascorbic Acid on a Dynamically Modified Poly(Dimethylsiloxane) Microchip, Anal.Sci., 23, 1409-1414, 2007.
Wang,AJ, Xu,JJ, Chen,HY. Enhanced Microchip Electrophoresis of Neurotransmitters on Glucose Oxidase Modified Poly(Dimethylsiloxane) Microfluidic Devices, Electroanalysis, 19, 674-680, 2007.
Wang,W, Zhao,L, Zhou,F, Zhu,JJ, Zhang,JR. Electroosmotic Flow-Switchable Poly (Dimethylsiloxane) Microfluidic Channel Modified With Cysteine Based on Gold Nanoparticles, Talanta, 73, 534-539, 2007.
Wang,AJ, Xu,JJ, Chen,HY. Proteins Modification of Poly(Dimethylsiloxane) Microfluidic Channels for the Enhanced Microchip Electrophoresis, J.Chromatogr.A, 1107, 257-264, 2006.
Wang,AJ, Xu,JJ, Chen,HY. In-Situ Grafting Hydrophilic Polymer on Chitosan Modified Poly (Dimethylsiloxane) Microchip for Separation of Biomolecules, J.Chromatogr.A, 1147, 120-126, 2007.
Liang,RP, Gan,GH, Qiu,JD. Surface Modification of Poly(Dimethylsiloxane) Microfluidic Devices and Its Application in Simultaneous Analysis of Uric Acid and Ascorbic Acid in Human Urine, Journal of Separation Science, 31, 2860-2867, 2008.
Lee,JN, Park,C, Whitesides,GM. Solvent Compatibility of Poly(Dimethylsiloxane)-Based Microfluidic Devices, Anal. Chem., 75, 6544-6554, 2003.
Gomez-Sjoberg,R, Leyrat,AA, Houseman,BT, Shokat,K, Quake,SR. Biocompatibility and Reduced Drug Absorption of Sol-Gel-Treated Poly(Dimethyl Siloxane) for Microfluidic Cell Culture Applications, Anal.Chern., 82, 8954-8960, 2010.
Yao,MJ and Fang,J. Hydrophilic PEO-PDMS for Microfluidic Applications, J.Micromech.Microeng., 22, Article 025012, 2012.
Ulman,KL, Gomowicz,GA, Larson,KR, Lee,CL. Drug Permeability of Modified Silicone Polymers .1. Silicone Organic Block Copolymers, Journal of Controlled Release, 10, 251-260, 1989.
Ulman,KL, Larson,KR, Lee,CL, Tojo,K. Drug Permeability of Modified Silicone Polymers .2. Silicone Organic Graft-Copolymers, Journal of Controlled Release, 10, 261-272, 1989.
Chawla,K, Lee,S, Lee,BP, Dalsin,JL, Messersmith,PB, Spencer,ND. A Novel Low-Friction Surface for Biomedical Applications: Modification of Poly(Dimethylsiloxane) (PDMS) With Polyethylene Glycol (PEG)-DOPA-Lysine, J.Biomed. Mater.Res.A, 90A, 742-749, 2009.
Viefhues,M, Manchanda,S, Chao,TC, Anselmetti,D, Regtmeier,J, Ros,A. Physisorbed Surface Coatings for Poly (Dimethylsiloxane) and Quartz Microfluidic Devices, Anal.Bioanal.Chem., 401, 2113-2122, 2011.

(56) References Cited

OTHER PUBLICATIONS

Hemmila,S, Cauich-Rodriguez,JV, Kreutzer,J, Kallio,P. Rapid, Simple, and Cost-Effective Treatments to Achieve Long-Term Hydrophilic PDMS Surfaces, Appl.Surf.Sci., 258, 9864-9875, 2012.

Ren,KN, Zhao,YH, Su,J, Ryan,D, Wu,HK. Convenient Method for Modifying Poly(Dimethylsiloxane) To Be Airtight and Resistive Against Absorption of Small Molecules, Anal.Chem., 82, 5965-5971, 2010.

Sasaki,H, Onoe,H, Osaki,T, Kawano,R, Takeuchi,S. Parylene-Coating in PDMS Microfluidic Channels Prevents the Absorption of Fluorescent Dyes, Sensor.Actuat.B-Chem., 150, 478-482, 2010.

Tropmann,A, Tanguy,L, Koltay,P, Zengerle,R, Riegger,L. Completely Superhydrophobic PDMS Surfaces for Microfluidics, Langmuir, 28, 8292-8295, 2012.

Markov,DA, Lu,JQ, Samson,PC, Wikswo,JP, McCawley,LJ. Thick-Tissue Bioreactor As a Platform for Long-Term Organotypic Culture and Drug Delivery, Lab Chip, 12, 4560-4568, 2012. PMCID: PMC3826880.

Dhurjati,R, Liu, X, Gay,CV, Mastro,AM, Vogler,EA. Extended-Term Culture of Bone Cells in a Compartmentalized Bioreactor, Tissue Eng., 12, 3045-3054, 2006.

Kawada,J, Kimura,H, Akutsu,H, Sakai,Y, Fujii,T. Spatiotemporally Controlled Delivery of Soluble Factors for Stem Cell Differentiation, Lab Chip, 12, 4508-4515, 2012.

De Bartolo,L, Salerno,S, Morelli,S, Giomo,L, Rende,M, Memoli,B, Procino,A, Andreucci,VE, Bader,A, Drioli,E. Long-Term Maintenance of Human Hepatocytes in Oxygen-Permeable Membrane Bioreactor, Biomaterials, 27, 4794-4803, 2006.

Pai,JH, Wang ,Y, Salazar,GT, Sims,CE, Bachman,M, Li,GP, Allbritton,NL. Photoresist With Low Fluorescence for Bioanalytical Applications, Anal.Chem., 79, 8774-8780, 2007.

McPherson,AL and Walker,GM. A Photo-Defined Membrane for Precisely Patterned Cellular and Microparticle Arrays, AIP Advances, 2, Article 012153, 2012.

Ornoff,DM, Wang,Y, Allbritton,NL. Characterization of Freestanding Photoresist Films for Biological and MEMS Applications, J.Micromech.Microeng., 23, Article 025009, 2013.

Shah,PK, Hughes,MR, Wang,Y, Sims,CC, Allbritton,NL. Scalable Synthesis of a Biocompatible, Transparent and Superparamagnetic Photoresist for Microdevice Fabrication, J.Micromech.Microeng., 23, Article 107002, 2013.

Wang,Y, Ahmad,AA, Shah,PK, Sims,CE, Magness,ST, Allbritton,NL. Capture and 3D Culture of Colonic Crypts and Colonoids in a Microarray Platform, Lab Chip, 13, 4625-4634, 2013.

Kim,MY, Li,DJ, Pham,LK, Wong,BG, Hui,EE. Microfabrication of High-Resolution Porous Membranes for Cell Culture, J.Membr.Sci., 452, 460-469, 2014.

georgescu,W, Jourquin,J, Estrada,L, Anderson,ARA, Quaranta,V, Wikswo,JP. Model-Controlled Hydrodynamic Focusing to Generate Multiple Overlapping Gradients of Surface-Immobilized Proteins in Microfluidic Devices, Lab Chip, 8, 238-244, 2008. PMC4357342.

Liu,Y, Markov,D, Wikswo,J, McCawley,L. Microfabricated Scaffold-Guided Endothelial Morphogenesis in Three-Dimensional Culture, Biomed.Microdevices, 13, 837-846, 2011.

Walker,GM, Sai,J, Richmond,A, Stremler,MA, Chung,CY, Wikswo,JP. Effects of Flow and Diffusion on Chemotaxis Studies in a Microfabricated Gradient Generator, Lab Chip, 5, 611-618, 2005. PMCID: PMC2665276.

Marasco,CC, Enders,JR, Seale,KT, McLean,JA, Wikswo,JP. Real-Time Cellular Exometabolome Analysis With a Microfluidic-Mass Spectrometry Platform, PloS.One., 10, Article e0117685, 2013. PMC4344306.

Korean Intellectual Property Office (ISR/KR), "International Search Report for PCT/US2016/063586", Korea, dated Mar. 13, 2017.

Wong,AD, Ye,M, Levy,AF, Rothstein,JD, Bergles,DE, Searson,PC. The Blood-Brain Barrier: an Engineering Perspective, Front Neuroeng., 6, Article 7, 2013. PMCID: PMC3757302.

Bardy,C, van den Hurk,M, Eames,T, Marchand,C, Hemandez,RV, Kellogg,M, Gorris,M, Galet,B, Palomares,V, Brown, J, Bang,AG, Mertens,J, Bohnke,L, Boyer,L, Simon,S, Gage,FH. Neuronal Medium That Supports Basic Synaptic Functions and Activity of Human Neurons in Vitro, PNAS, DOI: 10.1073/pnas.1504393112, 2015.

Kiiski,H, Aanismaa,R, Tenhunen,J, Hagman,S, Yla-Outinen,L, Aho,A, Yli-Hankala,A, Bendel,S, Skottman,H, Narkilahti,S. Healthy Human CSF Promotes Glial Differentiation of HESC-Derived Neural Cells While Retaining Spontaneous Activity in Existing Neuronal Networks, Biol.Open, 2, 605-612, 2013.

Mathur,BN, Neely,MD, Dyllick-Brenzinger,M, Tandon,A, Deutch,AY. Systemic Administration of a Proteasome Inhibitor Does Not Cause Nigrostriatal Dopamine Degeneration, Brain Res., 1168, 83-89, 2007. PMCID: PMC2040265.

Faley,S, Seale,K, Hughey,J, Schaffer,DK, VanCompemolle,S, McKinney,B, Baudenbacher,F, Unutmaz,D, Wikswo,JP. Microfluidic Platform for Real-Time Signaling Analysis of Multiple Single T Cells in Parallel, Lab Chip, 8, 1700-1712, 2008. PMCID: PMC4160168.

Faley,SL, Copland,M, Wlodkowic,D, Kolch,W, Seale,KT, Wikswo,JP, Cooper,JM. Microfluidic Single Cell Arrays to Interrogate Signalling Dynamics of Individual, Patient-Derived Hematopoietic Stem Cells, Lab Chip, 9, 2659-2664, 2009.

Markov,DA, Lillie,EM, Samson,PC, Wikswo,JP, McCawley,LJ. A Method for Periodic Sterile Sample Collection During Continuous Cell Culture in Microfluidic Devices, Chips and Tips Online, RSC Publishing, 2010.

Markov,DA, Samson,PC, Schaffer,DK, Dhummakup,A, Wikswo,JP, Shor,LM. Window on a Microworld: Simple Microfluidic Systems for Studying Microbial Transport in Porous Media, J.Vis.Exp., 39, 2010.

Markov,DA, Manuel,S, Shor,L, Opalenik,SR, Wikswo,JP, Samson,PC. Tape Underlayment Rotary-Node (TURN) Valves for Simple on-Chip Microfluidic Flow Control, Biomed.Microdevices, 12, 135-144, 2010. PMCID: PMC3742084.

Seale,KT, Faley,SL, Chamberlain,J, Wikswo,JP, Jr. Macro to Nano: A Simple Method for Transporting Cultured Cells From Milliliter Scale to Nanoliter Scale, Exp.Biol.Med., 235, 777-783, 2010. PMCID: PMC4109816.

Byrd,TF, Hoang,LT, Kim,EG, Pfister,ME, Werner,EM, Arndt,SE, Chamberlain,JW, Hughey,JJ, Nguyen,BA, Schneibel, EJ, Wertz,LL, Whitfield,JS, Wikswo,JP, Seale,KT. The Microfluidic Multitrap Nanophysiometer for Hematologic Cancer Cell Characterization Reveals Temporal Sensitivity of the Calcein-AM Efflux Assay, Sci.Rep., 4, Article 5117, 2014. PMCID: PMC4038811.

Hockemeyer,K, Janetopoulos,C, Terekhov,A, Hofmeister,W, Vilgelm,A, Wikswo,JP, Richmond,A. Engineered Three-Dimensional Microfluidic Device for Interrogating Cell-Cell Interactions in the Tumor Microenvironment, Biomicrofluidics, 8, 044105, 2014. PMCID: PMC4189212.

Yan,Y, Jiang,L, Aufderheide,KJ, Wright,GA, Terekhov,A, Costa,L, Qin,K, McCleery,WT, Fellenstein,JJ, Ustione,A, Robertson,JB, Johnson,CH, Piston,DW, Hutson,MS, Wikswo,JP, Hofmeister,W, Janetopoulos,C. A Microfluidic-Enabled Mechanical Microcompressor for the Immobilization of Live Single- and Multi-Cellular Specimens, Microsc. Microanal., 20, 141-151, 2014. PMCID: PMC4026272.

Ashby,WJ and Zijlstra,A. Established and Novel Methods of Interrogating Two-Dimensional Cell Migration, Integr.Biol. 4, 1338-1350, 2012.

Ashbt,W, Wikswo,JP, Zijlstra,A. Magnetically Attachable Stencils and the Non-Destructive Analysis of the Contribution Made by the Underlying Matrix to Cell Migration, Biomaterials, 33, 8189-8203, 2012. PMCID: PMC3444626.

Georgescu,W, Wikswo,JP, Quaranta,V. Cell Animation: An Open Source MAtLAB Framework for Microscopy Assays, Bioinformatics, 28, 138-139, 2012. PMCID: PMC3244774.

Seale,KT, Reiserer,RS, Markov,DA, Ges,IA, Wright,C, Janetopoulos,C, Wikswo,JP. Mirrored Pyramidal Wells for Simultaneous Mutiple Vantage Point Microscopy, J.Microsc., 232, Pt.1, 1-6, 2008. PMCID: PMC3789065.

Seale,K, Janetopoulos,C, Wikswo,J. Micro-Mirrors for Nanoscale Three-Dimensional Microscopy, Acs Nano, 3, 493-497, 2009.

Schmidt,MD, Vallabhajosyula,RR, Jenkins,JW, Hood,JE, Soni,AS, Wikswo,JP, Lipson,H. Automated Refinement and Inference of Analytical Models for Metabolic Networks, Phys.Biol., 8, 055011, 2011. PMCID: PMC4109817.

(56) References Cited

OTHER PUBLICATIONS

LeDuc,PR, Messner,WC, Wikswo,JP. How Do Control-Based Approaches Enter into Biology?, Annu.Rev.Biomed. Engr., 13, 369-396, 2011.

Yang,R, Lenaghan,SC, Wikswo,JP, Zhang,M. External Control of the GAL Network in S. Cerevisiae: A View From Control Theory, PloS.One., 6, e19353, 2011. PMCID: PMC3084829.

Irvin,MW, Zijlstra,A, Wikswo,JP, Pozzi,A. Techniques and Assays for the Study of Angiogenesis, Exp.Biol.Med., 239, 1476-1488, 2014. PMCID: PMC4216737.

Arnold,SA, Zijlstra,A, Hansen,AG, Schaffer,DK, Ashby,WJ, Wikswo,JP. Lab on a Chick: a Novel in Vivo Angiogenesis Assay, Clin.Exp. Metastas., 28, 296, 2011.

McLean,JA. The Mass-Mobility Correlation Redux: the Conformational Landscape of Anhydrous Biomolecules, J.Am.Soc.Mass.Spect., 20, 1775-1781, 2009.

Fenn,LS and McLean,JA. Biomolecular Structural Separations by Ion Mobility-Mass Spectrometry, Anal.Bioanal. Chem., 391, 905-909, 2008.

McLean,JA and Russel,DH. New Vistas for Mass Spectrometry-Based Proteomics and Biotechnology: Rapid Two-Dimensional Separations Using Gas-Phase Electrophoresis/Ion Mobility-Mass Spectrometry, Am.Biotechnol.Lab., 23, 18-21, 2008.

McLean,JA, Fenn,LS, Enders,JR. Structurally Selective Imaging Mass Spectrometry by Imaging Ion Mobility-Mass Spectrometry. In: Mass Spectrometric Imaging: History, Fundamentals and Protocols, Sweedler,JV, eds. Humana Press, New York, 363-383, 2010.

Hines,KM, Ballard,BR, Marshall,DR, McLean,JA. Structural Mass Spectrometry of Tissue Extracts to Distinguish Cancerous and Non-Cancerous Breast Diseases, Mol.Biosyst., 10, 2827-2837, 2014. PMCID: PMC4183709.

Eklund,SE, Cliffel,DE, Kozlov,E, Prokop,A, Wikswo,JP, Jr., Baudenbacher,FJ. Modification of the Cytosensor TM Microphysiometer to Simultaneously Measure Extracellular Acidification and Oxygen Consumption Rates, Anal.Chim. Acta, 496, 93-101, 2003.

Ciobanu,M, Taylor DE, Wilbur,JP, Cliffel,DE. Glucose and Lactate Biosensors for Scanning Electrochemical Microscopy Imaging of Single Live Cells, Anal.Chem., 80, 2717-2727, 2008. PMCID: PMC2836715.

SniderRM, Ciobanu,M, Rue,AE, Cliffel,DE. A Multiwalled Carbon Nanotube/Dihydropyran Composite Film Electrode or Insulin Detection in a Microphysiometer Chamber, Anal.Chim.Acta, 609, 44-52, 2008. PMCID: PMC2358927.

Zeiger,SLH, McKenzie,JR, Stankowski,JN, Martin,JA, Cliffel,DE, McLaughlin,B. Neuron Specific Metabolic Adaptations Following Multi-Day Exposures to Oxygen Glucose Deprivation, BBA-Mol. Basis.Dis., 1802, 1095-1104, 2010.

Shinawi,TF, Kimmel,DW, Cliffel,DE. Multianalyte Microphysiometry Reveals Changes in Cellular Bioenergetics Upon Exposure to Fluorescent Dyes, Anal.Chem., Accepted. manuscript, doi: 10.1021/ac402764x, 2013.

Velkovsky,M, Cliffel,D, Eklund,S, Eluvathingal,S, Stremler,MA, Wikswo,JP. Extracting Metabolic Fluxes From Measurements With a Multianalyte MicroPhysiometer. Biophysical Society 49th Annual Meeting, Long Beach, CA, 2558-Pos, 2005.

Antar,AAR, Konopka,JL, Campbell,JA, Henry,RA, Perdigoto,AL, Carter,BD, Pozzi,A, Abel,TW, Dermody,TS. Junctional Adhesion Molecule-A Is Required for Hematogenous Dissemination of Reovirus, Cell Host Microbe, 5, 59-71, 2009. PMCID: PMC2642927.

Boehme,KW, Guglielmi,KM, Dermody,TS. Reovirus Nonstructural Protein Sigma 1s Is Required for Establishment of Viremia and Systemic Dissemination, PNAS (US), 106, 19986-19991, 2009. PMCID: PMC2774258.

Lai,CM, Boehme,KW, Pruijssers,AJ, Parekh,VV, Van Kaer,L, Parkos,CA, Dermody,TS. Endothelial JAM-A Promotes Reovirus Viremia and Bloodstream Dissemination, J.Infect.Dis., 211, 383-393, 2015. PMCID: PMC4351375.

Lai,CM, Mainou,BA, Kim,KS, Dermody,TS. Directional Release of Reovirus From the Apical Surface of Polarized Endothelial Cells, MBio, 4, Article e00049-13 , 2013. PMCID: PMC3622924.

Danthi,P, Pruijssers,AJ, Berger,AK, Holm,GH, Zinkel,SS, Dermody,TS. Bid Regulates the Pathogenesis of Neurotropic Reovirus, PLoS Pathog., 6, Article e1000980, 2010. PMCID: PMC2895667.

Pruijssers,AJ, Hengel,H, Abel,TW, Dermody,TS. Apoptosis Induction Influences Reovirus Replication and Virulence in Newborn Mice, J.Virol., 87, 12980-12989, 2013. PMCID: PMC3838116.

Jangula,A and Murphy,EJ. Lipopolysaccharide-Induced Blood Brain Barrier Permeability Is Enhanced by Alpha-Synuclein Expression, Neurosci.Lett, 551, 23-27, 2013. PMCID: PMC3799901.

Uchida,Y, Ohtsuki,S, Katsukura,Y, Ikeda,C, Suzuki,T, Kamiie,J, Terasaki,T. Quantitative Targeted Absolute Proteomics of Human Blood-Brain Barrier Transporters and Receptors, J.Neurochem., 117, 333-345, 2011.

Easter,A, Bell,ME, Damewood,JR, Redfern,WS, Valentin,JP, Winter,MJ, Fonck,C, Bialecki,A. Approaches to Seizure Risk Assessment in Preclinical Drug Discovery, Drug Discov. Today, 14, 876-884, 2009.

De Clercq,E. Antiviral Drugs in Current Clinical Use, J.Clin.Virol., 30, 115-133, 2004.

Bromfield,EB, Cavazos,JE, Sirven,JL. Chapter 1, Basic Mechanisms Underlying Seizures and Epilepsy. In: An Introduction to Epilepsy [Internet], Bromfield,EB, eds. American Epilepsy Society, West Hartford, CT, 2006.

Bough,KJ, Gudi,K, Han,FT, Rathod,AH, Eagles,DA. An Anticonvulsant Profile of the Ketogenic Diet in the Rat, Epilepsy Res., 50, 313-325, 2002.

Chu,NS. Caffeine- and Aminophylline-Induced Seizures, Epilepsia, 22, 85-94, 1981.

Nistico,G, De Sarro,GB, Naccari,F, Musolino,R, Rotiroti,D, Gallitto,G, Di Perri,R. Cefazolin: a Valid Model of Experimental Epilepsy?, Monogr.Neural Sci., 5, 14-19, 1980.

\* cited by examiner

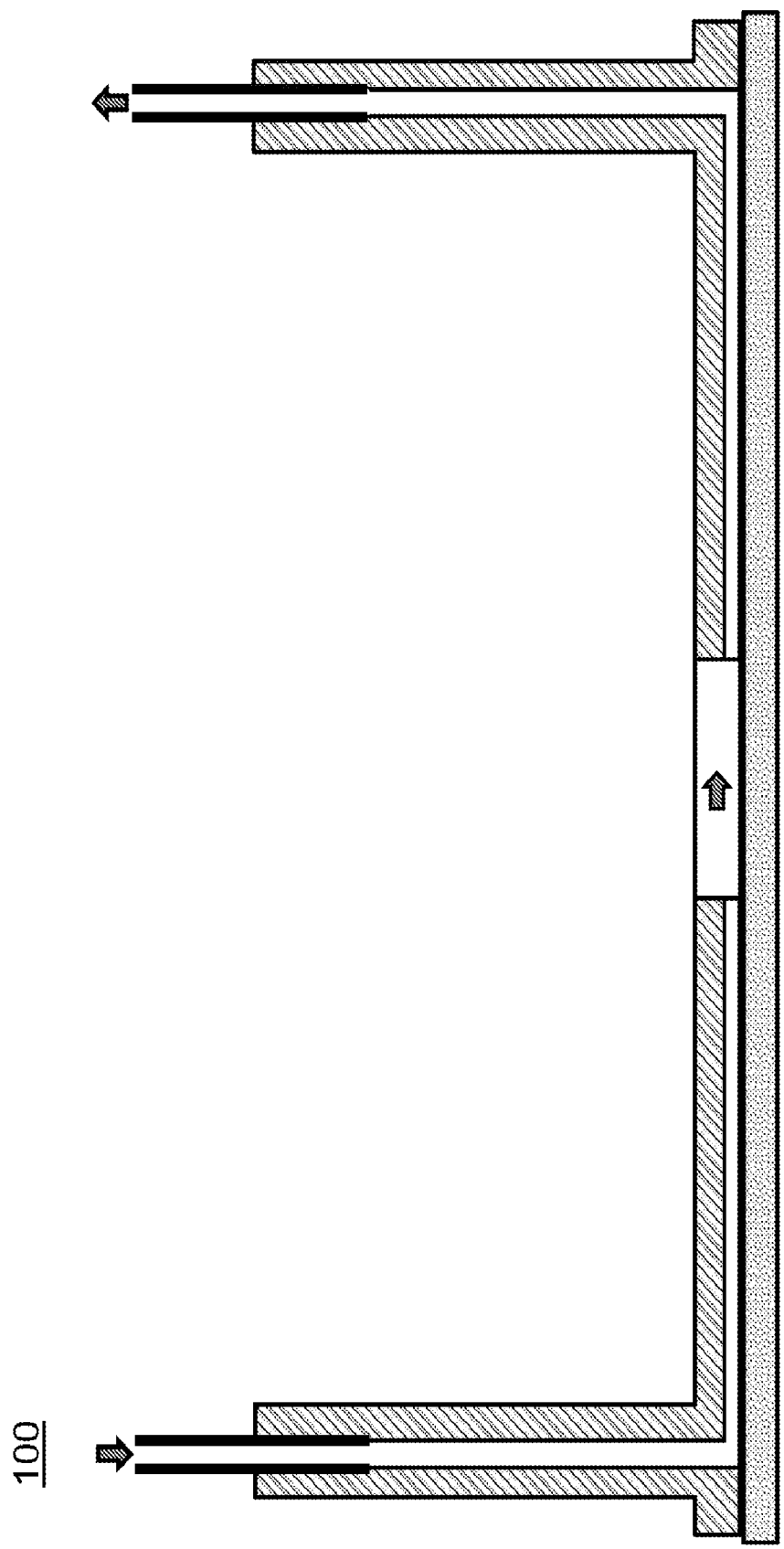

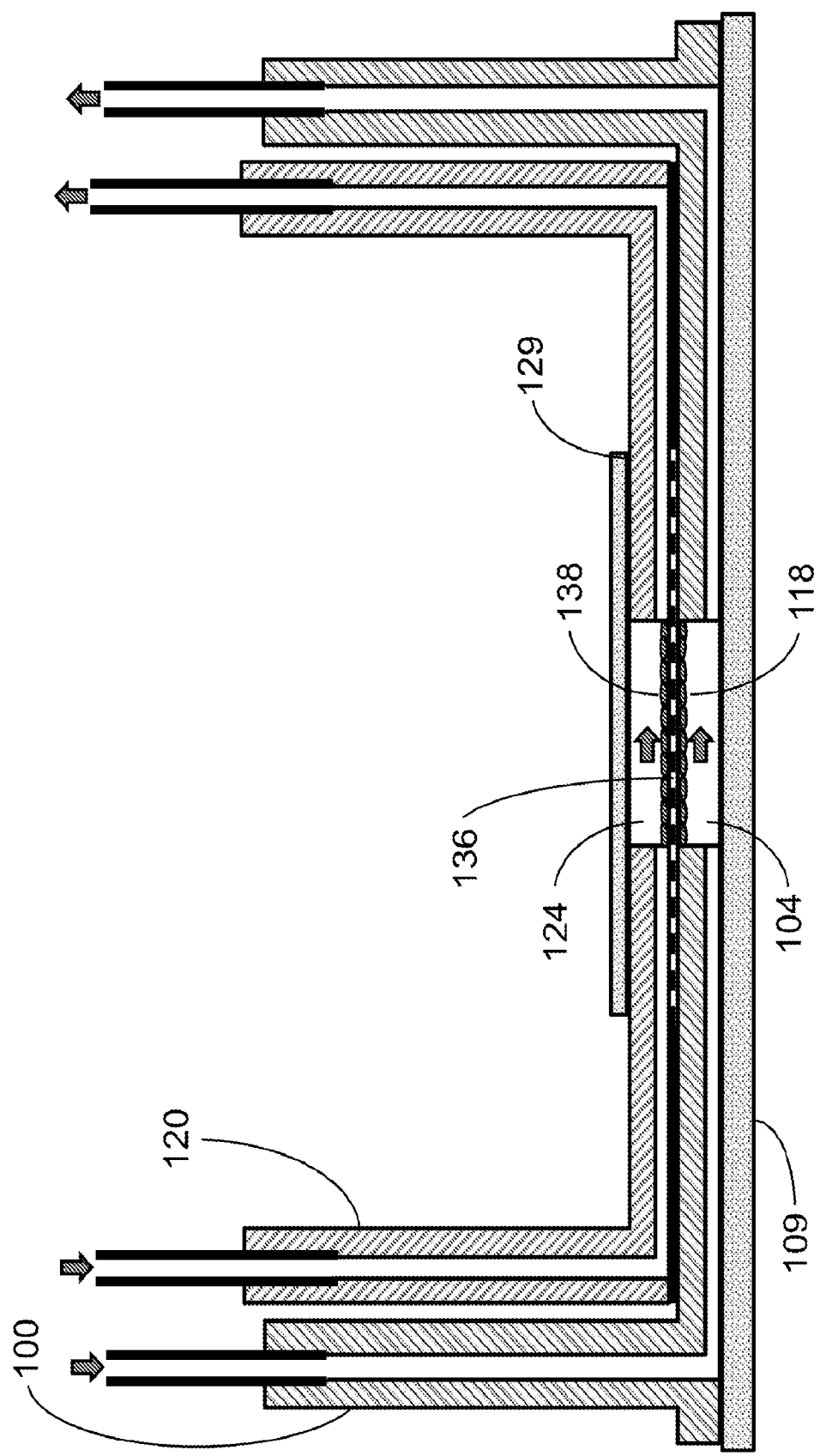

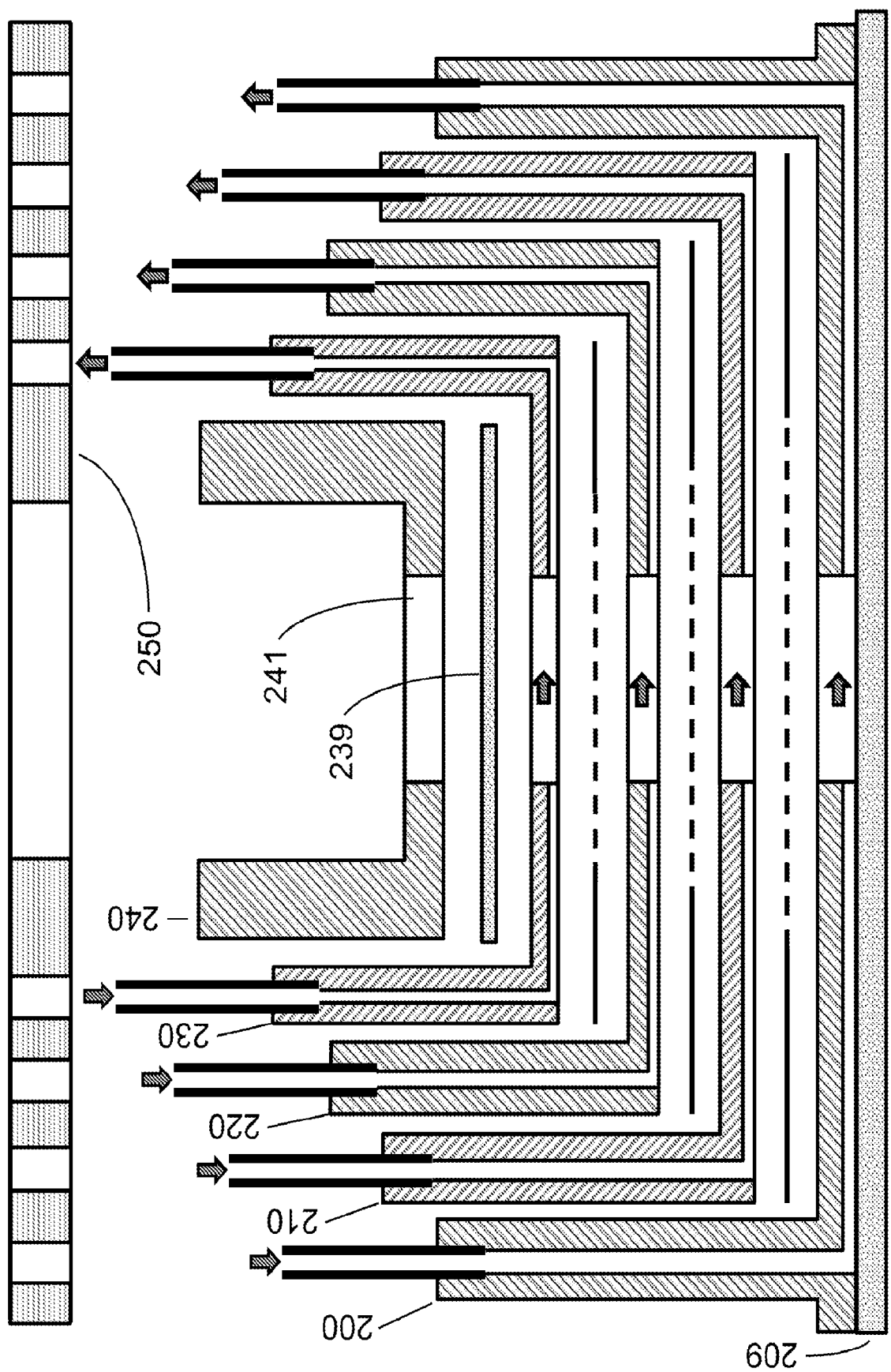

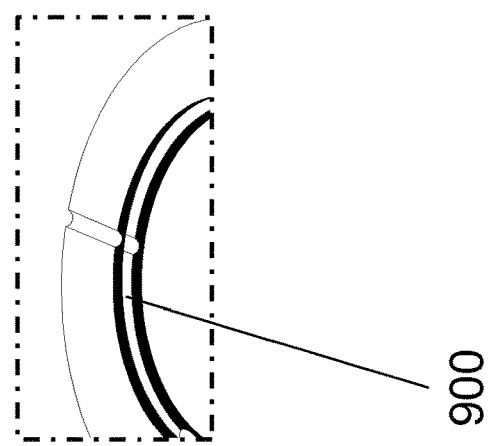
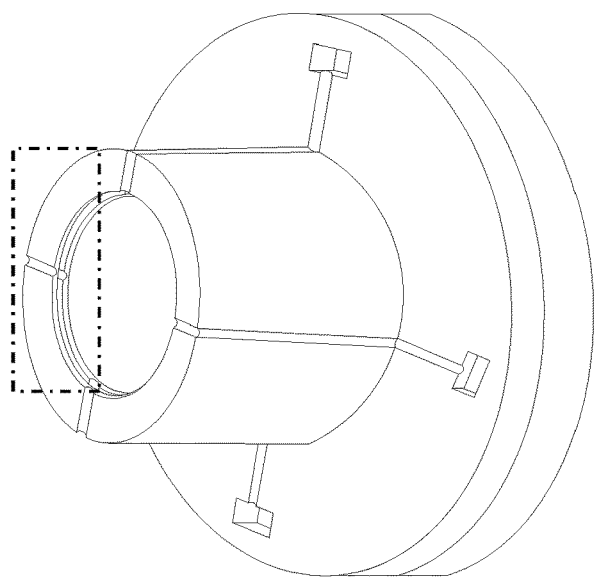
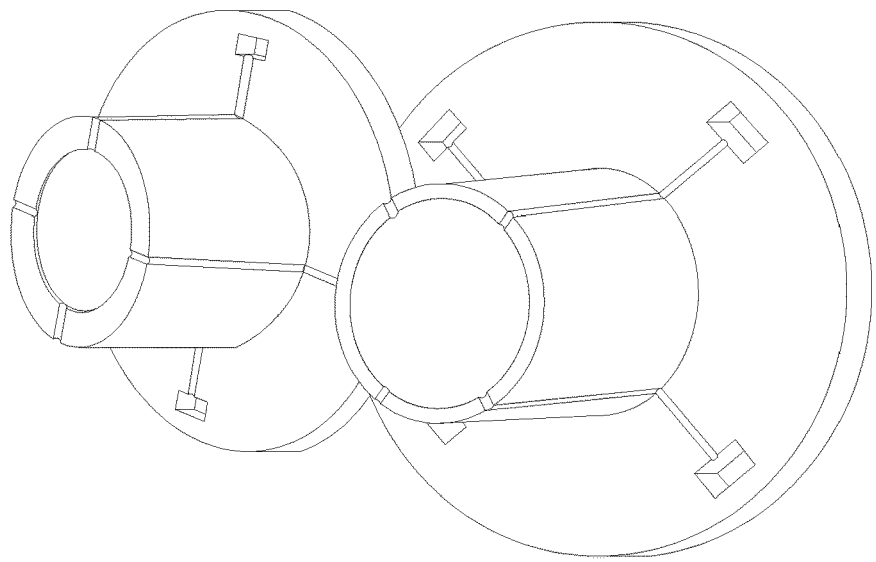
FIG. 9C
FIG. 9B
FIG. 9A

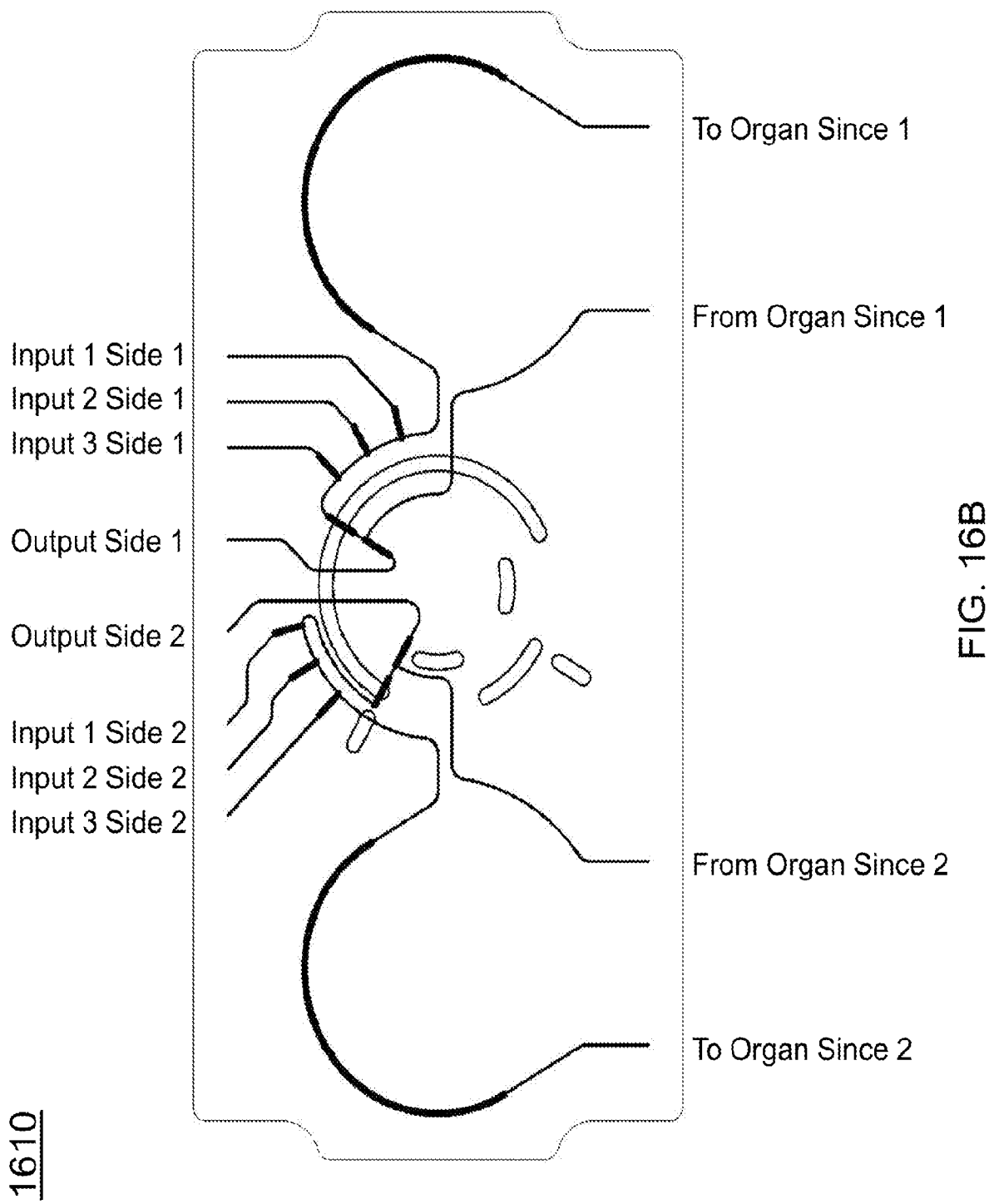

US 10,532,354 B2

MULTICOMPARTMENT LAYERED AND STACKABLE MICROFLUIDIC BIOREACTORS AND APPLICATIONS OF SAME

CROSS-REFERENCE TO RELATED PATENT APPLICATIONS

This PCT application claims priority to and the benefit of, U.S. Provisional Patent Application Ser. No. 62/259,327, filed Nov. 24, 2015. The entire disclosure of the above-identified application is incorporated herein by reference.

This PCT application also is a continuation-in-part application of U.S. application Ser. No. 15/191,092, filed Jun. 23, 2016; Ser. No. 14/651,174, filed Jun. 10, 2015; Ser. No. 14/646,300, filed May 20, 2015; Ser. No. 14/363,074, filed Jun. 5, 2014; and Ser. No. 13/877,925, filed Jul. 16, 2013. The entire disclosure of each of the above-identified applications is incorporated herein by reference.

STATEMENT OF FEDERALLY SPONSORED RESEARCH

The present invention was made with government support under Contract No. 1UH2-TR000491-01, awarded by the National Institutes of Health. The government has certain rights in the invention.

Some references, which may include patents, patent applications, and various publications, are cited and discussed in the description of the present invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The present invention relates generally to a microfluidic system, and more particularly to layered and stackable microfluidic bioreactors, and applications of the same.

BACKGROUND INFORMATION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

The blood-brain barrier (BBB) acts as the gatekeeper between the central nervous system (CNS) and the rest of the body. It is the responsibility of the BBB to facilitate the entry of required nutrients into the brain and exclude potentially harmful compounds. However, this critical and complex structure remains difficult to model in vitro. Accurate in vitro models are necessary for understanding how the BBB forms and functions, for evaluating drug, toxin, and viral penetration across the barrier, and for recreating the BBB response and CNS response in disease models. Many existing in vitro models either fail to support all the cell types involved in BBB formation and/or do not provide the shear forces created by flow necessary for mature tight junction formation. While the transwell BBB with endothelial cells and astrocytes is a standard in the pharmaceutical industry, its shortcomings include the lack of shear-flow induced polarization of the endothelial cells; large, physiologically unrealistic fluid volumes; difficulty in supporting more than two cell types; and the inability to use electrical recordings to monitor neural activity in situ. There are a large number of different applications of biological barriers that are studied using transwell, including the endothelia/epithelial/air interface at the skin, the endothelial/epithelial interface within the pulmonary alveoli, the endothelial/epithelial interface in the lumen of the gastrointestinal tract, etc., that would benefit from lower fluid volumes and improved, shear-flow-induced polarization. Transwells also have widespread application as a cancer cell migration tool, wherein cells within the insert migrate across the barrier in response to chemical signals produced by cells growing at the bottom of the well. The ability of the cells in the insert to sense the signals from cells in the well is compromised by the dilution of signaling molecules and metabolites by the large fluid volumes in both the well and the insert.

Therefore, a heretofore unaddressed need exists in the art to address the aforementioned deficiencies and inadequacies.

SUMMARY OF THE INVENTION

In one aspect, the present invention relates to a planar layered device. In certain embodiments, the planar layered device includes a top planar layer and a bottom planar layer stacked together. The top planar layer includes a top base having an upper surface and a lower surface, a top cover covering the upper surface of the top base, and a top membrane attached to the lower surface of the top base. The top base has a top through hole formed therein, the top through hole is sealed by the top cover and the top membrane to form a top chamber, and the top chamber is in fluid communication with a first input channel and a first output channel located in the top base. The bottom planar layer includes a bottom base having an upper surface and a lower surface, and a bottom substrate attached to the lower surface of the bottom base. The bottom base has a bottom through hole formed therein, the bottom through hole is sealed by the top membrane and the bottom substrate to form a bottom chamber, and the bottom chamber is in fluid communication with a second input channel and a second output channel located in the bottom base. The top chamber and the bottom chamber correspond to each other and are separated by the top membrane.

In certain embodiments, the planar layered device further includes at least one middle planar layer disposed between the top planar layer and the bottom planar layer. The at least one middle planner layer includes a middle base having an upper surface and a lower surface. The top membrane is disposed between the lower surface of the top base and the upper surface of the middle base, and a middle membrane is disposed between the lower surface of the middle base and the upper surface of the bottom base. The middle base has a middle through hole formed therein, the middle through hole is sealed by the top membrane and the middle membrane to form a middle chamber, and the middle chamber is in fluid communication with a third input channel and a third output channel located in the middle base.

In certain embodiments, the first input channel and the first output channel are recessed from the lower surface of the top base, the second input channel and the second output channel are recessed from the lower surface of the bottom base, and the third input channel and the third output channel are recessed from the lower surface of the middle base.

In certain embodiments, the at least one middle planar layer includes multiple middle planar layers.

In certain embodiments, a thickness of the top membrane and the middle membrane is in a range of about 2-20 µm, a height of the top chamber, the middle chamber and the bottom chamber is in a range of about 50-150 µm. In one embodiment, the thickness of the top membrane and the middle membrane is in a range of about 10 µm. In one embodiment, the height of the top chamber, the middle chamber and the bottom chamber is in a range of about 100 µm.

In certain embodiments, the top chamber, the middle chamber and the bottom chamber are aligned sequentially with each other, the top membrane is porous or a portion of the top membrane corresponding to the top chamber and the middle chamber is porous, and the middle membrane is porous or a portion of the middle membrane corresponding to the middle chamber and the bottom chamber is porous.

In certain embodiments, each of the top planar layer, the middle planar layer and the bottom planar layer further has sidewalls surrounding the top base, the middle base or the bottom base.

In certain embodiments, the planar layered device further includes a top cell layer disposed between a bottom surface of the top chamber and the top membrane, and a bottom cell layer disposed between the top membrane and an upper surface of the bottom chamber. In certain embodiments, the top cell layer comprises brain astrocytes and pericytes, and the bottom cell layer comprises brain microvascular cells.

In certain embodiments, the top cover and the bottom substrate are made of glass.

In certain embodiments, the base for each layer supports the membrane filter that separates two chambers. The thin base is supported on its edges by a surrounding, thicker and stiffer frame. The lateral dimensions of the frame for each successive layer are such that the frame for the lowest layer is largest, and the frame for successive upper layers is progressively reduced so that the upper layers nest inside the lower ones. In some embodiments, the set of nested layers can be clamped together to eliminate leaks from the channels of each layer and allow the layers to be disassembled for cellular analysis.

In another aspect, the present invention relates to a stackable transwell device. In certain embodiments, the stackable transwell device includes a top transwell insert, at least one middle transwell insert, and a bottom transwell insert. Each of the bottom transwell insert, the at least one middle transwell insert and the top transwell insert has a tubular body and a flange radially extending from an upper end of the tubular body, such that, as assembled, the flange of the top transwell insert stacks on the flange of the at least one middle transwell insert that in turn, stacks on the flange of the bottom transwell insert, and the tubular body of the top transwell insert is sleeved by the tubular body of the at least one middle transwell insert that in turn, is sleeved by the tubular body of the bottom transwell insert. A top cover is attached to a lower end of the tubular body of the top transwell insert, a middle membrane is attached to a lower end of the tubular body of the at least one middle transwell insert, a bottom substrate is attached to a lower end of the tubular body of the bottom transwell insert. The top cover, the middle membrane, and the tubular bodies of the top transwell insert and the at least one middle transwell insert define a top chamber, and the top chamber is in fluid communication with a first input channel and a first output channel. The middle membrane, the bottom substrate, and the tubular bodies of the at least one middle transwell insert and the bottom transwell insert define a bottom chamber, and the bottom chamber is in fluid communication with a second input channel and a second output channel.

In certain embodiments, the at least one middle transwell insert includes two or more middle transwell inserts, and a middle chamber is defined between two adjacent middle transwell inserts, and the middle chamber is in fluid communication with a third input channel and a third output channel.

In certain embodiments, the at least one middle transwell insert includes two middle transwell inserts, the middle membrane comprises a first middle membrane and a second middle membrane defining the middle chamber, a first type of cell layer is attached to a bottom surface of the top cover and an upper surface of the first middle membrane, a second type of cell layer are attached to a bottom surface of the first middle membrane and an upper surface of the second middle membrane, and a third type of cell layer is attached to a bottom surface of the second middle membrane and an upper surface of the bottom substrate.

In certain embodiments, each of the first input channel, the first output channel, the second input channel, the second output channel, the third input channel, and the third output channel is recessed from the lower end of one of the tubular bodies, and disposed between two adjacent tubular bodies.

In certain embodiments, the lower end of each tubular body has a diameter less than that of the upper end of the tubular body, and the top chamber, the middle chamber and the bottom chamber are in fluid communication with each other through the top membrane and the middle membrane.

In certain embodiments, a height of each of the top chamber, the middle chamber and the bottom chamber is in a range of about 50-150 µm. In one embodiment, the height of each of the top chamber, the middle chamber and the bottom chamber is about 100 µm.

In certain embodiments, the top cover and the bottom substrate are made of glass.

In a further aspect, the present invention relates to a stackable device. In certain embodiments, the stackable device includes multiple elements stacked sequentially to each other. A chamber is formed in each of the elements or between adjacent two of the elements, and each chamber is in fluid communication with an input channel and an output channel. The chambers are aligned with each other, and adjacent two chambers are separated from each other by a membrane.

In certain embodiments, each of the elements is a planar layer or a transwell insert.

In yet another aspect, the present invention relates to a system. In certain embodiments, the system includes at least one stackable device, each stackable device having multiple chambers; and at least one of a perfusion controller, a microformulator, and a microclinical analyzer in fluid communication with the at least one stackable device.

In certain embodiments, the perfusion controller is configured to provide media for growing cells in the chambers and includes: a plurality of reservoirs, wherein one reservoir has a media; an input control valve connected with the reservoirs; and a pump connected with the input control valve for drawing a reagent from the reservoirs via the input control valve. The multiple chambers of the at least one stackable device are connected with the pump for receiving the reagent or connected with the media reservoir for sending out effluent to the media reservoir.

In certain embodiments, the microformulator is configured for feeding a single reagent or a mixture of reagents to cells in the chambers and includes: a plurality of reservoirs containing different reagents for testing; an input control valve connected with the reservoirs; a pump connected with the input control valve for drawing a reagent from the reservoirs via the input control valve; and an output director valve having multiple output tubes. The multiple output tubes are configured to feed the reagent to chambers of the stackable device with predetermined concentrations of the different reagents, which may change with time to produce complex temporal concentration profiles.

In certain embodiments, the microclinical analyzer is configured to analyze the effluent from the chambers and includes: a plurality of reservoirs containing calibration reagents; a valve connected with the reservoirs and connected with a tube for receiving effluent from the chambers of the stackable device; a pump connected with the valve for drawing the calibration reagents or the effluent; and a sensor array connected with the pump for analyzing the calibration reagents or the effluent.

In certain embodiments, the pumps, valves and tubing can be configured with current-injection electrodes, voltage-sensing electrodes, and a fixed- or swept-frequency analyzer to create an integrated instrument that is capable of measuring either the transendothelial electrical resistance (TEER) performing electrical impedance spectroscopy on the cells growing on each transwell barrier in a multi-well plate.

In certain embodiments, the at least one of the perfusion controllers, the microformulators, and the microclinical analyzers comprises a first input microformulator, comprising a first pump in fluid communication with reservoirs, a first valve in fluid communication with the first pump through at least one first fluidic path, and a first electrode at least partially disposed in the at least one first fluidic path; a second input microformulator, comprising a second pump in fluid communication with the reservoirs, a second valve in fluid communication with the second pump through at least one second fluidic path, and a second electrode at least partially disposed in the at least one second fluidic path; a first output microformulator, comprising a third pump, a third valve in fluid communication with the third pump through at least one third fluidic path, and a third electrode at least partially disposed in the at least one third fluidic path; and a second output microformulator, comprising a fourth pump, a fourth valve in fluid communication with the fourth pump through at least one fourth fluidic path, and a fourth electrode at least partially disposed in the at least one fourth fluidic path.

In certain embodiments, the system further comprises an impedance analyzer electrically coupled with the first, second, third and fourth electrodes.

In certain embodiments, the impedance analyzer is configured to deliver a first electrical signal through the first and second electrodes respectively to two sides of a barrier in the at least one stackable device, and to measure a second electrical signal of the two sides of the barrier through the third and fourth electrodes respectively.

In certain embodiments, the system further comprises a plurality of input fluidic lines, and each input fluidic line is electrically connected with the first electrode or the second electrode through the first valve or the second valve.

In certain embodiments, the system further comprises a plurality of output fluidic lines, and each output fluidic line is electrically connected with the third electrode or the fourth electrode through the third valve or the fourth valve.

In certain embodiments, the first electrode and the second electrode operably deliver the first electrical signal through corresponding input fluidic lines respectively to the two sides of the barrier; and the third electrode and the fourth electrode operably measure the second electrical signal of the two sides of the barrier through corresponding output fluidic lines respectively.

In certain embodiments, one of the first and second electrical signals is a current, and the other of the first and second electrical signals is a voltage.

In certain embodiments, the barrier comprises membranes between the chambers or between the transwell inserts and their corresponding wells.

These and other aspects of the present invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the present invention and, together with the written description, serve to explain the principles of the invention. Wherever possible, the same reference numbers are used throughout the drawings to refer to the same or like elements of an embodiment.

FIG. 1C is a cross-sectional view of FIG. 1A along the A-A' direction after attaching the glass substrate.

FIG. 1G is a cross-sectional assembly view of a double-layer microfluidic bioreactor.

FIG. 2A is a cross-sectional exploded view of a five-layer microfluidic bioreactor according to one embodiment of the present invention.

FIG. 9A is an image of two stackable transwell inserts fabricated by 3D printing according to one embodiment of the present invention.

FIG. 9B is an image showing the stack of the two transwell inserts in FIG. 9A.

FIG. 9C is a partial enlarged view of FIG. 9B showing a gap between the two transwell inserts.

FIG. 16B shows a fluidic circuit according to one embodiment of the present invention.

DETAILED DESCRIPTION OF THE INVENTION

Figure 1A:
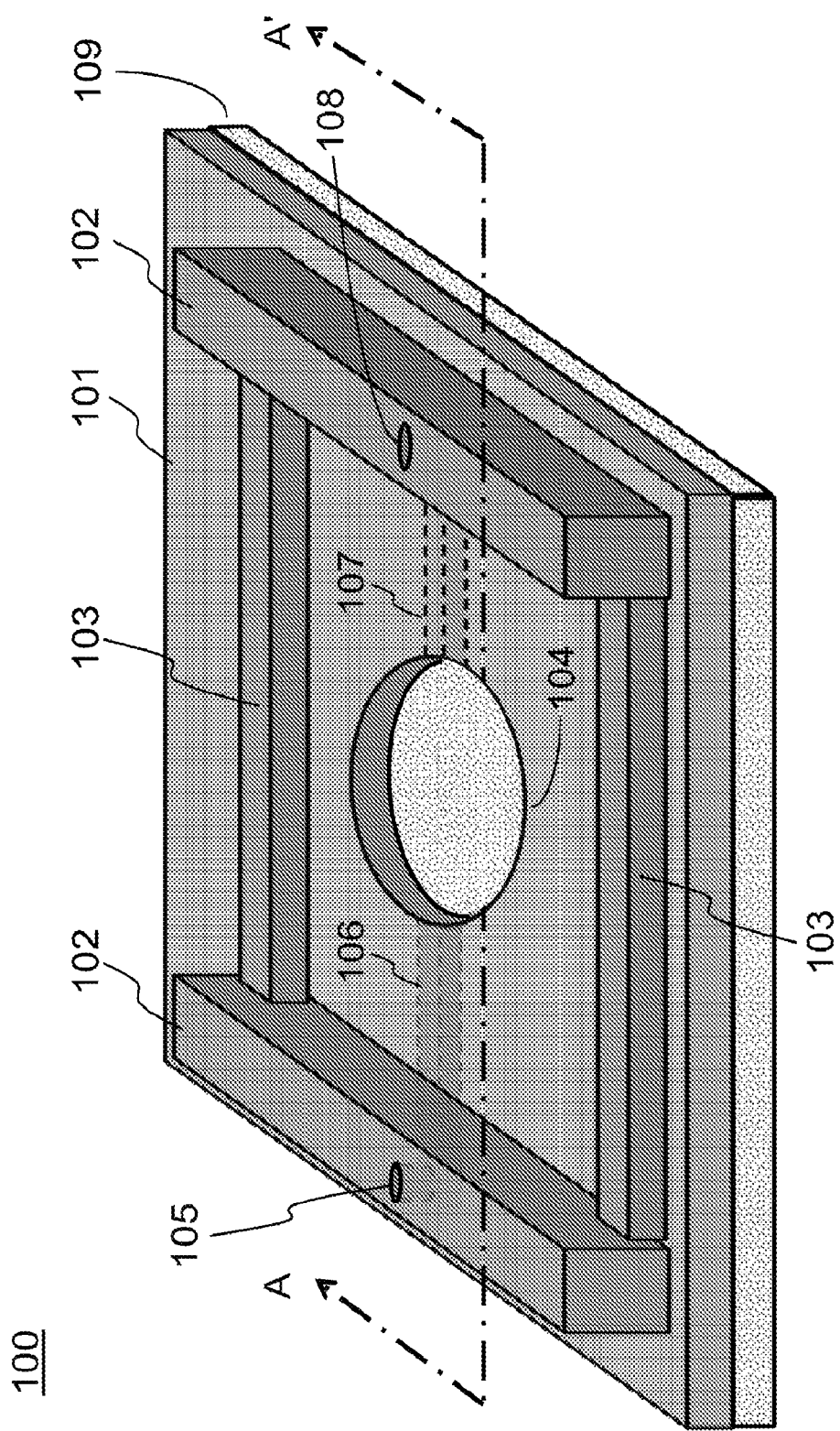
FIG. 1A shows schematically a perspective view of a single chamber layered microfluidic bioreactor according to one embodiment of the present invention.

The present invention will now be described more fully hereinafter with reference to the accompanying drawings, in which exemplary embodiments of the present invention are shown. The present invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the present invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the terms "MicroClinical Analyzer," "MicroChemical Analyzer," and their abbreviation "μCA" are exchangeable. The term "Perfusion Controller" and its abbreviation "PC" are exchangeable. The term "MicroFormulator" and its abbreviation "μF" are exchangeable. The term "Rotary Planar Peristaltic Micropump" and its abbreviation "RPPM" are exchangeable. The term "Rotary Planar Valve" and its abbreviation "RPV" are exchangeable. The term "Integrated Organ Microfluidics" and its abbreviation "IOM" are exchangeable. The term "Organ-on-Chip" and its abbreviation "OoC" are exchangeable. The term "tissue chip" and its abbreviation "TC" are exchangeable.

As used herein, the terms "fluidic path" and "fluidic channel" are exchangeable, and refer to a passage, a conduit, a groove, a furrow, or the like that allow a fluid to flow through it. Similarly, "bus line," "bus," and "line" can be used interchangeably and refer to a common fluidic supply line or a set of common fluidic supply lines.

The description is now made as to the embodiments of the present invention in conjunction with the accompanying drawings. In accordance with the purposes of the present invention, as embodied and broadly described herein, the present invention relates to systems and methods using layered planar microfluidics and stacked transwell microfluidic.

In certain embodiments, a planar microfluidic BBB model is provided, which is excellent for examining the BBB in cross-section, particularly to observe leukocyte extravasation, but it lacks the cell number to support in-depth secretome characterization.

In certain embodiments, a hollow fiber BBB model is provided. The hollow fiber BBB model provides the shear flow for barrier polarization and support leukocyte extravasation, but have large abluminal volumes, a thick membrane between the endothelial cells and astrocytes, and support neither electrical recordings nor optical microscopy of the endothelium. Hollow fibers are typically translucent rather than transparent and hence do not allow visualization of cells growing within the lumen of the fiber.

In certain embodiments, a more faithful in vitro BBB model is provided. The in vitro BBB model is a microfluidic neurovascular unit (NVU) that includes a vascular chamber and a brain chamber separated by a porous membrane that allows cell-cell communication between endothelial cells, astrocytes, and pericytes, and that can independently perfuse both sides of the membrane.

In certain embodiments of a BBB model, a cerebral-spinal fluid (CSF) compartment is added. In certain embodiments, human cells, including induced pluripotent stem cell (iPSC) derived glutamatergic neurons are used. In certain embodiments, all cell types that comprise the BBB-NVU model are derived from iPSCs, possibly from the same patient to provide genetic homogeneity of all cells in the BBB-NVU.

In certain embodiments, a complete next-generation neurovascular unit-integrated microfluidics module (NVU-IOM) system with fully transparent materials is provided. The NVU-IOM system supports long-term culture, control, characterization, and validation well beyond what is currently available. By combining several emerging technologies into a single platform, the NVU-IOM will enable in situ and real-time morphometric, neuroelectric, bioenergetic, and metabolomic characterization of both the BBB and the neurons it protects. In certain embodiments, the integrated platform is generalizable to organ-on-chip (OoC) systems capable of establishing physiologically relevant protective barriers ranging from fetal membranes to the liver, skin, lungs, airways, kidney and bladder, and hence will advance not only neuroscience but also toxicology and drug safety.

In certain embodiments, a well plate set up is used in cell biology analysis. The well plate, robots, and plate-based instruments are central to high-throughput screening (HTS) and drug development. As a result, much of biology utilizing those tools has focused on monolayer monocultures grown on plastic. The resulting self-consistent biological models have a number of serious limitations: small-volume wells with a supposedly homogeneous cellular phenotype do not recapitulate the heterogeneous tissue microenvironment (both physical and chemical); nutrient and metabolite transport is limited by diffusion; well corners may not reflect well centers; and it is hard to create controlled concentration gradients or reverse experiments through rapid washout. Plastic is $10^4$ to $10^5$ times stiffer than tissue, and standard well plates are not designed to provide shear forces to maintain endothelial and epithelial polarization or apply mechanical stresses to cells. A centralized fluid handler and plate reader hardware are not suited for either fast, real-time, closed-loop control or complex exposure protocols. Paracrine and autocrine factors are diluted 100× to 1000× by the media above cells. It is difficult to create well-well connections to simulate organ-organ interactions, and a simple pipetting of conditioned media from one well to another will lead to further dilution, evaporation, or other losses.

In certain embodiments, recognizing the above described limitations, 3D tissue culture with heterogeneous cell populations in 3D extracellular matrices with tissue-like architecture, perfusion, stiffness, and proper mechanical, chemical, and electrical clues is provided. However, when studying with self-assembling organoids or perfused organs-on-chips, these problems and the difference between 2D and 3D cultures become more evident and must be addressed, while instrumentation enabling such culture maintenance, real-time analysis, and very low fluidic volumes is lacking in control, temporal resolution, and analytical sensitivity.

In certain embodiments, an interface is provided between biology, chemistry, physics, engineering, and medicine, to address the above identified problems during the transition from 2D to 3D cultures. Specifically, a NeuroVascular Unit (NVU) and supporting microfluidic pumps, valves, and controllers have been developed, which represents state-of-the-art organ-on-chip (OoC) research. This invention is innovative in that it presents a coherent plan to bring together a breadth of technologies, scientists, and engineers to create integrated organ microfluidics (IOM) modules that, when used with the NVU or other OoCs, provide a compact, low-cost, reliable, easy-to-use platform. The NVU-IOM platform can be incorporated into an instrument that enables real-time, on-chip interfaces with analytics such as TEER (Trans-Endothelial Electrical Resistance), multielectrode arrays (MEA) that capture spatiotemporal neuroelectric network dynamics, and metabolic profiling. This invention is capable of providing an NVU-IOM to academic and commercial researchers to advance our understanding of the BBB and brain neurons, and their response to drugs, toxins, and disease.

In certain embodiments, a complete NVU-IOM system, which may be a commercial pre-production prototype utilizing techniques in the area of biopharmaceutical, OoC, PDMS and other polymers, and precision molded plastic components. The implementation of this concept addresses three areas: the NVU bioreactor, support and analysis hardware, and validation of the NVU-IOM system. In certain embodiments, extensive preliminary data that provides proof-of-concept of the NVU and the individual components are available, and so the investigator can focus on integration, reliability, reproducibility, ease-of-manufacture, ease-of-use, and minimization of cost.

In certain embodiments, the integration goes beyond the microfluidics, and the NVU-IOM provides the ability to quantify bioenergetic activity by in situ, real-time measurement of glucose, lactate, and oxygen fluxes and cellular acidification rates, and the temporal variation of other cellular signals and metabolites. The NVU-IOM supports both targeted and untargeted ultraperformance liquid chromatography-ion mobility-mass spectrometry (UPLC-IM-MS) metabolomics.

In certain embodiments, layered planar microfluidics and stackable transwell inserts microfluidics are provided, each a significant advance in the NVU. The layered planar and stackable transwell NVU can be fabricated from cyclic olefin copolymer (COC), a plastic favored by the HTS community for its optical properties and biocompatibility. These NVUs support vascular, brain, and cerebral spinal fluid (CSF) spaces and can be optimized for high-content imaging. In certain embodiments, the NVU is directly interfaced to a complementary metal oxide semiconductor (CMOS) 4096 channel multi-electrode array (MEA) that allows the user to determine the neuroelectric response of neurons to drugs, toxins, and metabolic insults to the BBB and the neurons themselves. The sensitivity and specificity of the assays developed for the NVU-IOM are validated using the above techniques. The NVU-IOM is a powerful platform to aid understanding, protection, and treatment of the brain.

In certain aspects, the present invention relates to a bioreactor stacked of multiple planar layers. Referring to FIGS. 1A-5E, a layered, planar, multi-chamber bioreactor or microfluidics according to certain embodiments is shown. Of them, FIG. 1A explains a concept by which a layered, planar, multi-chamber bioreactor can be fabricated and assembled.

Referring to FIG. 1A, a single-chamber assembly or a first chamber assembly 100 consists of a microfluidic device that has a number of features that can be created by either bonding of individual components or by their casting or embossing or injection molding as an integral unit. The first chamber assembly 100 (or a lower chamber assembly) includes a first base layer 101, first port blocks 102, first struts 103, and a glass substrate 109. The first port blocks 102 and the first struts 103 are disposed on the first base layer 101. In certain embodiments, a thickness of the first base layer 101 may be as little as 50 to 100 microns (μm) to minimize the volume of the chamber formed in the first base layer 101. In other embodiments, the thickness of the first base layer 101 may be one millimeter (mm) or more to support thick tissues. The two first port blocks 102 are disposed opposite to each other and in parallel to each other. The two first struts 103 are disposed between the two first port blocks 102, and are disposed opposite to each other and in parallel to each other. The two first port blocks 102 and the two first struts 103 form a shape of a rectangle. The structure of the first port blocks 102 and the first struts 103 support the thinner first base layer 101 on all sides and allow manipulation of a rigid assembly rather than an unsupported thin film of the first base layer 101.

A first chamber (or a lower chamber) 104 is formed as a hole or opening in the first base layer 101, which may be located at the center of the first base layer 101, or not in the center. In certain embodiments, the first chamber 104 is a circular chamber. As described above, the thickness of the first base layer 101 determines the height of the first chamber 104, and may be as little as 50-100 μm to minimize the volume of the first chamber 104. In other embodiments, the thickness of the first base layer 101 may be greater than 1 mm to support thick tissues. A first input channel 106 and a first output channel 107 are molded or embossed into the lower surface of the first base layer 101 and in communication with the first chamber 104. The first input channel 106 is located at the left side of the first base layer 101, and the first output channel 107 is located at the right side of the first base layer 101. As shown in FIG. 1A, a first input port 105 is formed in the first port block 102 located at the left side, and a first output port 108 is formed in the first port block 102 located at the right side. The first input port 105 is connected to the first input channel 106, and the first output port 108 is connected to the first output channel 107, such that the first input port 105 and the first output port 108 are communicatively connected with the first chamber 104 via the first input channel 106 and the first output channel 107, respectively. In operation, a liquid flows into the first input port 105, passes sequentially the first input channel 106, the first center chamber 104, the first output channel 107, and flows out from the first output port 108. This entire object or assembly is either bonded or clamped to the glass substrate 109 that forms the bottom of the first assembly 100 and provides a window to visualize the contents of the first chamber 104.

The use of first port blocks 102 and first struts 103 is central to this embodiment, in that it allows the first base layer 101 to be very thin, for example between 50 and 100 μm, such that the height of the first chamber 104 in the center of the first base layer 101 to be only slightly greater than the thickness of one or two cell layers that would be grown on the surfaces that define the top and bottom of the first chamber 104. The first port blocks 102 and first struts 103 surround the thin first base layer 101 just as a picture frame surrounds a fragile piece of paper, allowing the frame-paper assembly to be handled without creasing or folding the paper. With this approach, it is possible to minimize the volume of fluid associated with the cells growing in that chamber, i.e., the ratio of media volume to cell volume, thereby minimizing the dilution of endocrine, paracrine, autocrine factors and secreted metabolites that may be important in both influencing the activity of the cells in this or other connected devices, and maximizing the ability to detect and quantify these species.

Figure 1B:
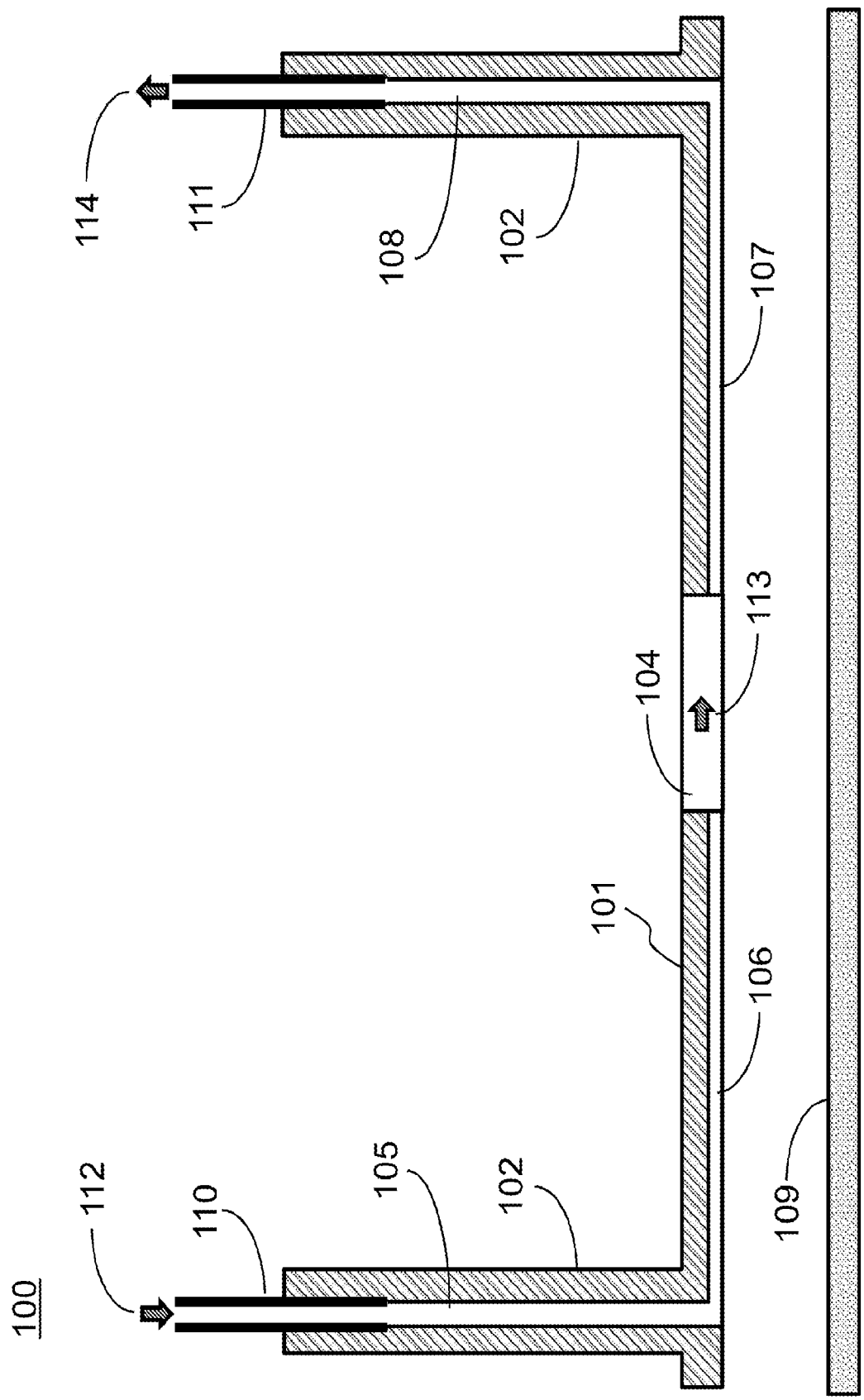
FIG. 1B is a cross-sectional view of FIG. 1A along the A-A' direction before attaching the glass substrate.

FIG. 1B is the section view of FIG. 1A along the AA' direction. As shown in FIG. 1B, a first input tube 110 is insertable to the first input port 105 and supports first input flow 112, and a first output tube 111 is insertable to the first output port 108 and supports first output flow 114. The punched or molded input and first output ports 105 and 108 connect to first input channel 106 and first output channel 107 to provide first flow 113 across the first chamber 104. The first input/output channels 106 and 107 and the first chamber 104 are sealed from the bottom by the transparent glass or plastic slide or cover slip 109 that is bonded or clamped to the lower surface of the first base layer 101 to create the first assembly 100 shown in cross section in FIG. 1C. In this example, the vertical ports 105/108 that connect the tubing 110/111 to the corresponding channels 106/107 in the lower surface of 101 can be either molded at the time of manufacture or punched, for example after casting PDMS into a mold. It is important to recognize that it is much easier to cast or punch a short port than it is to cast a complex, closed microfluidic network.

Figure 1D:
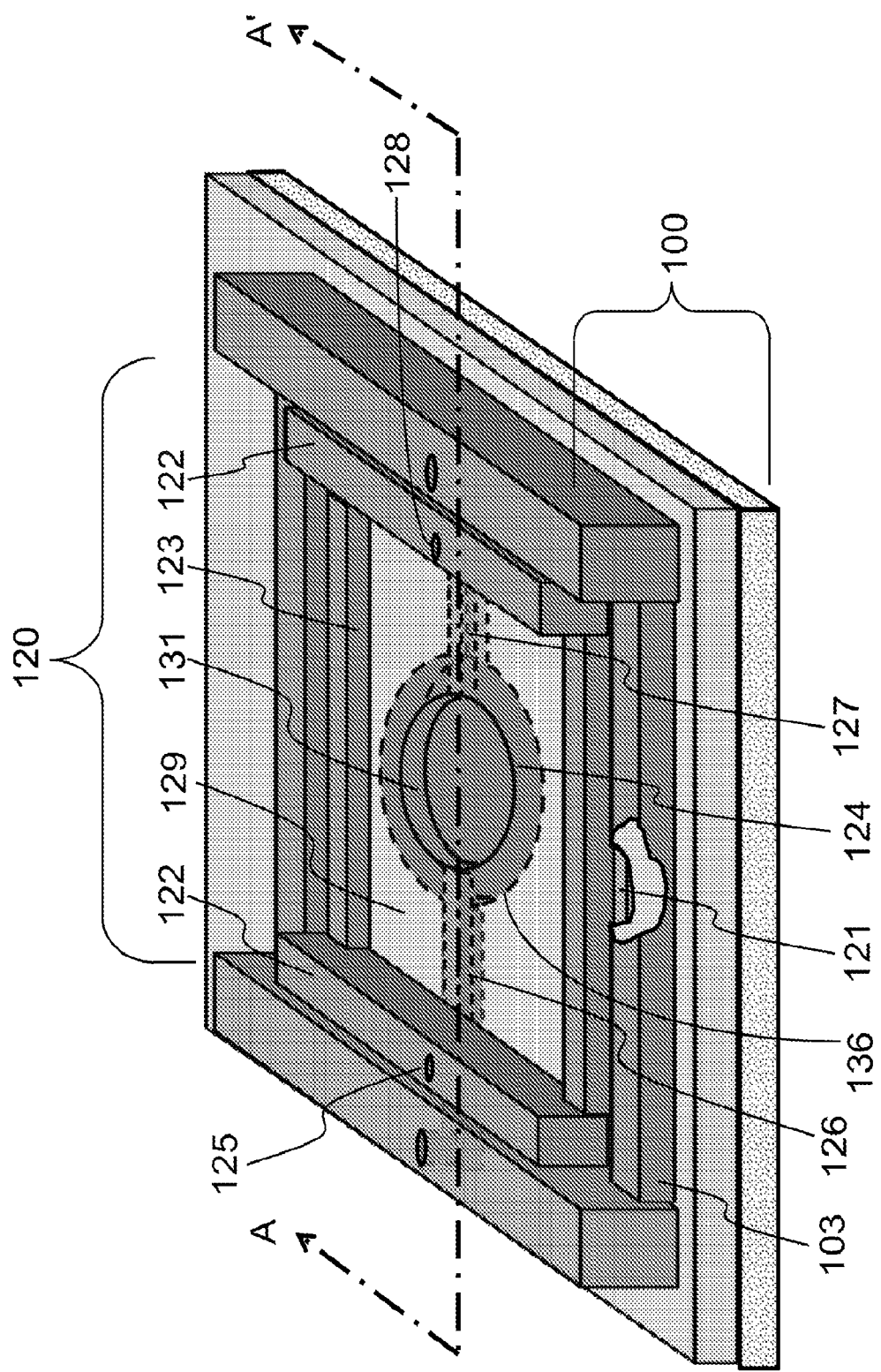
FIG. 1D shows schematically a perspective view of a double-layer microfluidic bioreactor according to one embodiment of the present invention.

A key feature according to certain embodiments of the present invention is that subsequent layers can be added to create multiple, stacked, interconnected chambers as shown in FIG. 1D by creating a smaller version 120 of assembly 100 where the lower glass layer that seals the bottom of the first layer is replaced by a porous filter, screen, or grid 136 that forms the bottom of the second layer. As shown in FIG. 1D, the second chamber assembly 120 includes a second base layer 121 (revealed by the cut-away in 103), second port blocks 122 and second struts 123. The second port blocks 122 and the second struts 123 sit on the second base layer 121 and within corresponding port blocks 102 and struts 103 of the first chamber assembly 100. A second chamber (or upper chamber) 124 is formed as a hole or opening in the second base layer 121, which may be located at the center of the second base layer 121. In certain embodiments, the second chamber 124 is a circular chamber. As described above, the thickness of the second base layer 121 determines the height of the second central chamber 124, and may be as little as 50-100 μm to minimize the volume of the second chamber 124. In other embodiments, the thickness of the second base layer 121 may be greater than 1 mm to support thick tissues. The top of the second chamber 124 is sealed by a transparent cover 129 fabricated from glass, plastic, or another material suitable for imaging the contents of the two chambers 104 and 124.

Central to certain embodiments of this invention is the fact that a molded or otherwise formed open channel, e.g., 106 or 107, need not be sealed at the time of fabrication of the subassembly, but the closing of the open channel to allow controlled and constrained flow of fluid in the channel is accomplished by placing the lower layer of the inner subassembly 120 in direct and uniform contact with the upper surface of the outer subassembly 100 or the upper surface of the lowermost piece of glass. This greatly minimizes the cost of fabricating each subassembly, in that there are no closed channels on any of the planar surfaces. Furthermore, this architecture allows disassembly of the layers for separate imaging, genetic, or biochemical analysis of the cells growing on each layer.

A porous membrane filter 136 is disposed under the bottom surface of the second base layer 121 and fixed to the bottom surface of the second base layer 121. The porous membrane filter 136 can be fabricated from track-etched polycarbonate, a nanofibrous mesh, 1002F photoresist, etched silicon nitride or another high-strength, thin material that could support possible pressure gradients between the two chambers 124 and 104. The diameter of the pores in the porous membrane 136 can be chosen to be below 100 or 200 nm to ensure that there can be no cell transmigration across the barrier, 200 nm to 3 μm to allow cellular processes from cells on one side of the barrier to contact cells on the other side, or 3 to 10 μm to allow extravasation and intravasation of leukocytes and metastatic cancer cells. The membranes could have a series of nanoslits were it desired to have high permeability to small molecules but not to ones larger than the slits. These membranes can be permanently attached to the base assembly 100 or could be inserted as a stand-alone item that is being sandwiched between the multiple devices as in FIG. 1E. Certain embodiments of this invention apply equally well to these and other types of barrier membranes.

A second input channel 126 and a second output channel 127 are molded or embossed, cast or otherwise machined into the lower surface of the second base layer 121, formed into the lower surface of the second base layer 121 and above the upper surface of the porous membrane filter 136, and in communication with the second central chamber 124. The second input channel 126 is located at the left side of the second base layer 121, and the second output channel 127 is located at the right side of the second base layer 121. A second input port 125 is formed in the second port block 122 located at the left side, and a second output port 128 is formed in the second port block 122 located at the right side. The second input port 125 is connected to the second input channel 126, and the second output port 128 is connected to the second output channel 127, such that the second input port 125 and the second output port 128 are communicatively connected with the second central chamber 124 via the second input channel 126 and the second output channel 127, respectively. In operation, a liquid flows into the second input port 125, passes sequentially the second input channel 126, the second center chamber 124, the second output channel 127, and flows out from the second output port 128.

Figure 1E:
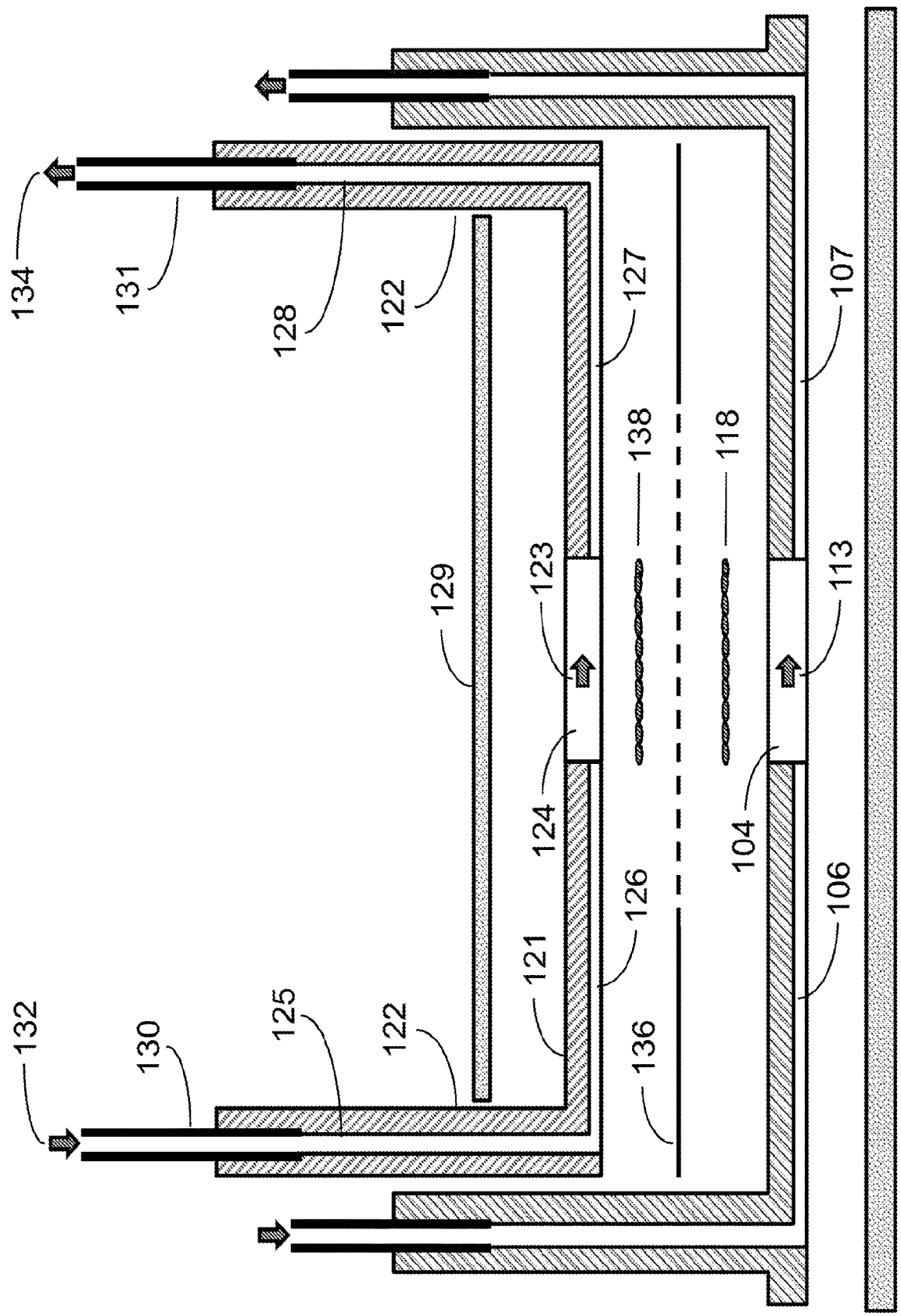
FIG. 1E is a cross-sectional exploded view of a double-layer microfluidic bioreactor according to one embodiment of the present invention, where the membrane filter layer is porous only in the central portion.

FIG. 1E is an exploded view of the first chamber assembly 100 and the second chamber assembly 120 before being assembled together. As shown in FIG. 1E, the input flow 132 enters the second input tube 130, the second input tube 130 is connected to the second input port 125, the second input port is connected to the second input channel 126, and the second input channel 126 is connected to the second central chamber 124. The fluid flow in the second central chamber 124 from the second input channel 126 to the second output channel 127 forms a second flow 123. The second flow 123 flows sequentially through the second output channel 127, the second output port 128, and out of the second output tube 131 as the output flow 134.

Figure 1F:
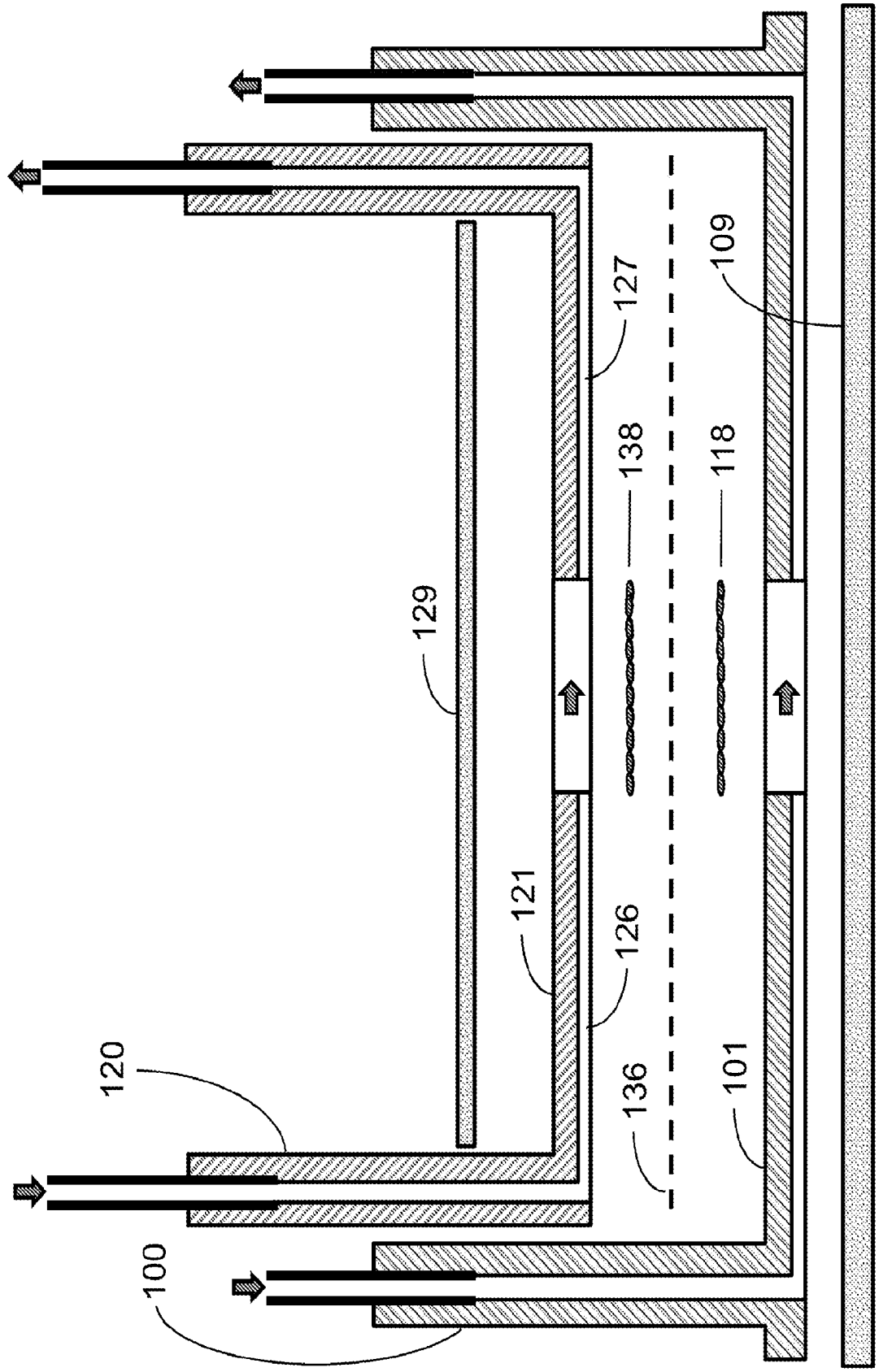
FIG. 1F is a cross-sectional exploded view of a double-layer microfluidic bioreactor according to one embodiment of the present invention, where the membrane filter layer is porous over its entire extent.

The porous membrane filter 136 separates the upper assembly 100 from the lower assembly 120, and allows chemical or cellular communication between the upper chamber 124 and the lower chamber 104. In certain embodiments, a layer of cells 118 is adhered to the lower surface of the porous membrane 136, and a layer of cells 138 is adhered to the upper surface of the porous membrane filter 136. These cells 118 and 138 could be of the same or different type or phenotype. For example, the cells 118 could be brain microvascular cells and the cells 138 could be brain astrocytes and pericytes, so that the entire system would replicate the blood-brain-barrier. The upper glass 129 seals the upper chamber 124 and allows visualization of both chambers 104 and 124. In certain embodiments, as shown in FIG. 1E, the membrane filter layer 136 is porous only in the vicinity of the chambers 104 and 124 but not on the outer regions of that layer. In other embodiments, as shown in FIG. 1F, the membrane filter layer 136 is porous over its entire extent, including under the channels 126 and 127. One key feature according to certain embodiments of this invention is that the clamping of membrane filter layer 136 between the lower base layer 101 and the upper base layer 121 obviates leaks from the channel(s), thereby simplifying manufacture and assembly of the two-layer device. As shown in FIG. 1G, a clamped, two-layer system is provided.

FIG. 2A shows extension of this concept to a multi-layer device with the same or more complex fluidic topology. The multi-layer device includes sequentially from bottom to up, a first (bottom) assembly 200, multiple middle assemblies 210 and 220, a top assembly 230, and an inner clamp 240. The first assembly 200 is equivalent to the assembly 100 in FIG. 1A. The bottom of the first assembly 200 is formed by a glass or plastic plate 209. Placed inside of the first assembly 200 is the middle assembly 210, which is equivalent to the assembly 120 shown in FIG. 1E-1G. Additional, smaller, nested assemblies shown in this example as 220 and 230, are located inside of 210. As discussed above, the sealing of the open microfluidic channels is accomplished by pressing one sub-assembly against another to form closed channels through which the flow of fluid can be directed. Topmost chamber, in subassembly 230, is sealed with an upper window 239, equivalent to 129 in FIGS. 1D-1G. Given that on objective of this invention is to create a system that can be assembled from discrete subassemblies and then disassembled, the inner clamp 240 with central opening 241 is utilized to provide compression of the flat portions of each subassembly and the membrane filters that separate them. To ensure that this pressure is applied uniformly across all horizontal surfaces, thereby sealing the microfluidic channels that they contain, an additional clamp block 250 is designed to apply a compressive force to all of the subassemblies 200, 210, 220, 230, 240, for example. Holes in this clamp 250 provide access to the various tubes from each subassembly.

Figure 2B:
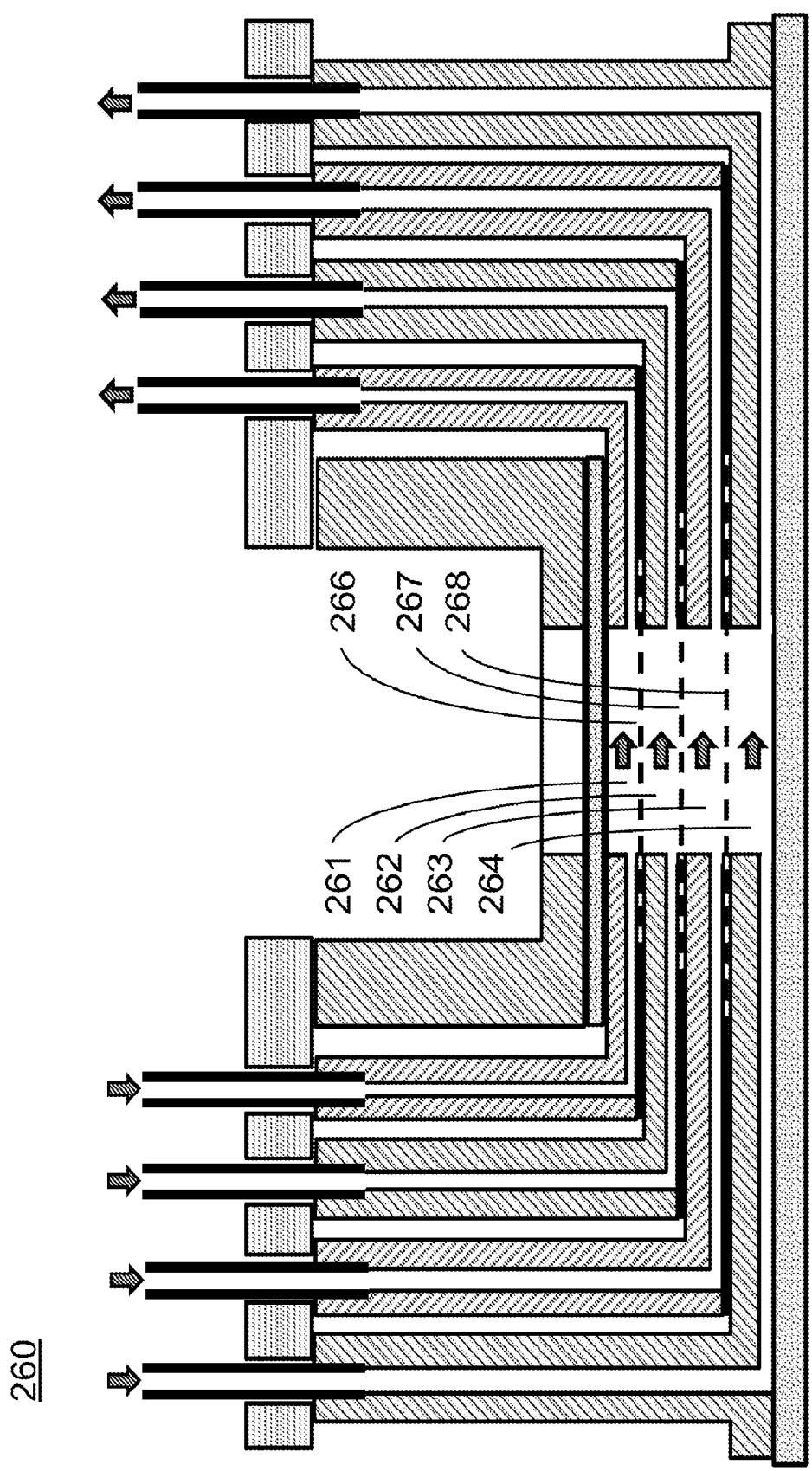
FIG. 2B is a cross-sectional assembly view of a five-layer microfluidic bioreactor according to one embodiment of the present invention.

FIG. 2B shows assembly 260 that is created when the components shown in FIG. 2A are compressed together, thereby creating four chambers 261, 262, 263, 264 that are separated by filter membranes 266, 267, and 268. This embodiment thereby allows the culture of multiple cell types on the upper and lower surfaces of each membrane. For example, 264 could recreate the vascular space of a blood brain barrier model, where the lower surface of filter 268 supports the brain microvavascular endothelial cells, and the upper surface of the filter 268 supports pericytes and astrocytes. In this case, chamber 263 would represent the brain compartment and would contain neurons, astrocytes, and other cells. Chamber 262 could represent the cerebrovascular space, and ependymal cells grown on the upper surface of filter 267 and the lower surface of filter 266 would thereby line the region that represents the brain ventricles. Finally, the endothelial cells on the upper surface of 266 could allow the uppermost chamber 261 to represent the venules that provide vascular return from the brain and entry of immune cells into the brain, or the chorid plexus that is responsible for the generation of the cerebral spinal fluid. Together, this ability to assemble and disassemble the various layers will allow study of the structure and function of complex biological system such as the vascular system of the brain. This system provides independent fluidic access to each chamber and the cells that it supports, thereby allowing closer recapitulation of physiology than would be possible with conventional, single transwell inserts. In certain embodiments, all tubes enter the subassemblies from the top. In other embodiments, the tubes enter from the bottom. Alternative, in additional embodiments, the tubes can enter from the side as long as interferences with the frames of outer layers are circumvented.

These membranes in FIGS. 2A and 2B could be fabricated as being a separate or an integral part of the device, from the same or different materials, such as spun nanofibers, track-etched polycarbonate, etched silicon carbide or alumina, 1002F photoresist, PDMS or other materials, and can have same or different porosities. The upper and lower glass or plastic windows 239 and 209, respectively, allow visualization and/or fluorescent imaging of the contents of the various chambers, limited only by the transparency of the membranes and the cells that they support. Of all the materials listed, 1002F has the greatest transparency and hence would be best for quantitative imaging of the cells in each chamber. In addition, the design of this system in the form of thin layers supported by surrounding port blocks and frames ensures that the total thickness of the system, i.e., the vertical distance between the bottom of the lowest chamber (e.g., 264) and the top of the upper chamber (e.g., 261) is minimized so as to allow all cells in the various chambers to be within the working length of high-power, high numerical aperture microscope objectives for either bright field, phase contrast, or confocal microscopic imaging. Again, as shown in FIG. 1G, either or both surfaces that define the top and bottom of each chamber can support growing cells of one or more types. The channels, ports, and tubes through each subassembly could be lined with endothelial cells to better mimic physiological vasculature and microvasculature.

Figure 3A:
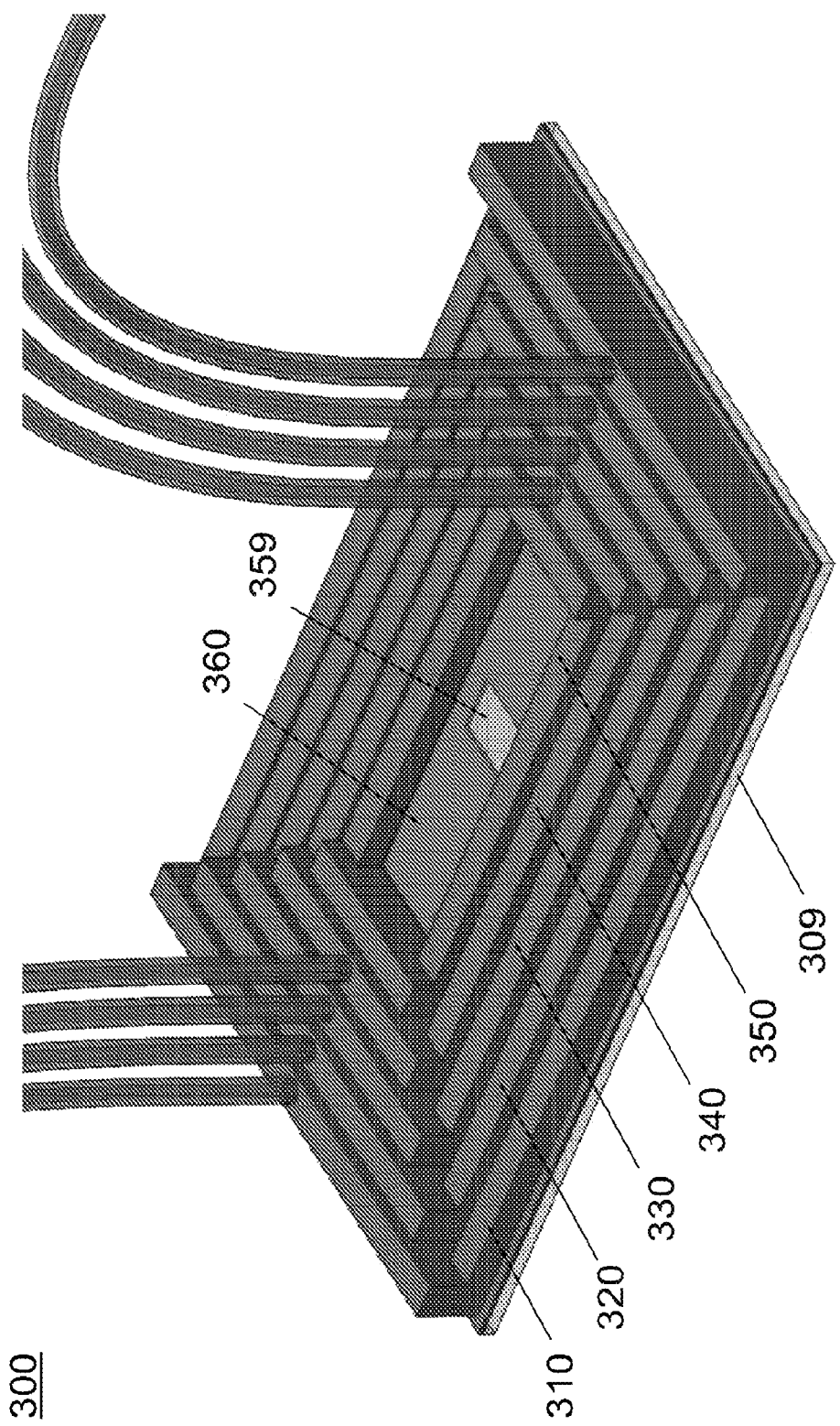
FIG. 3A is a perspective view of a 5-layer microfluidic bioreactor according to one embodiment of the present invention.

FIG. 3A shows a scaled, solid rendering of the assembly in FIG. 2B, but without the clamp 250. As shown in FIG. 3A, this assembly 300 has five stackable subassemblies (310, 320, 330, 340, and 350) that define four chambers with four inlet ports and four outlet ports, each of which could be produced by injection molding of a thermoplastic, soft lithography of PDMS, or hot embossing of thermoplastic, or direct machining of materials such as cyclic olyfin copolymer. A window on the top 359 and another window on the bottom 309 enable visualization of the contents of the four chambers. The upper surface of subassembly 350 is shown as 360, and may include a means to provide compressive force on the layers beneath.

Figure 3B:
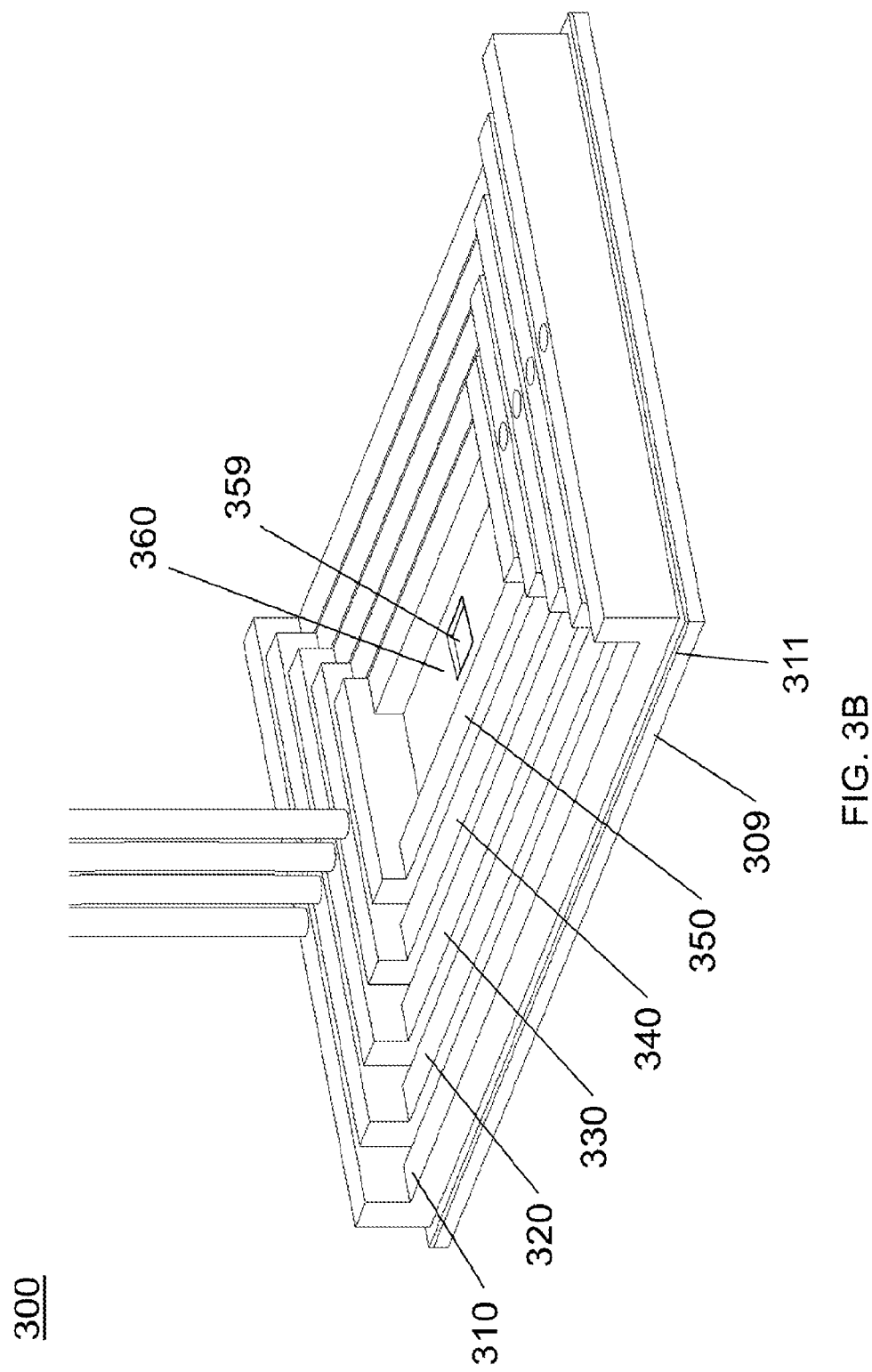
FIG. 3B is a line drawing of FIG. 3A.
Figure 3C:
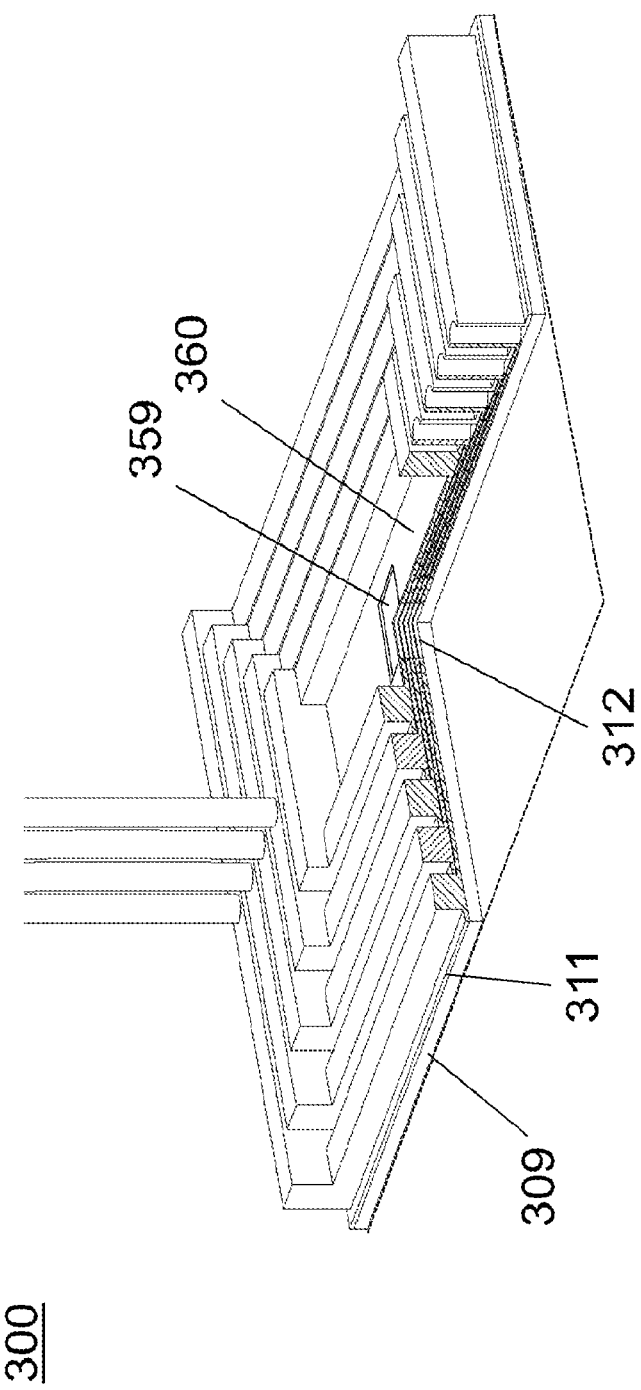
FIG. 3C is a quarter cross-section view of FIG. 3B.

FIG. 3B shows a line drawing of the same assembly 300 of FIG. 3A, where only the inlet tubes are shown for clarity. FIG. 3C shows a quarter cross-section through the assembly 300. Note that the base layer 311 of subassembly 310 is thin, as is the associated chamber 312 defined by this layer, as is required by the objective of certain embodiments of this invention to provide chambers of low height to minimize the media volume and maximize the cell to media ratio. The other base layers can have the same, smaller, or larger thicknesses as required to provide the respective chamber volumes.

Figure 3D:
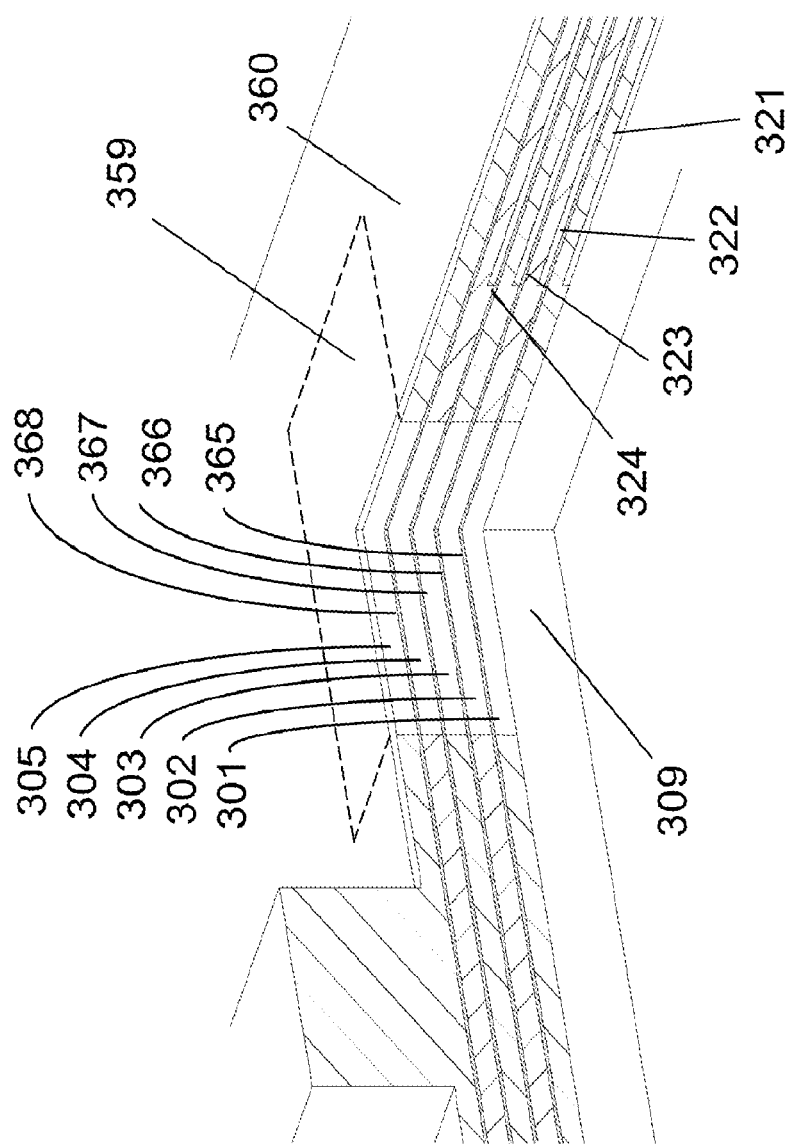
FIG. 3D is a partial enlarged view of FIG. 3C.

FIG. 3D provides a close-up of the section in the immediate vicinity of the chambers 301-304 that are perfused and a chamber 305 that is not. Chambers 301-304 are perfused by channels 321-324, shown here in partial section. These five chambers have their upper and lower surfaces defined by the lower glass or plastic layer 309, filter membranes 365-368, and the upper glass or plastic layer 360, respectively, with the window 359 allowing microscopic visualization from the top or trans-illumination for bright-field or phase-contrast viewing from below. Again, as shown in FIG. 1G, either or both surfaces that define the top and bottom of each chamber can support growing cells of one or more types. The channels as well could be lined with endothelial cells.

Figure 4A:
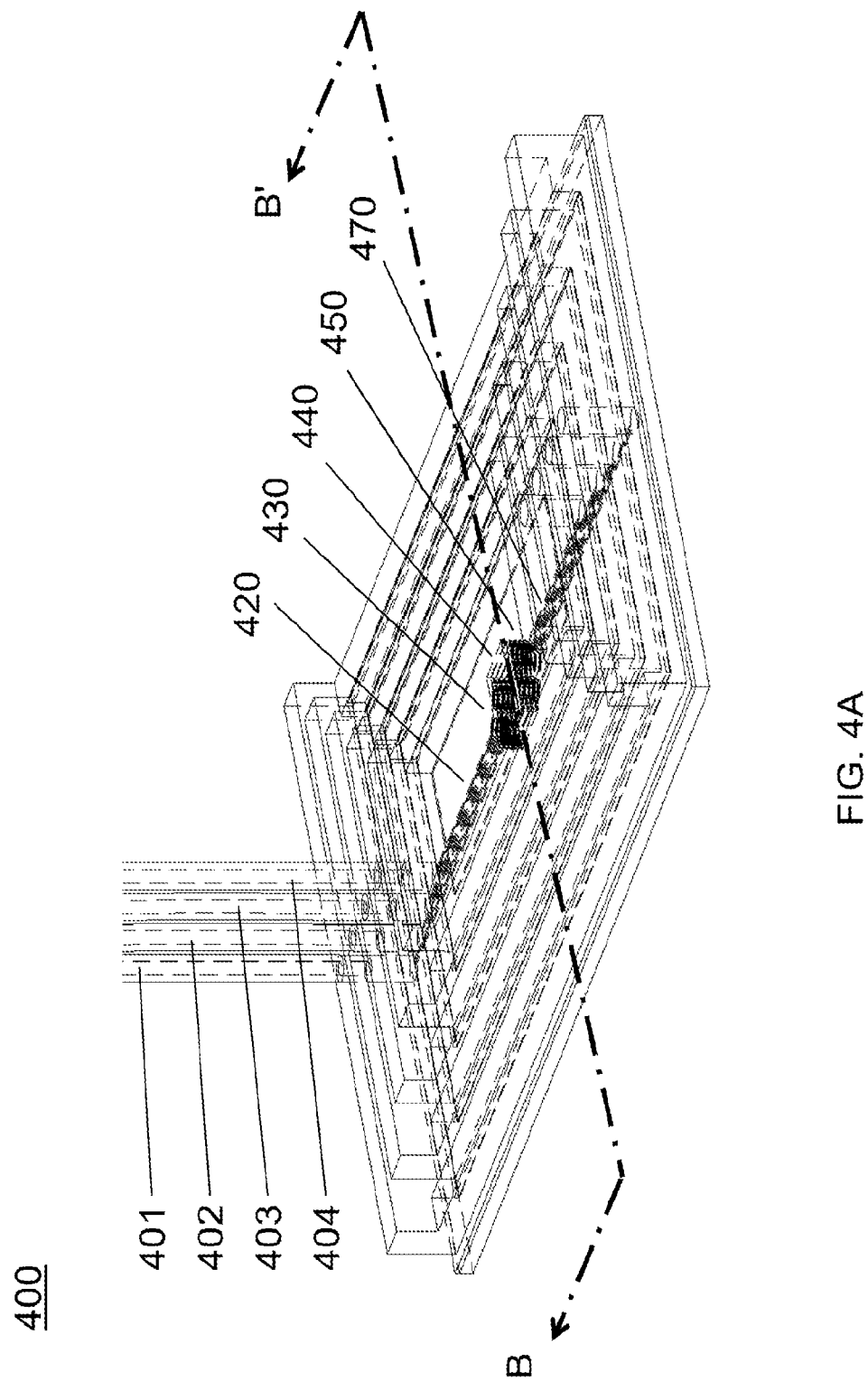
FIG. 4A is a transparent line drawing of FIG. 3A.
Figure 4B:
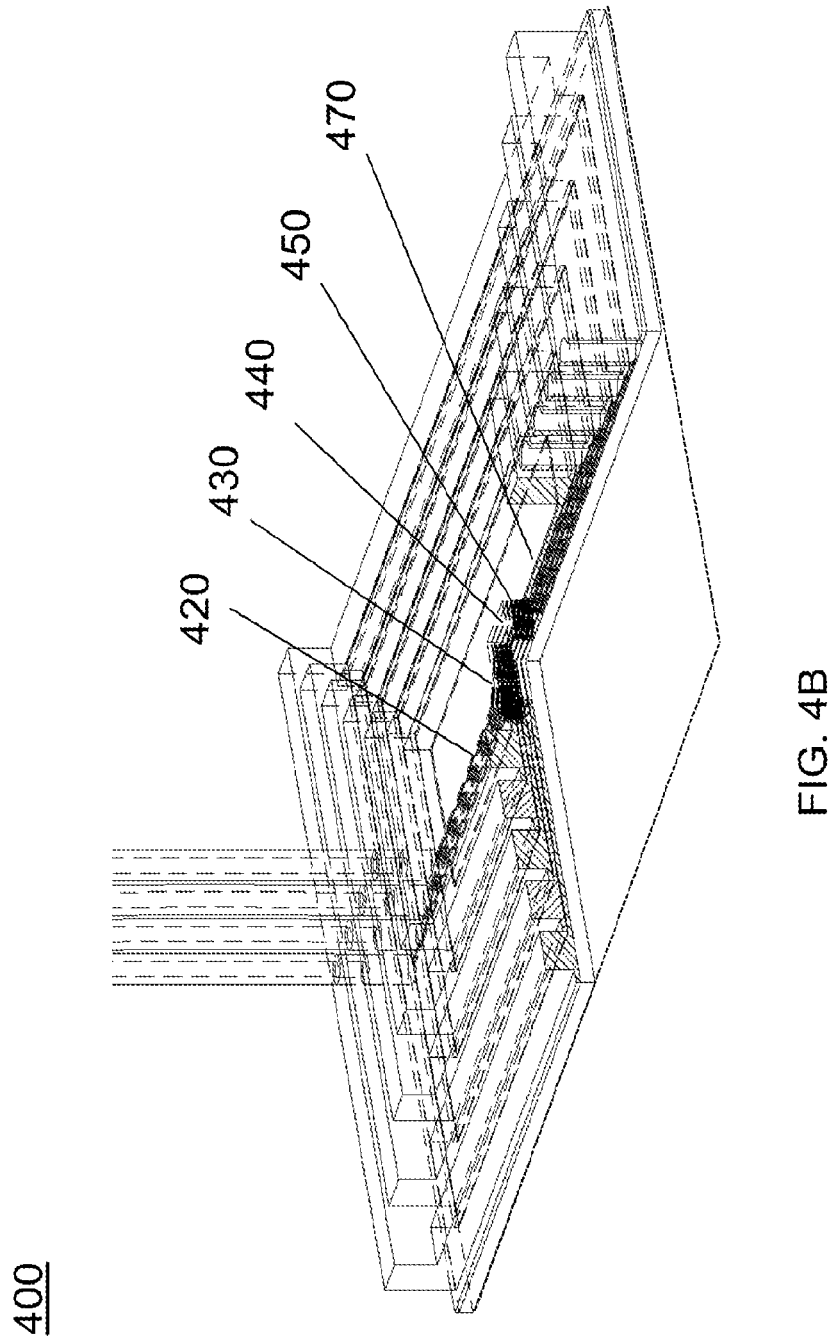
FIG. 4B is a quarter cross-section view of FIG. 4A.
Figure 4C:
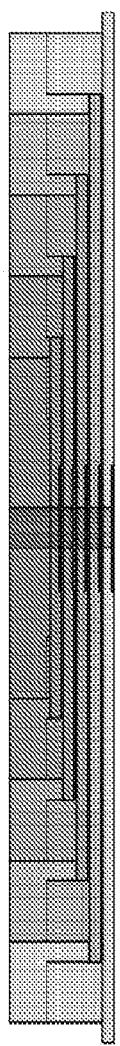
FIG. 4C is a sectional view of FIG. 4A along the B-B' direction.

FIG. 4A shows a transparent line rendering of a subassembly 400 that is equivalent to that shown in FIG. 3A. The four input tubes 401-404 are connected by ports in the integral port blocks to sets of input channels 420, and the sets of input channels 420 are connected to input networks 430 of binary splitters that in turn allow uniform perfusion of each of the chambers 440 across their entire width. The effluent is gathered by the network 450 that in turn connect to output channels 470 and the corresponding output ports and tubes (not shown). FIG. 4B shows a quarter section view of assembly 400. FIG. 4C shows a shaded cross-section of the five subassemblies in FIG. 4A and FIG. 4B.

Figure 5A:
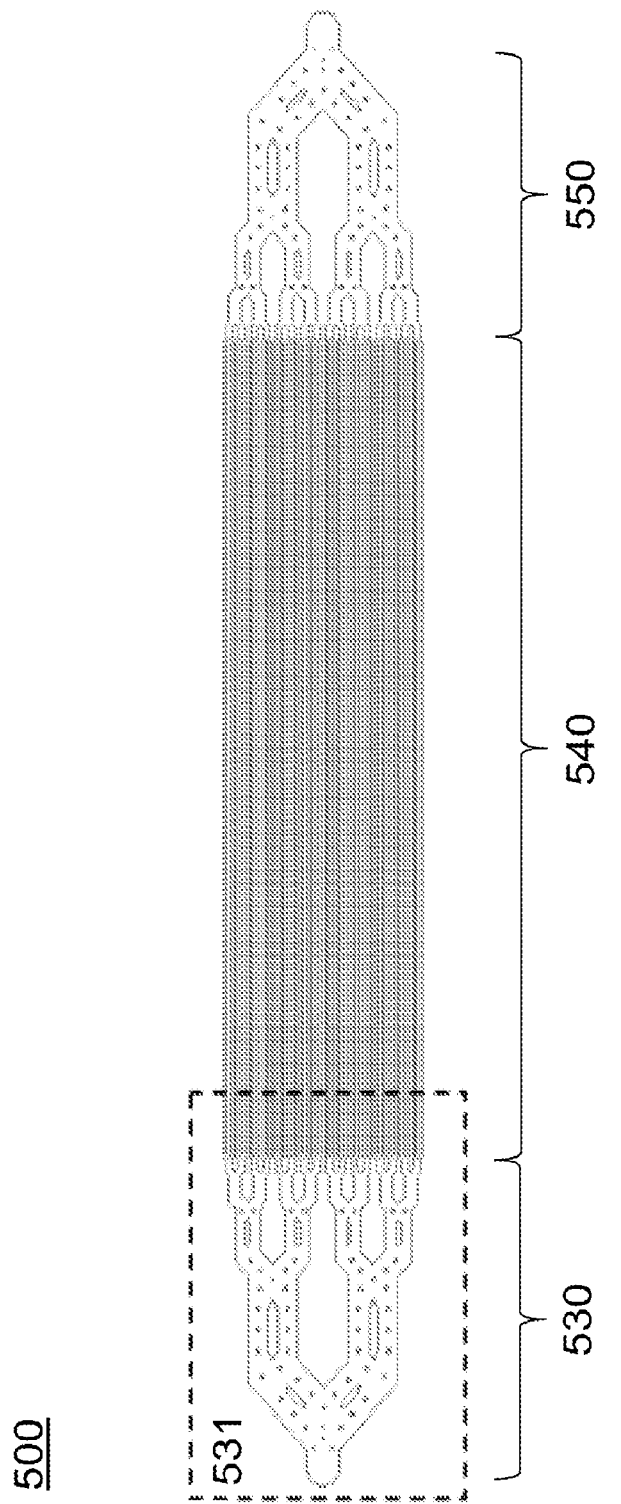
FIG. 5A schematically shows the channel outlines for an input splitter according to one embodiment of the present invention.

The microfluidic channels and splitters 430 and 450 in FIG. 4B can be fabricated in a number of different manners. Rather than casting a monolithic fluidic subassembly 100, as shown in FIGS. 1A-C, with single channels 106 and 107 connect to the central chamber 104, FIG. 5A shows another embodiment where the input channels in a single monolithic microfluidic subassembly 500 are split in a binary or other fashion before connecting to the chamber. FIG. 5A, shows the channel outlines for an input splitter 530, with four levels of binary division that produce $2^4$ (16) channels 540 that then are rejoined with the binary combiner 550.

Figure 5B:
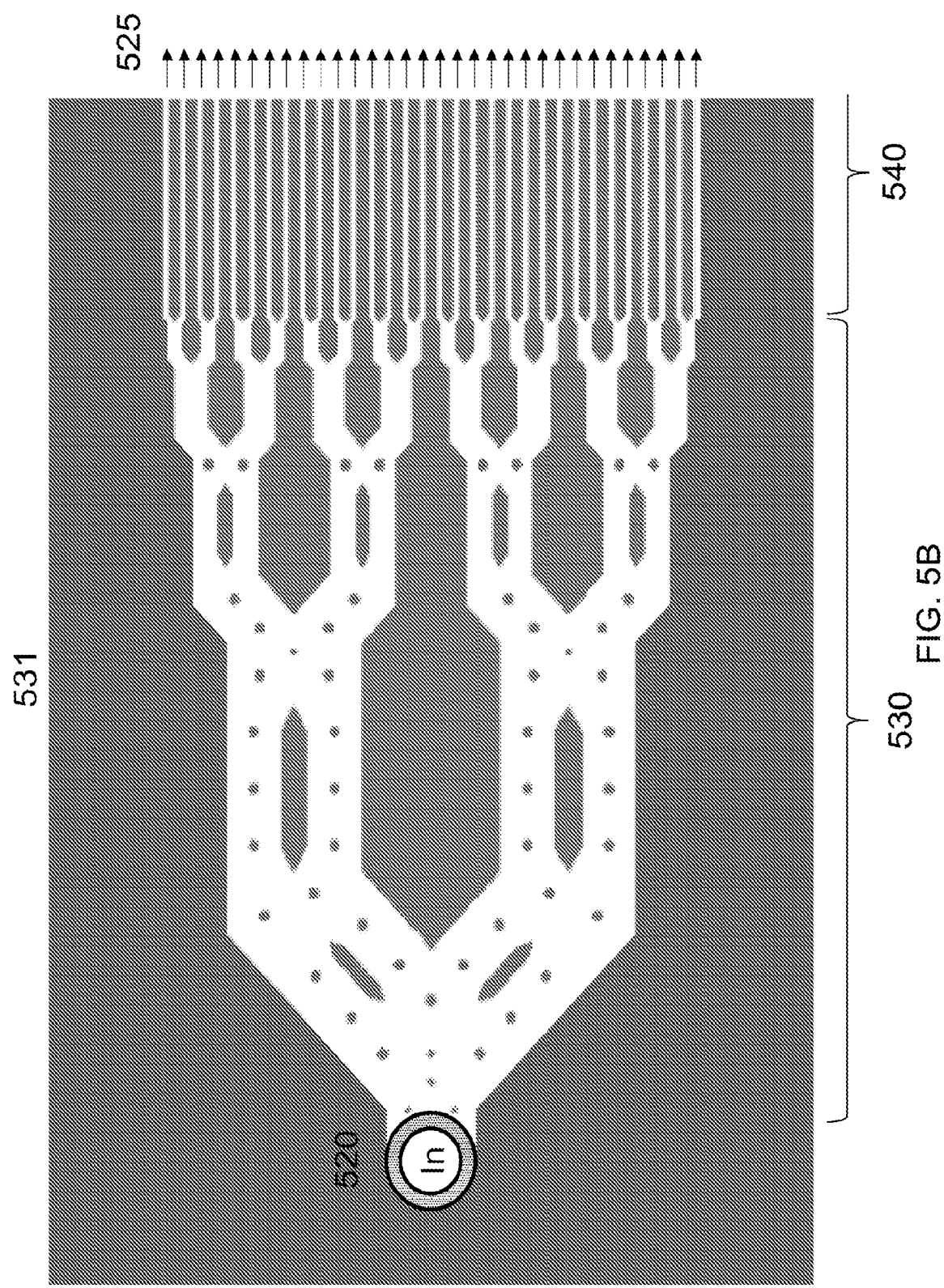
FIG. 5B is a partial enlarged view of FIG. 5A.

FIG. 5B shows an enlargement of the input region 531 of 500, where grey corresponds to the bulk of the device in which the white channels are cast, injection molded, machined, or hot embossed using appropriate molds or other devices. The input tube 520 connects to the input splitter 530 by a port cast or punched into the port block, as shown in FIG. 1A. The uniform flows from the 16 outputs of the input splitter are labeled 525. Different splitting geometries can produce other flows. The use of two or more input ports and gradient mixers could produce a gradient in either flow rate or concentration.

Figure 5C:
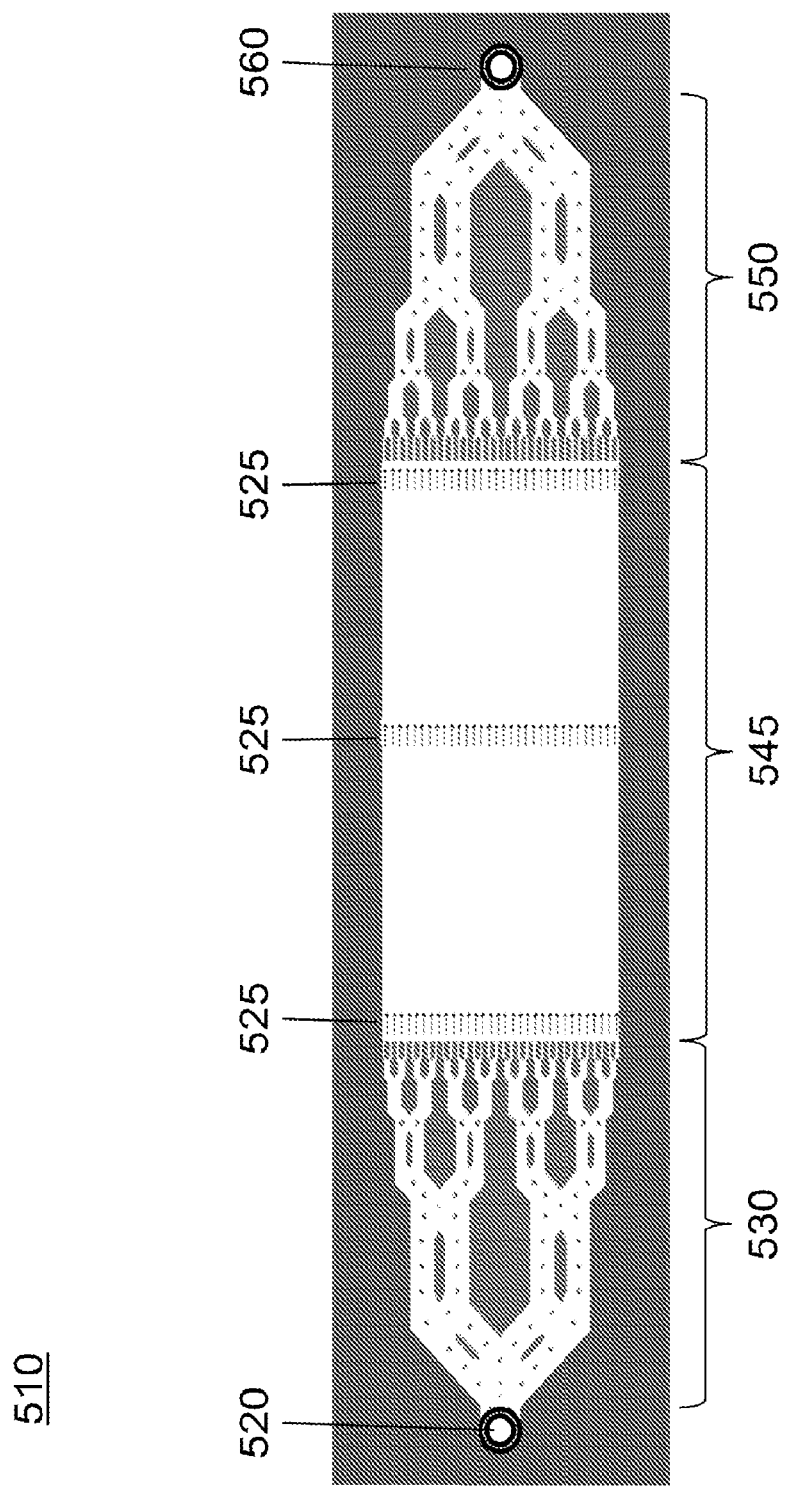
FIG. 5C shows a variant subassembly of FIG. 5A, where the central region is a single chamber.

FIG. 5C shows a variant subassembly 510 where the central region 545 is a single chamber in contrast to the parallel channels 540 in FIGS. 5A-B. Note that the uniform flow 525 occurs across the length of the chamber. The flow from the chamber then enters the binary combiner 560 which in turn is connected to the output port and tube 560.

Figure 5D:
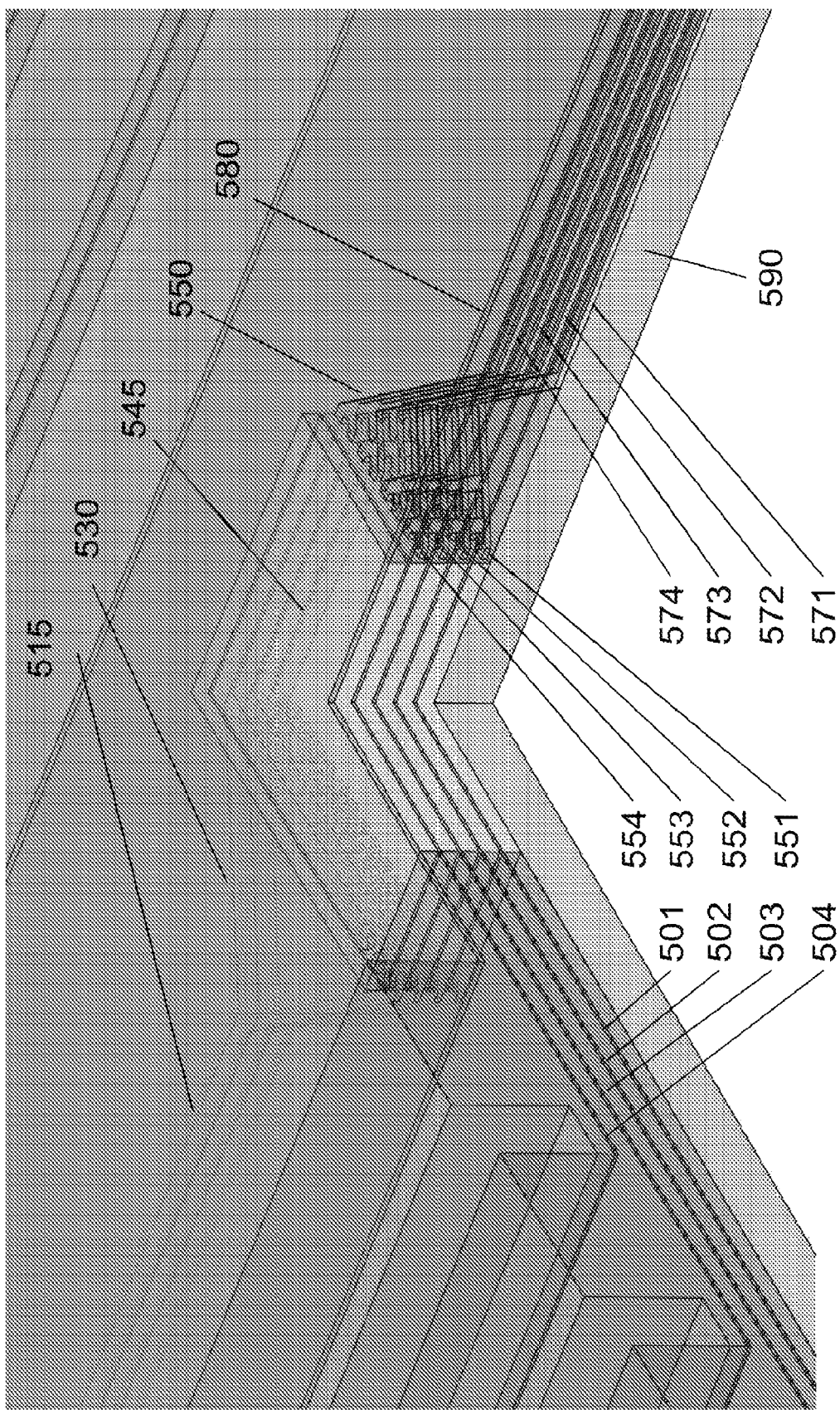
FIG. 5D shows a transparent rendering of the central region of an assembly that has multiple layered subassemblies according to one embodiment of the present invention.

FIG. 5D shows a transparent rendering of the central region of the assembly 500 that has multiple layered subassemblies with input ports 515, input binary splitters 530, chambers 545, output binary combiners 550 (also shown individually as 551-554), and output channels 571-574. The lower and upper windows that seal the stack of chambers are 590 and 580, respectively. The membranes between the chambers are 501-504 as discussed previously.

Figure 5E:
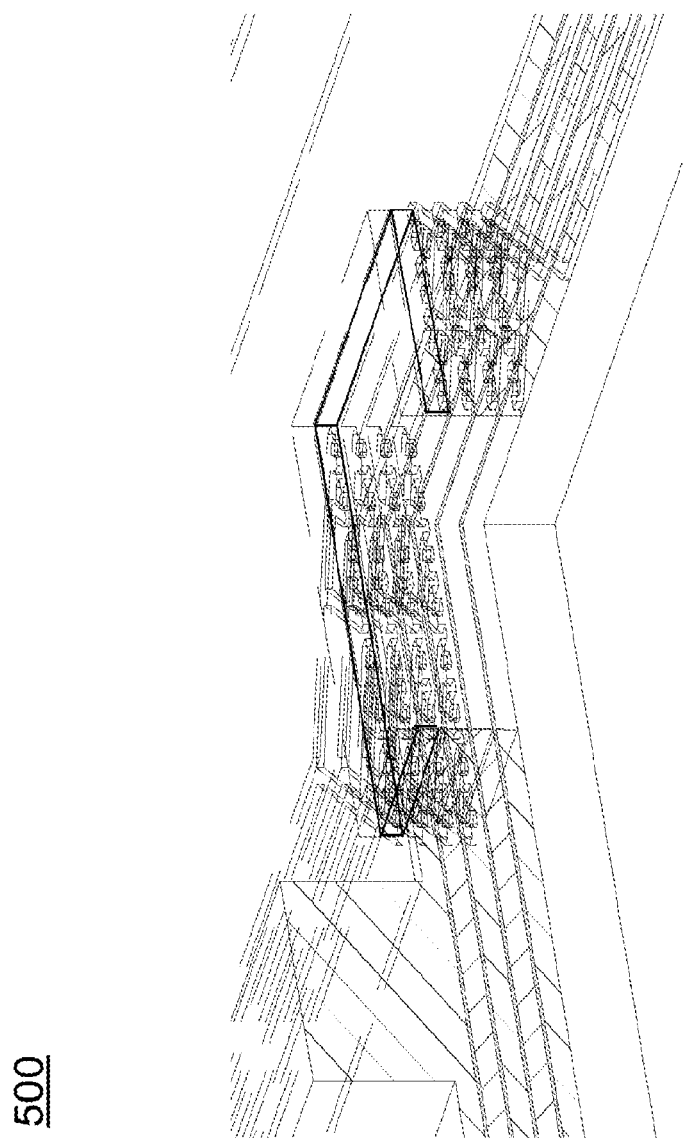
FIG. 5E is a transparent partial line drawing of FIG. 5D.

FIG. 5E is a transparent line drawing that indicates the complexity of the central features that comprise assembly 500, with a single chamber outlined with a darker line. Note that this complexity is straightforward to obtain by the stacking of individual subassemblies that are simpler to conceive and easier to fabricate.

It is important to recognize that the flow in these assemblies could be in either direction, and a variety of other splitter, combiner, and other fluidic topologies could be implemented with this approach, including those where the flow is induced in the vertical dimension between stacked devices across the separating membrane by differing pressures in adjacent chambers. All subassemblies need not have the same flow patterns.

In the above description, stackable, multi-layer bioreactors are created where the ratio of media volume to cell volume could be minimized so as to avoid dilution of paracrine, autocrine, endocrine factors and other secreted compounds and metabolites. In typical cell culture on plastic, the depth of media above a cultured monolayer of cells may be hundreds to a thousand times greater than the thickness of the cell layer. The devices in FIGS. 1A-5E are designed to address this problem, and to allow different cell types to be cultured in close proximity so that there can be biochemical interactions of the separate cell populations.

Figure 6A:
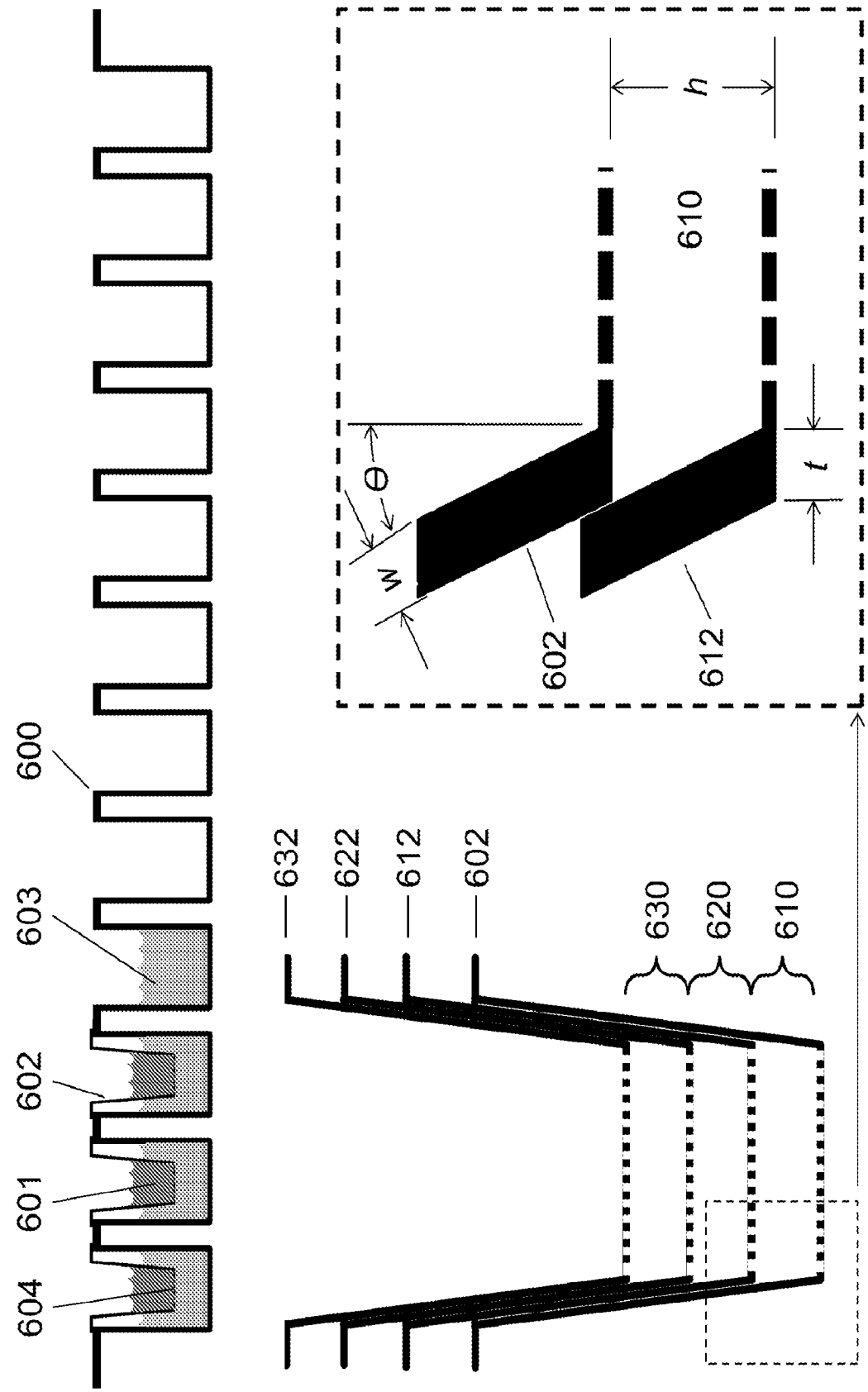
FIG. 6A is a sectional view of a transwell insert in a row of wells in a well plate.

Further, one of the most common means to grow cells that are exposed to two different environments at the same time or different cell types in close proximity is the transwell insert 602 shown in FIG. 6A that is inserted into a well plate 600 that contains culture media or other fluids 603. The barrier formed by the porous bottom of the insert 604 separates cells grown on the upper surface of 604, for example astrocytes and pericytes, from those grown on the lower surface, for example endothelial cells, as could be done to create a model of the blood-brain barrier. The difficulty with this approach is the large volumes of fluid 601 and 603 on both sides of the membrane 604. In addition, the conventional transwell plate allows for only a single insert. Were one to stack inserts 602, 612, 622, and 632 with the same diameter, the angle of the sides $\Theta$ and the thickness of the insert wall w would determine the height and hence the volume of the chambers 610, 620 and 630 by the formula $w = t \cos \Theta$, where $t = h \tan \Theta$. If the desired height of each chamber is 100 μm, then the thickness w would be given by the following table

| $\Theta$, deg | h, μm | t, μm | w, μm |
|---|---|---|---|
| 5 | 100 | 9 | 9 |
| 10 | 100 | 18 | 17 |
| 45 | 100 | 100 | 71 |
| 80 | 100 | 567 | 98 |
| 85 | 100 | 1143 | 100 |

One can reasonably conclude that the injection molding of nesting transwell inserts with wall thicknesses of 100 μm or less would be impractical.

Figure 6B:
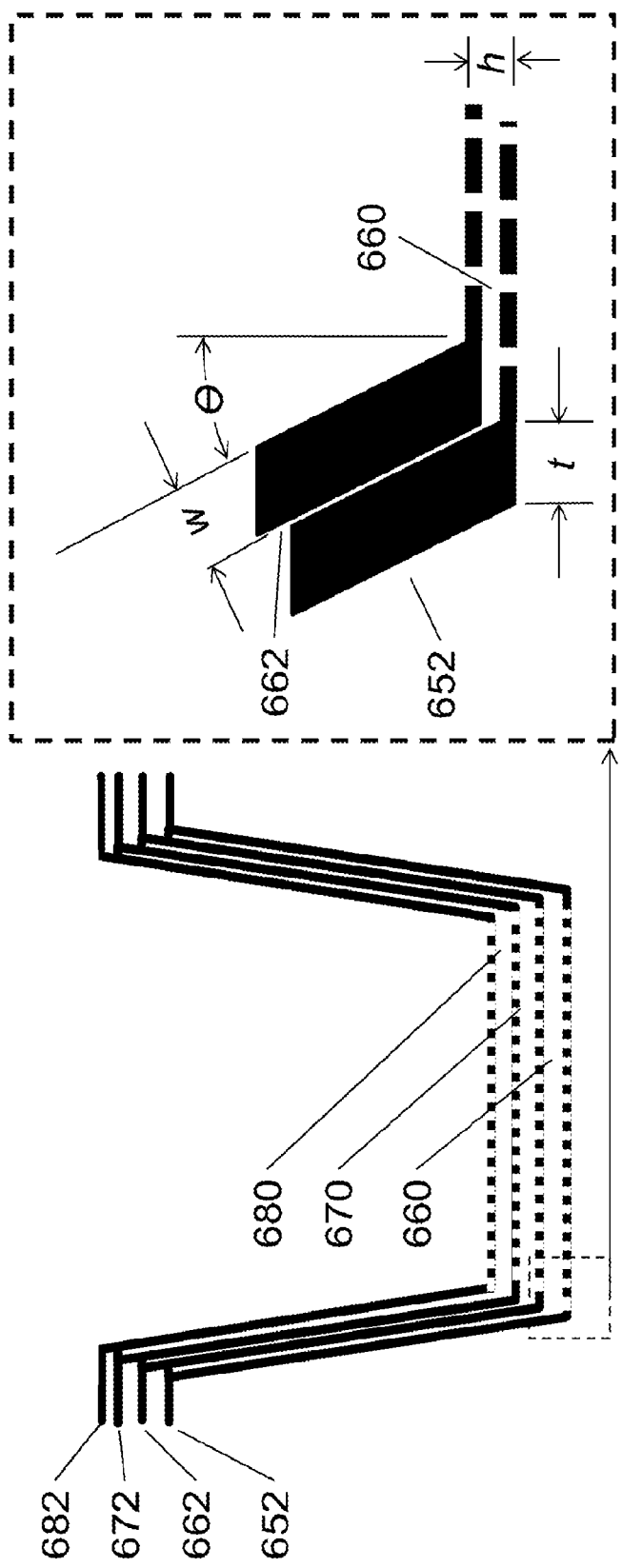
FIG. 6B is a sectional view of stacked transwell inserts according to one embodiment of the present invention.

In certain aspect, to solve the above problem, the present invention provides a multichamber bioreactor comprising stacked of multiple transwell inserts. In certain embodiments, as shown in FIG. 6B, a multi-chamber transwell nesting insert system having inserts of differing diameters are provided, where inserts 652, 662, 672, and 682 define chamber volumes 660, 670, and 680.

Figure 6C:
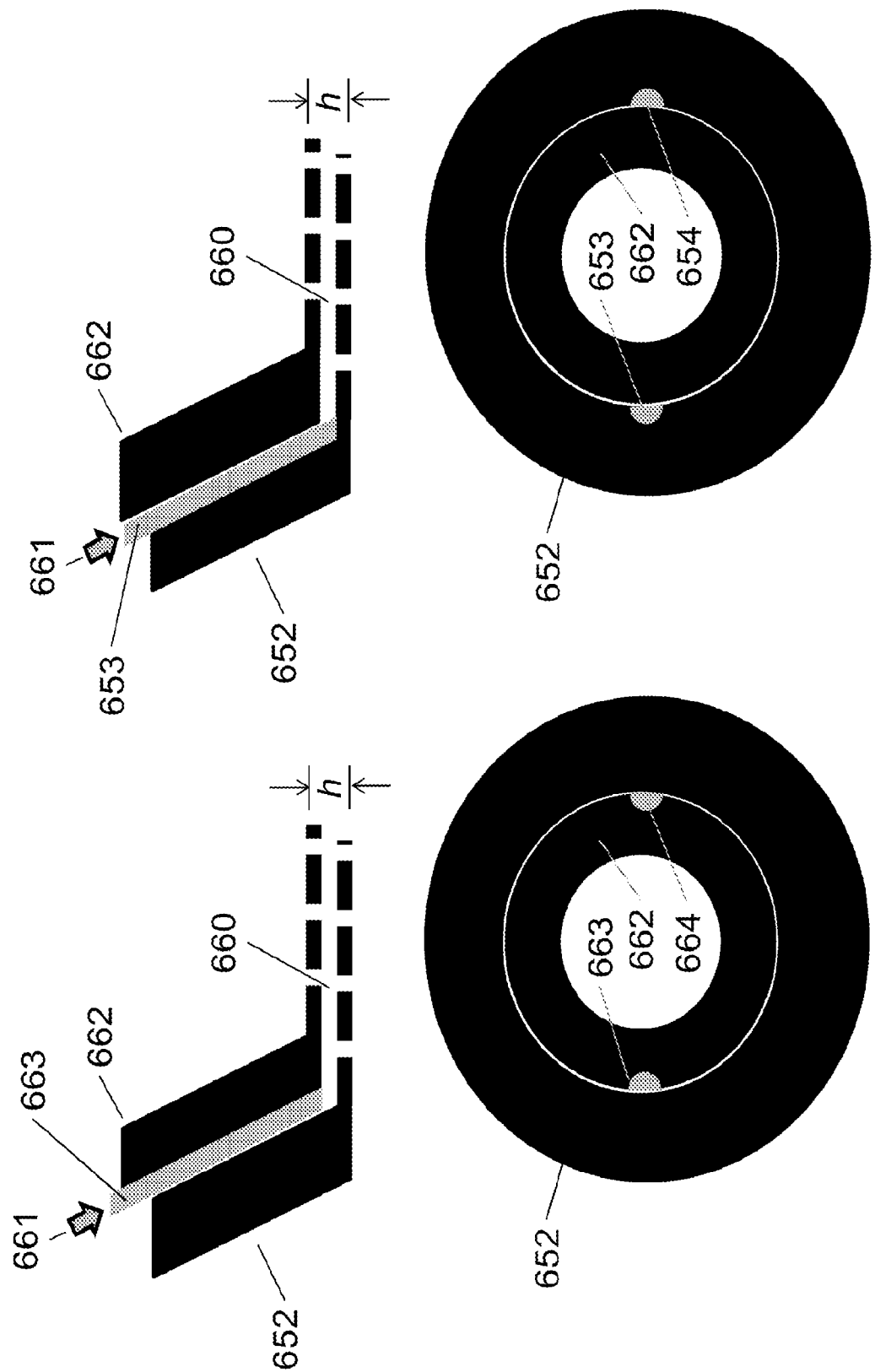
FIG. 6C shows the fluidic channels of stacked transwell inserts according to one embodiment of the present invention.

As shown in FIG. 6C, this embodiment addresses the complexity of molding an enclosed tube within the wall of a deep transwell insert by molding an open input channel 663 and an open output channel 664 into the outer surface of an inner insert 662, or a similar open input channel 653 and output channel 654 in the inner surface of outer insert 652. If the taper of the outer surface of the inner insert 662 matches that of the inner surface of the outer insert 652, the mating surfaces seal the channels against leakage and allow delivery of fluid to the chamber 660 and its removal.

Figure 6D:
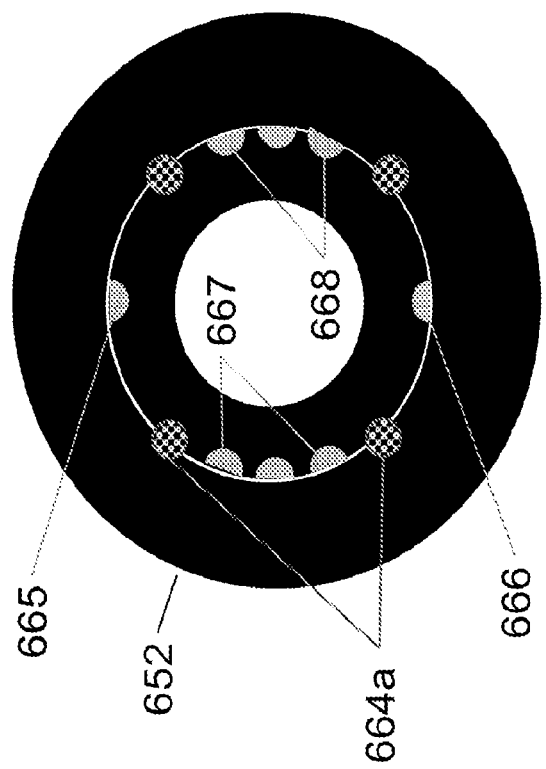
FIG. 6D shows the fluidic channels and gaskets of stacked transwell inserts according to another embodiment of the present invention.
Figure 6D:
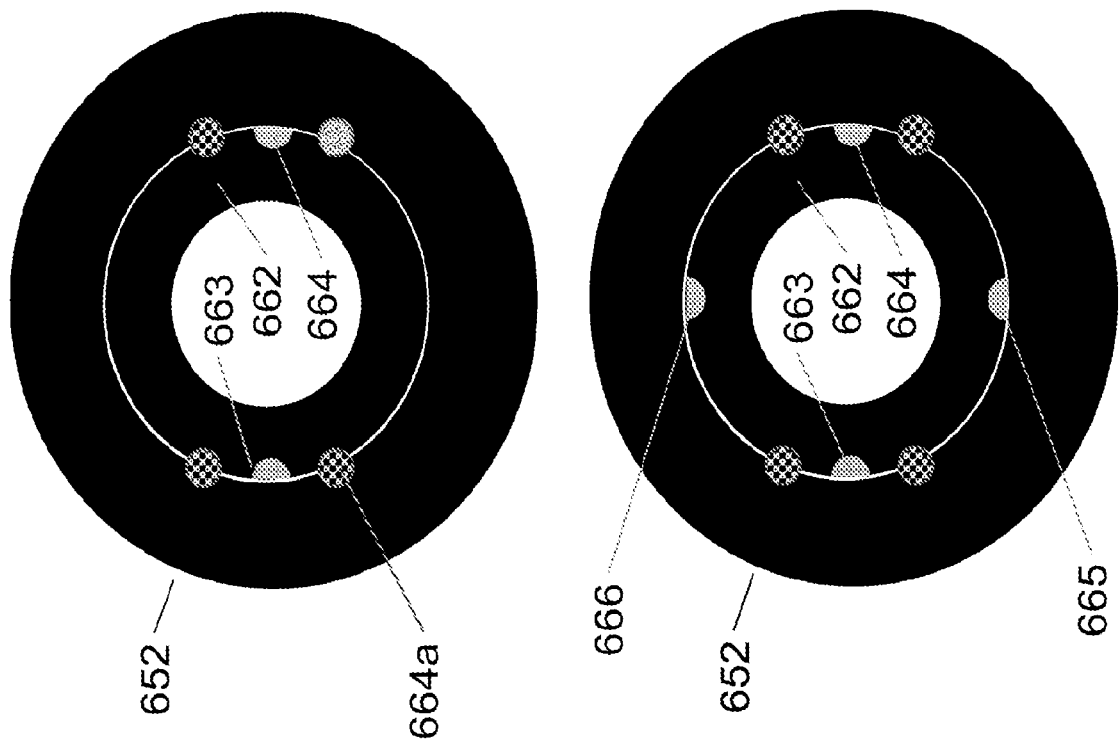

FIG. 6D shows the addition of four matching channels in both inserts 652 and 662 to support elastomer gaskets 664a that would minimize the need for a tight fit between insert surfaces for sealing, the use of orthogonal supply 665 and withdrawal 666 channels to allow the loading of the chamber with collagen or cells that might otherwise clog the channels required to perfuse the cells, and multiple input 667 and output 668 perfusion channels to provide a more uniform flow of fluid across the chamber defined by the two inserts, and hence more uniform shear forces to the cells adjacent to the flow. Given the flexibility of the location and choice of surface(s) in which to form the channels, this approach has great value to allow perfusion of multiple chambers formed by nested transwell inserts without the need of creating transwells that have enclosed tubes molded within the walls of the insert.

Figure 6F:
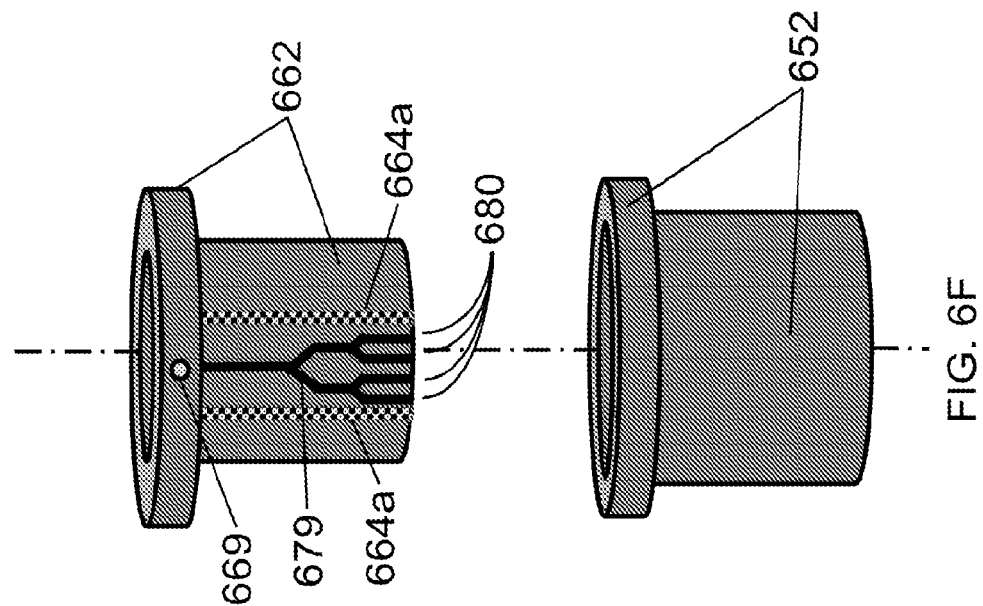
FIG. 6F shows how a single channel in the insert in FIG. 6D can replace the multiple channels in FIG. 6E.
Figure 6E:
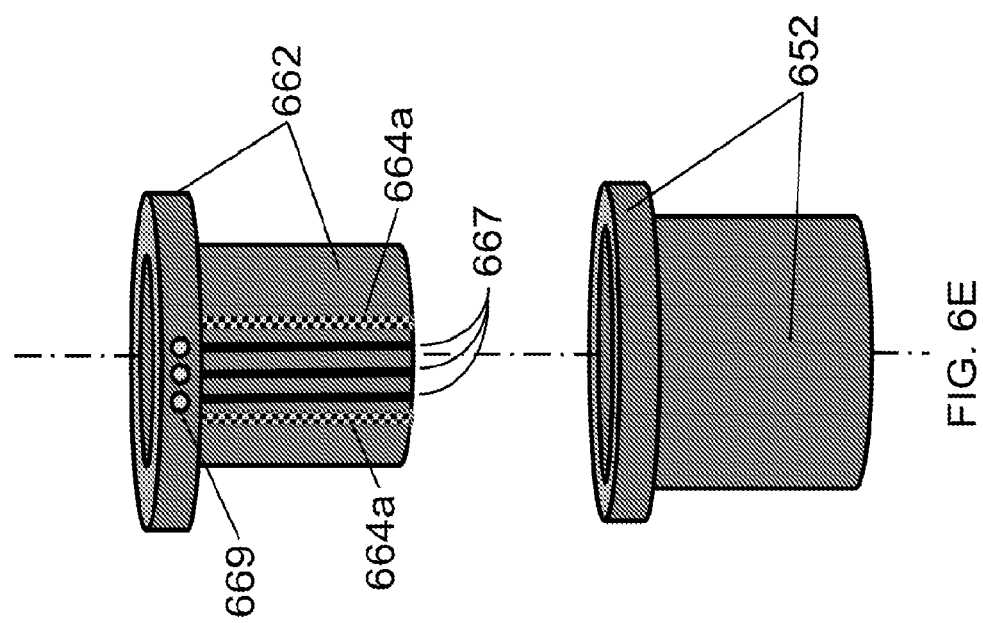
FIG. 6E shows the channels and gaskets on the outside of transwell insert in FIG. 6D.

FIG. 6E shows the exterior surface of insert 662, which slides inside of the larger insert 652. The channels 667 in the sides of 662 connect to ports 669 on the flange of 662. Gaskets 664 reduce the possibility of leakage away from the ports. FIG. 6F shows another embodiment in which the channels 680 in the side of 662 are connected to a binary splitter 679 and then a single flange port 664.

Figure 6G:
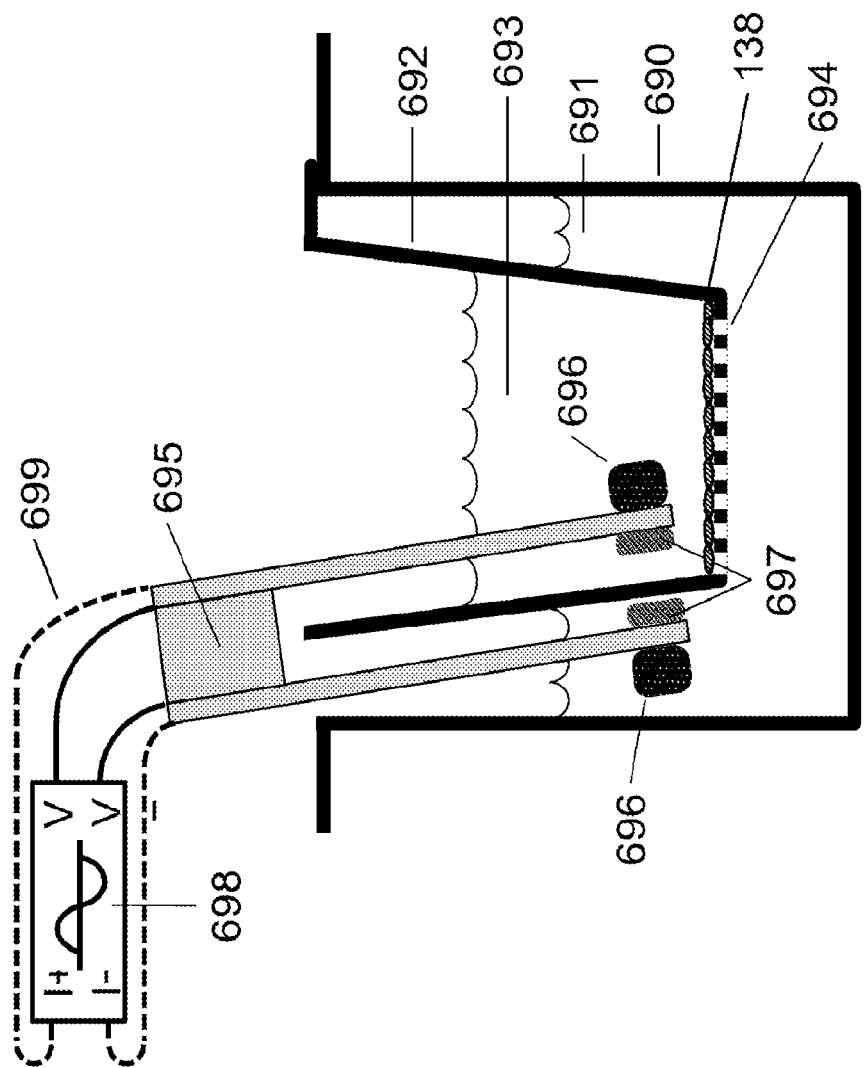
FIG. 6G shows how a conventional "chop-stick" four-electrode pair and a device to measure electrical resistance can be used to determine the transendothelial electrical resistance (TEER) of cells growing on the barrier membrane of a transwell insert.

FIG. 6G shows an instrument that measures the transendothelial electrical resistance (TEER) of a layer of cells growing on the filter at the bottom of transwell insert 694 that is within the well 690. The height of the fluid 693 in the insert need not be the same as the height of the fluid 691 in the well. 695 is a "Chopstick Electrode Set" for example from the WPI EVOM2 TEER instrument. Two electrodes 696 on the outside of the chopstick deliver current to the fluids, driven by the DC or AC current source in the TEER instrument 698. Voltage electrodes 697 on the inside of the chopstick allow the electronic instrument 698, connected to the electrodes by wires 699, to measure the DC or AC voltage that results as the current passes through the electrical resistance of the cell layer 138. A major limitation of this instrument is that the well plate that contains the transwell inserts has to be removed from the incubator, the well-plate lid removed, and the chopstick electrode inserted into each of the wells. This is time consuming and exposes the cells in the transwells and well plates to temperature changes and significant risk of microbial contamination. One aspect of this invention addresses these limitations.

Figure 7A:
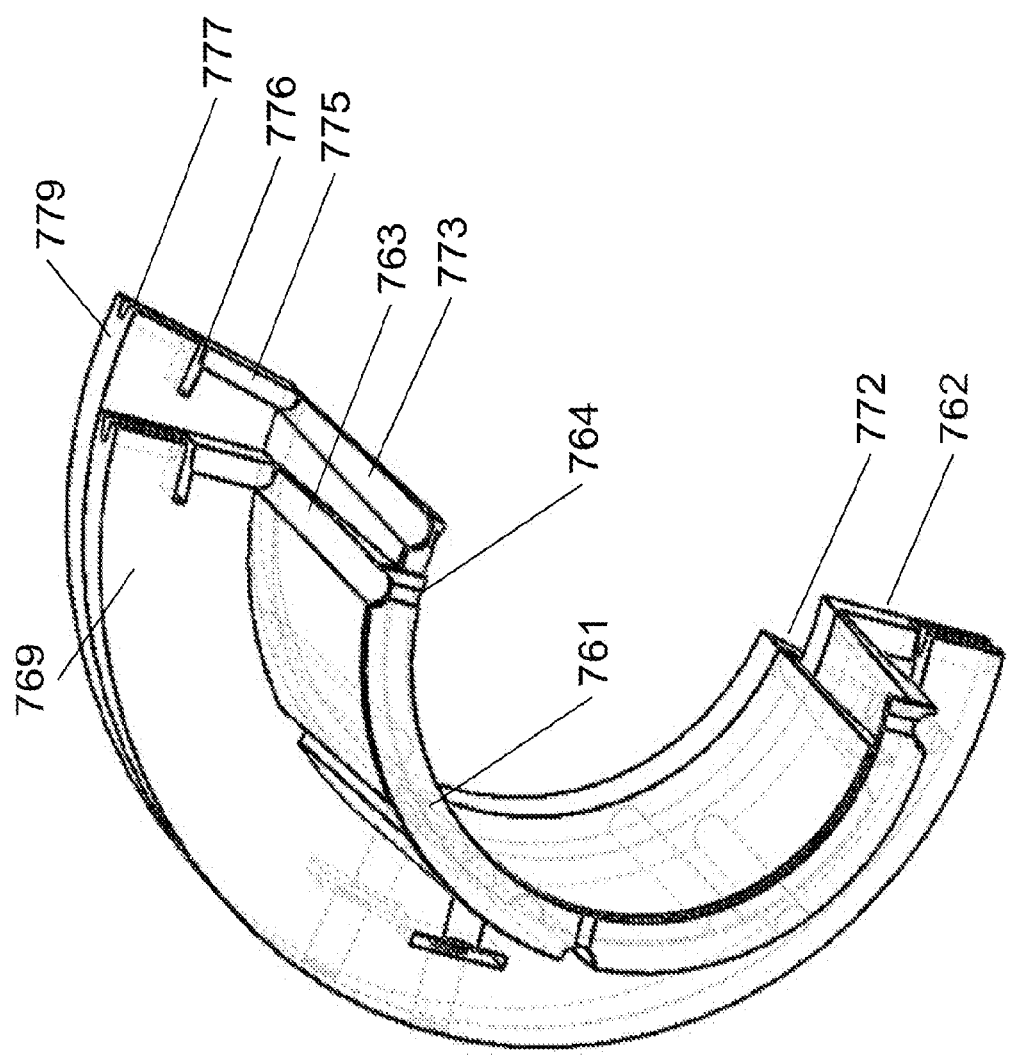
FIG. 7A is a perspective view of a pair of stacked transwell inserts according to one embodiment of the present invention.
Figure 7C:
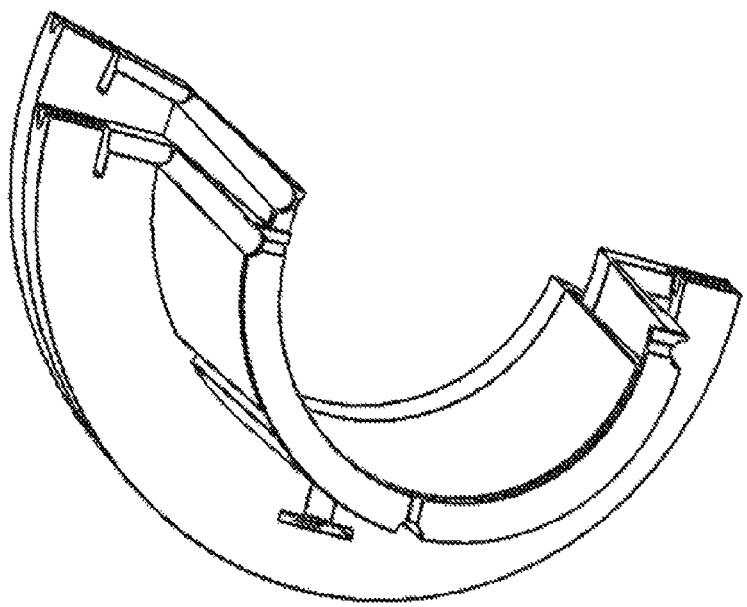
FIGS. 7B-D provide other views of the stacked transwell inserts of FIG. 7A.
Figure 7B:
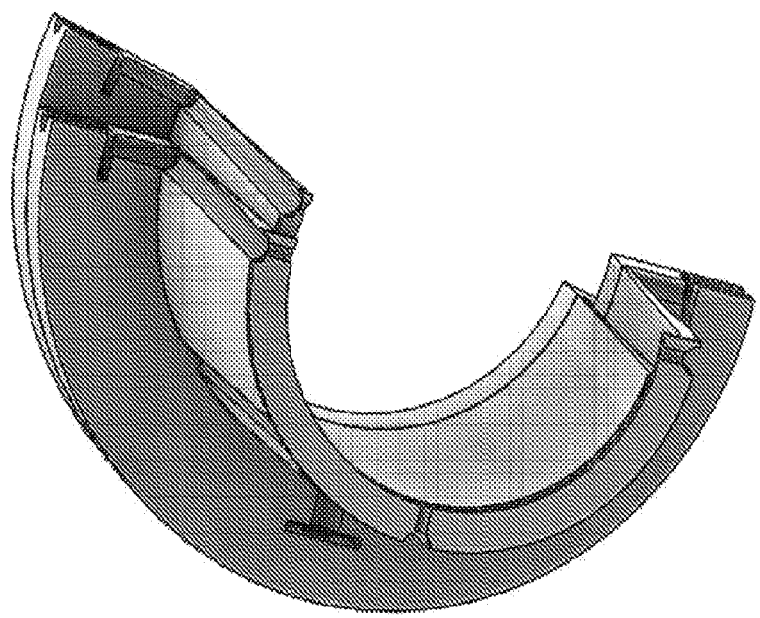
Figure 7D:
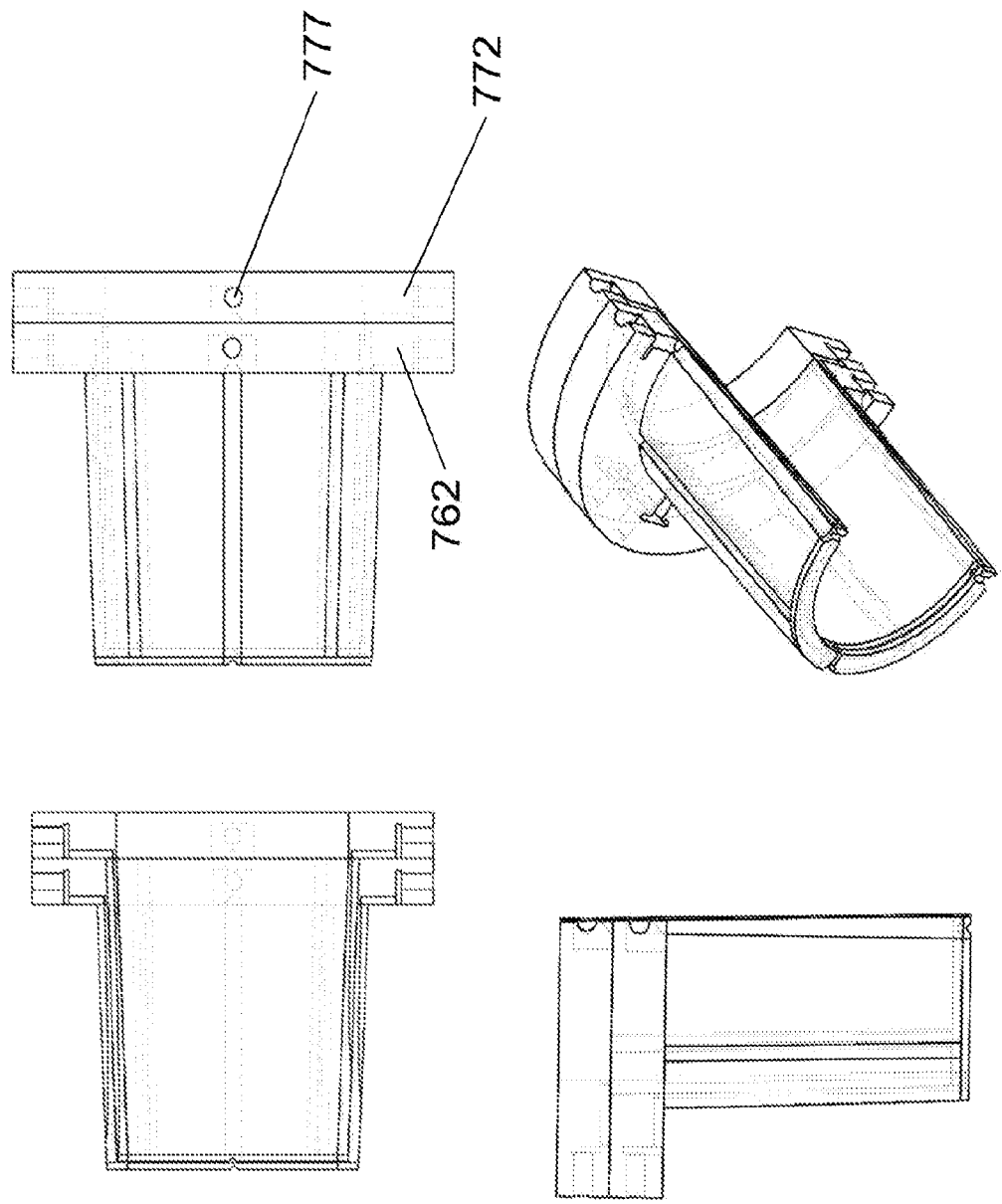

FIG. 7A is a 3D rendering with dotted lines shown of how the nested transwell inserts in FIG. 6C could be fabricated. FIG. 7A shows two inner inserts, 762 and 772, with 772 inside of 762. The vertical channels shown in FIG. 7A are 763 and 764. In addition, there are short radial channels, such as 764, that allow flow down 763 to be able to enter the chamber above the filter that would be bonded to the lowermost surface 761 of the insert 762. The insert 772 has a top flange 779 and the insert 762 has a top flange 769. The thickness of these flanges must be sufficient to allow the connection of tubing to the drilled or molded port 777 that connects to the inner channel 773 by means of an upper radial channel 775. To simplify making the fluidic connection between 779 and 775, a notch 776 is molded into the lower surface of flange 779 to allow the port to be in the middle of the thickness of the flange while the channel 775 can be on the lower surface of 779. FIGS. 7B-D provide other views of the two-insert assembly. Note that were this to be used, a third insert outside the first two would be required to seal the channels in the outer insert 762. A gasket or a tight fit will prevents leaks between the flanges 769 and 779.

In the above embodiment, the tubing ports are drawn as radial in the upper flange, but they could have a variety of orientations, including vertical, as long as measures such as notches or differing diameters were taken to avoid interferences between the tubes for the different inserts.

Since the flanges must be thick enough to provide tubing ports, possibly on the order of a millimeter or two or more, the different inserts must have different total heights to ensure that the top flanges are in contact while the bottom chambers, formed by the contacting surfaces at the bottom of the insert pairs, are of the desired height, typically of the order of 100 μm. In certain embodiments, the height of the chambers is in a range of about 50-150 μm.

Note that gaskets with appropriate holes or channels supporting appropriately shaped O-rings can be placed between the flanges of adjacent inserts to eliminate leakage of the channels in one flange that are closed by the surface of the adjacent flange. The gaskets could also be in the form of deformable viscous materials or materials whose stiffness may change as a function of temperature to simplify disassembly of the individual subassemblies at the end of an experiment.

Spacer disks with large central holes could be placed between the inserts at the bottom to ensure proper heights between the bottom of each insert, but with proper machining tolerances, this will not be required.

Figure 8A:
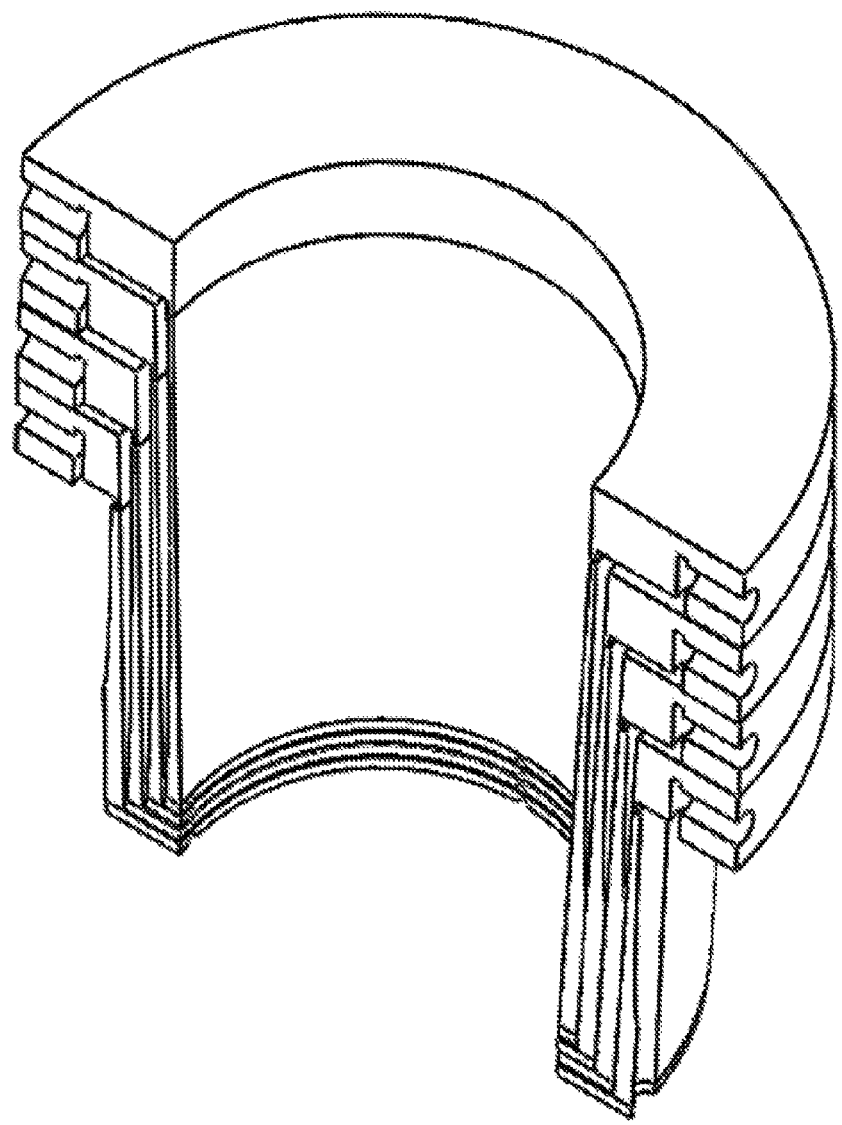
FIG. 8A is a perspective view of four nested transwell inserts according to one embodiment of the present invention.
Figure 8B:
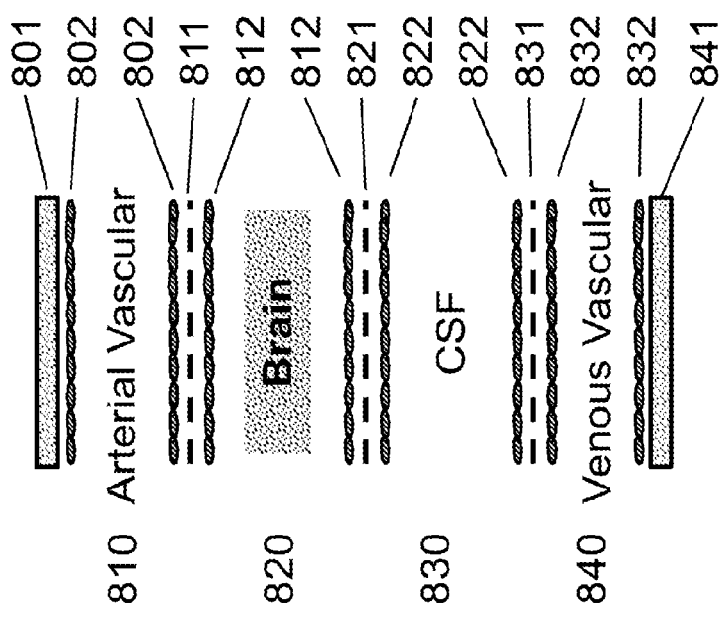
FIG. 8B schematically shows different type of cells seeded on the chamber surfaces according to one embodiment of the present invention.

FIG. 8A shows four nested inserts, also without the outer, channel-less insert that seals the open channels in the outermost insert shown. A complete assembly with lower and upper windows could readily create four adjacent compartments that are interconnected by means of the filters between each layer. FIG. 8B shows how the cells would be seeded on the chamber surfaces. The uppermost and lowermost surfaces 801 and 841 are glass or transparent plastic. The upper chamber 810, in this example, serves as the arterial microvasculature and is lined with brain microvascular endothelial cells 802. The next chamber 820 is the brain compartment that is lined with astrocytes and pericytes and filled with neurons, astrocytes, collagen or other extracellular matrix materials. Chambers 810 and 820 are separated by filter 811. The CSF chamber 830 is separated from the brain chamber 820 by filter 821, and is lined with ependymal or other cells appropriate for the lining of the brain ventricles. The final chamber 840 in this implementation represents a venule vasculature, lined with the appropriate brain endothelial cells. Then membrane 831 between the CSF and venule spaces may have pores large enough to support the entry of leukocytes, if desired.

Figure 10C:
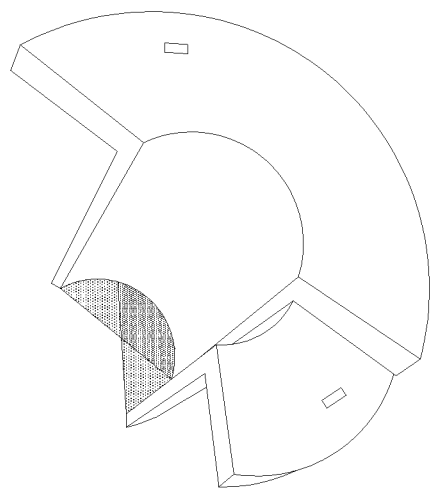
FIGS. 10A-10C show sectional images of the assembled transwell inserts of FIG. 9B, where filters are attached to the ends of the transwell inserts.
Figure 10B:
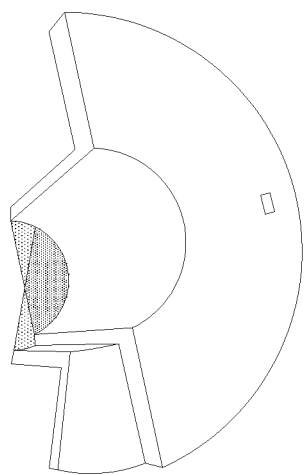
Figure 10A:
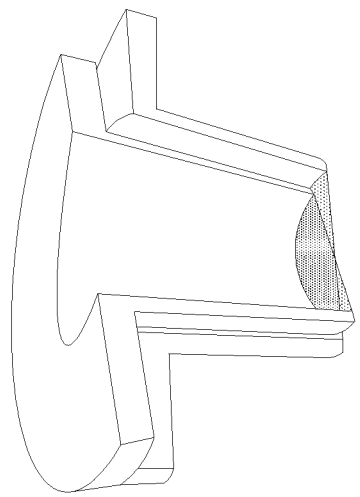

FIG. 9A shows an image of two nesting transwell inserts fabricated by 3D printing according to one embodiments of the present invention. FIG. 9B shows the two nesting transwell inserts of FIG. 9A after assembling. FIG. 9C is an enlarged view of FIG. 9B, where a gap 900 between the two inserts. FIGS. 10A-10C are cross-sectional images of the two transwell insert of FIG. 9B, where a filter is attached to each of the transwell inserts and span the end of the corresponding transwell insert. Cell culture chamber are defined by the space between the filters and any space between the inner and outer covers (not shown).

Figure 11:
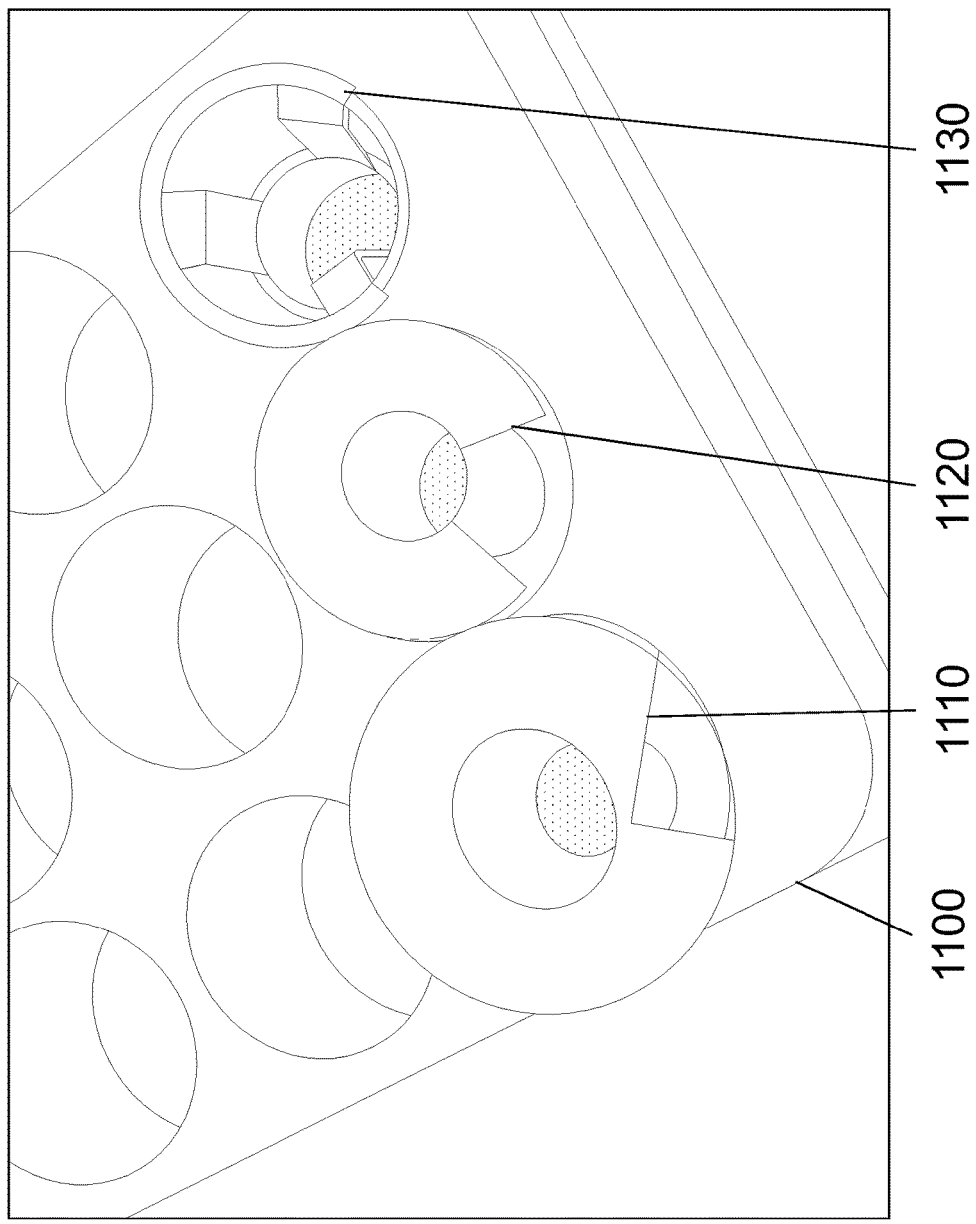
FIG. 11 shows insertion of the transwell inserts to a 12-well plate according to one embodiment of the present invention.

FIG. 11 shows a conventional 12-well plate 1100 with three different transwell inserts. The transwell inserts 1110 was produced by 3D printing as described above, with a notch cut out to allow access to the well. 1120 is a transwell insert produced by molding in PDMS. 1130 is a commercial transwell insert.

Figure 12A:
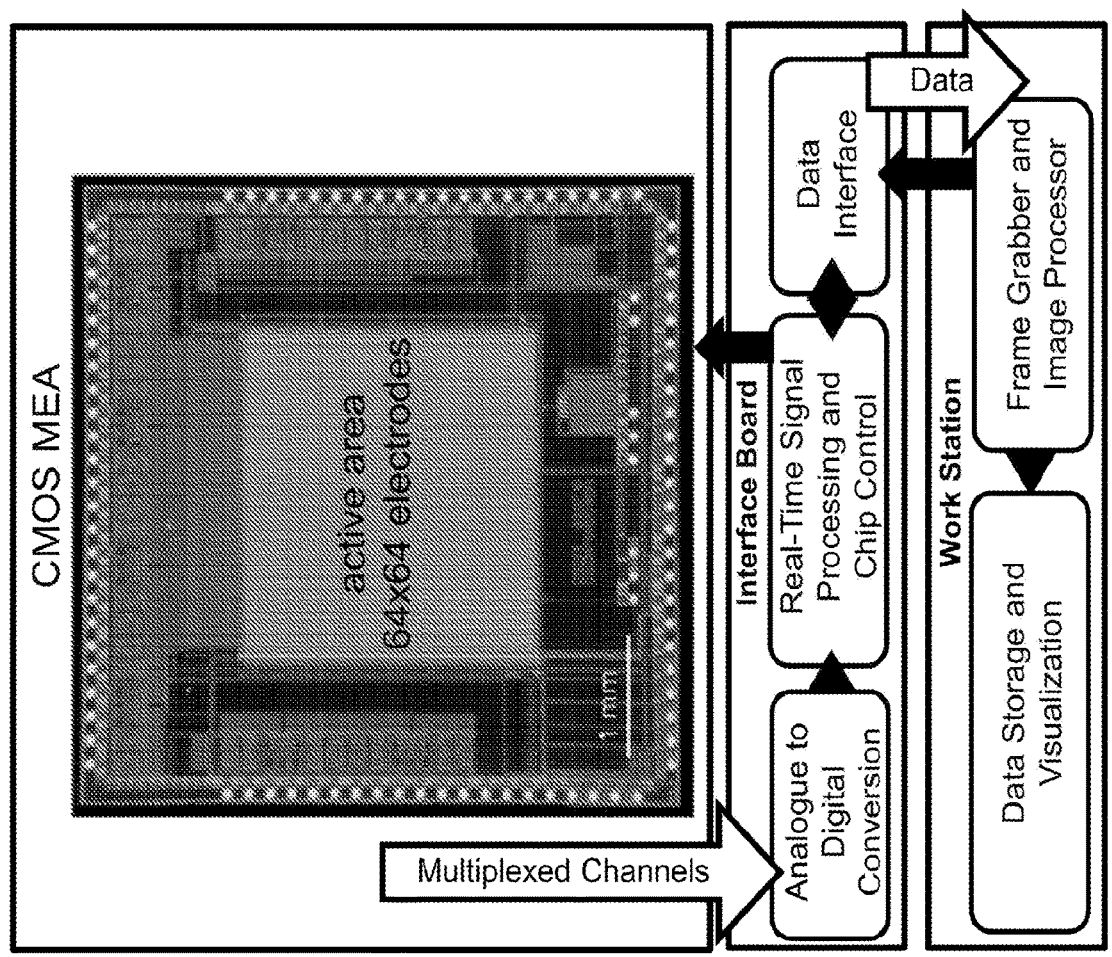
FIGS. 12A-12C show a multi-electrode array (MEA).
Figure 12B:
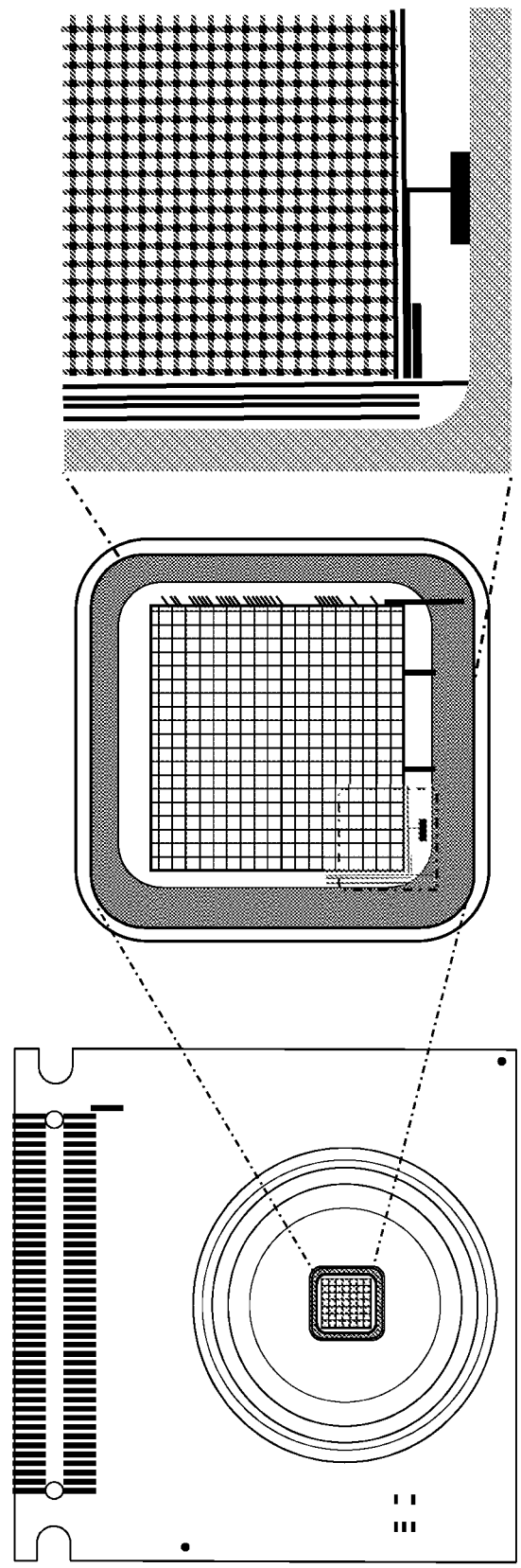
Figure 12C:
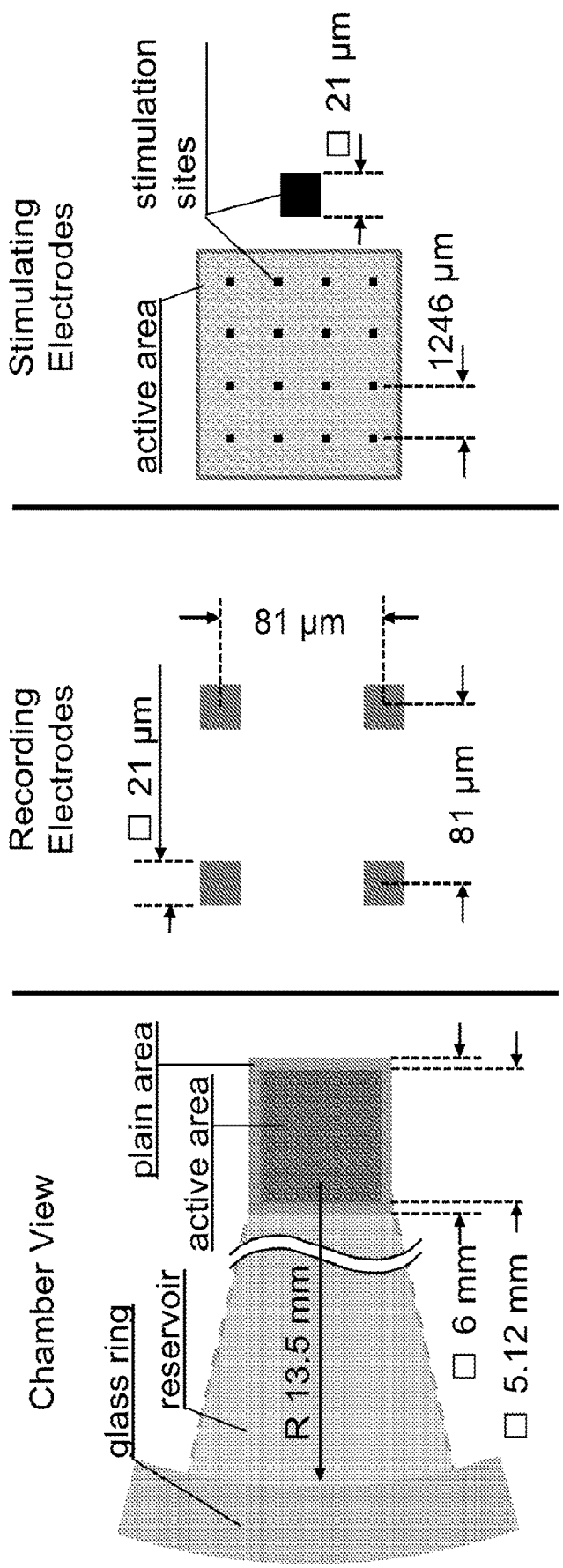
Figure 12D:
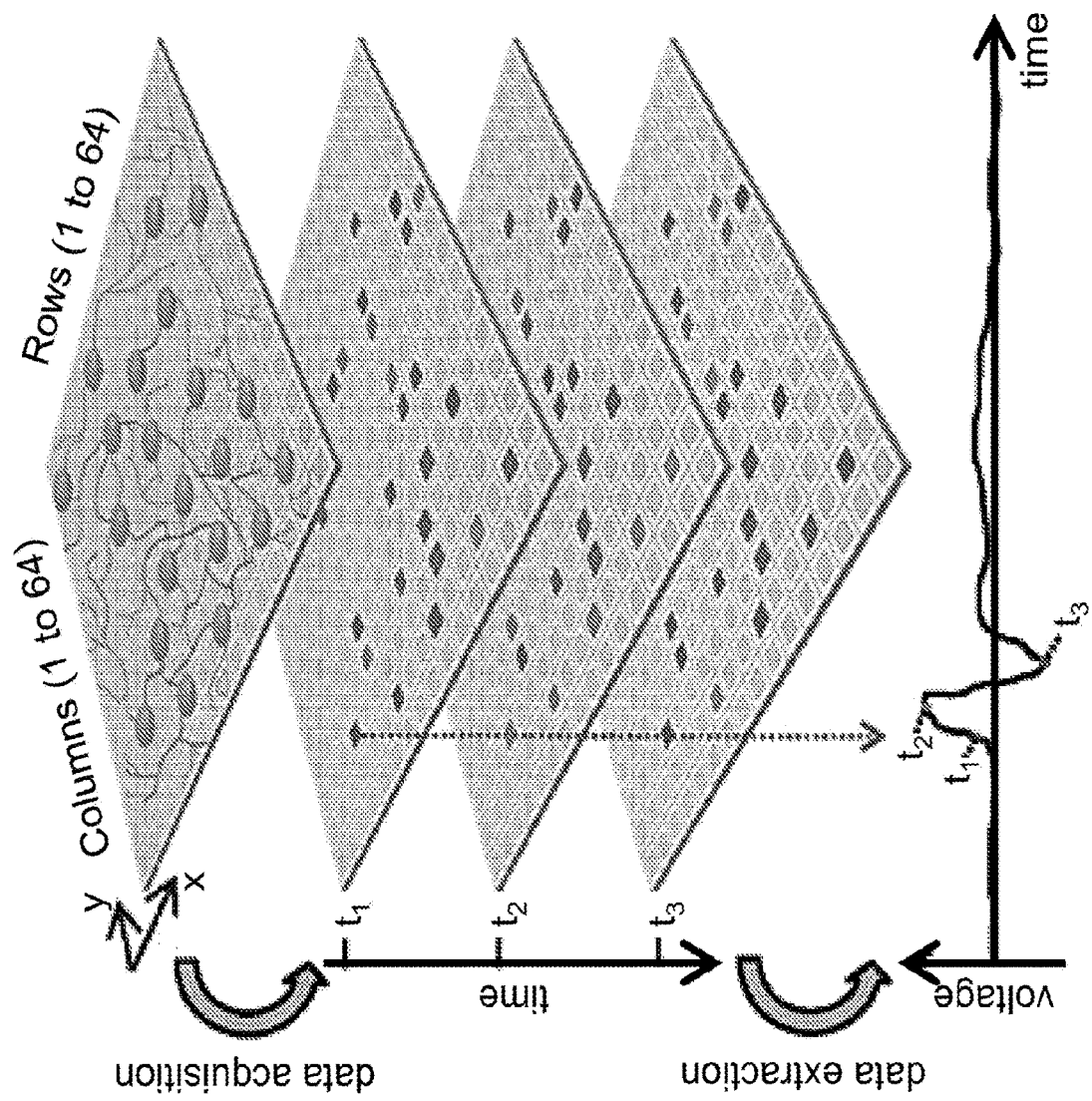
FIG. 12D shows the data acquisition sequence and waveform reconstructions for the MEA.
Figure 13:
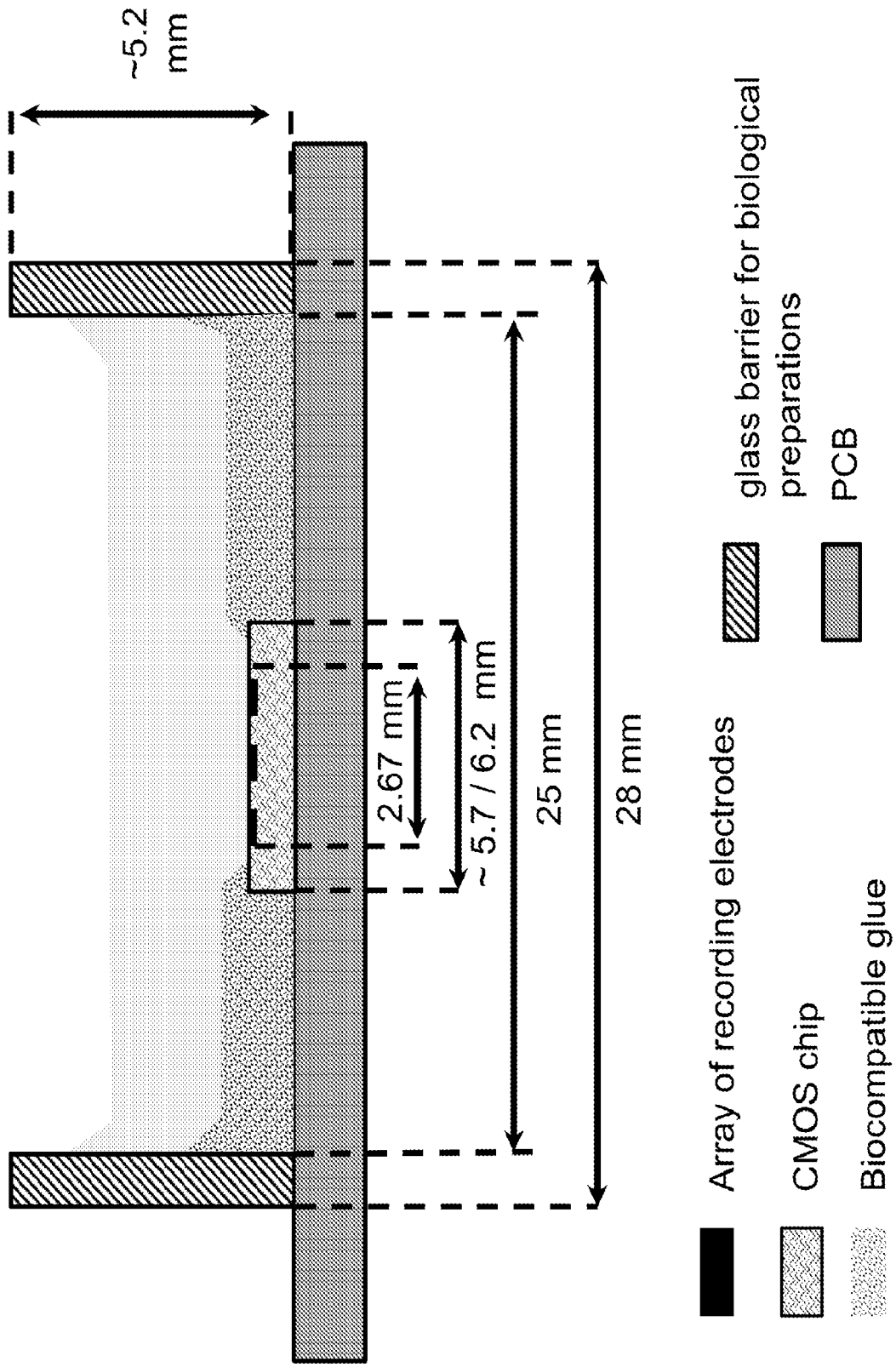
FIG. 13 is a cross-sectional view of the MEA of FIG. 12.
Figure 14B:
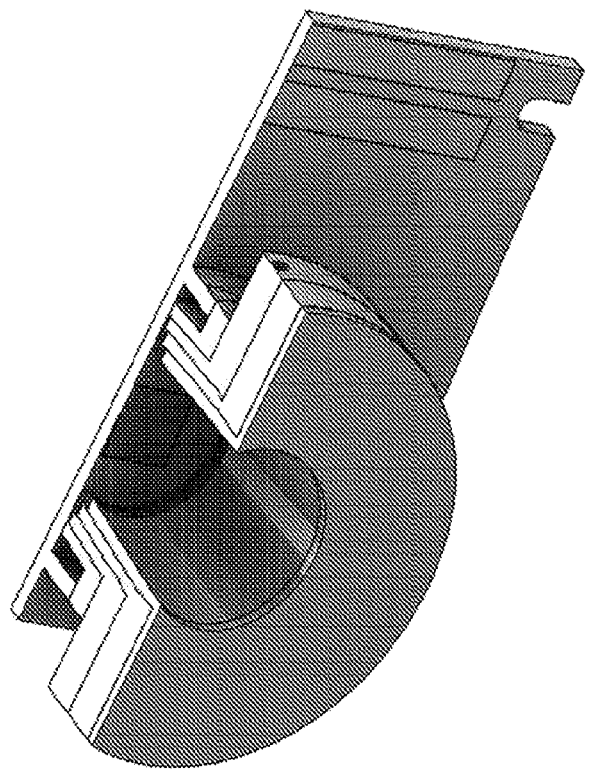
FIGS. 14A-H show how the stacked transwell inserts can be attached to and interface with an MEA according to certain embodiments of the present invention.
Figure 14A:
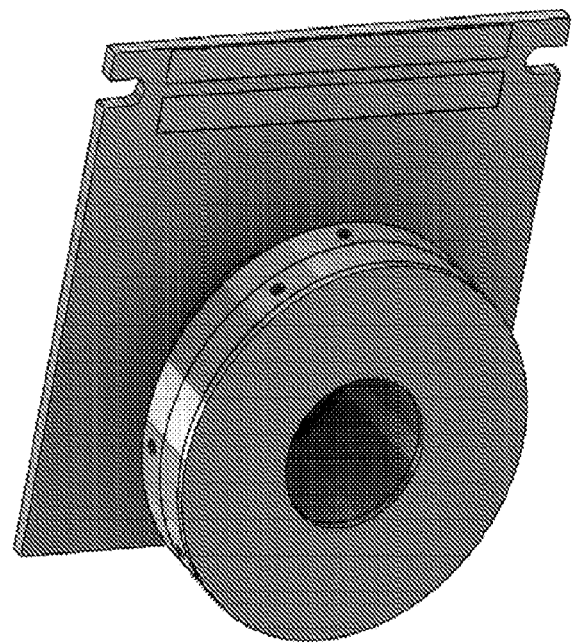
Figure 14D:
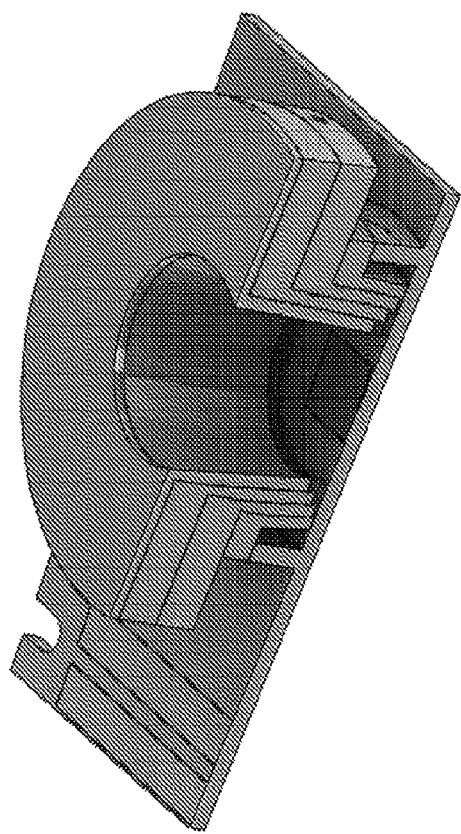
Figure 14C:
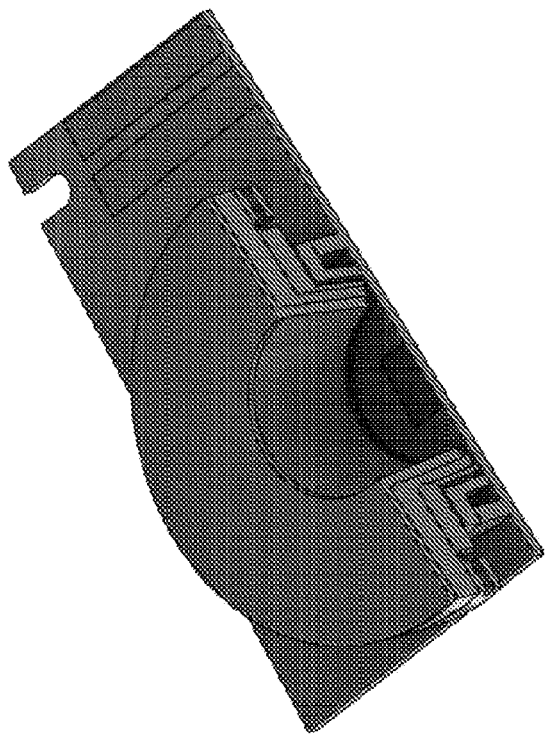
Figure 14E:
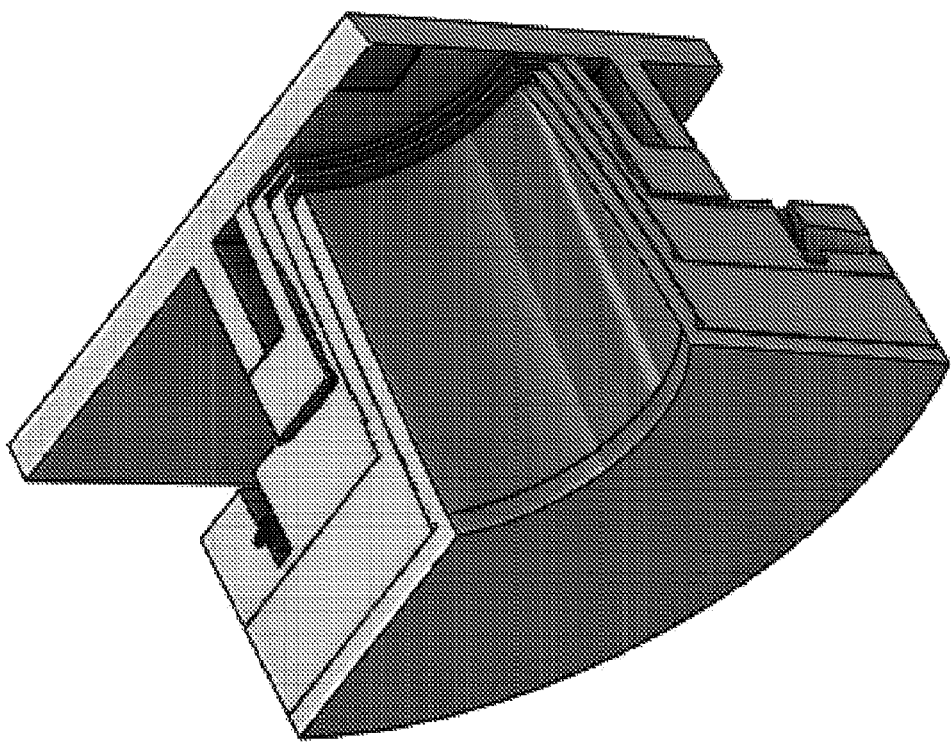
Figure 14F:
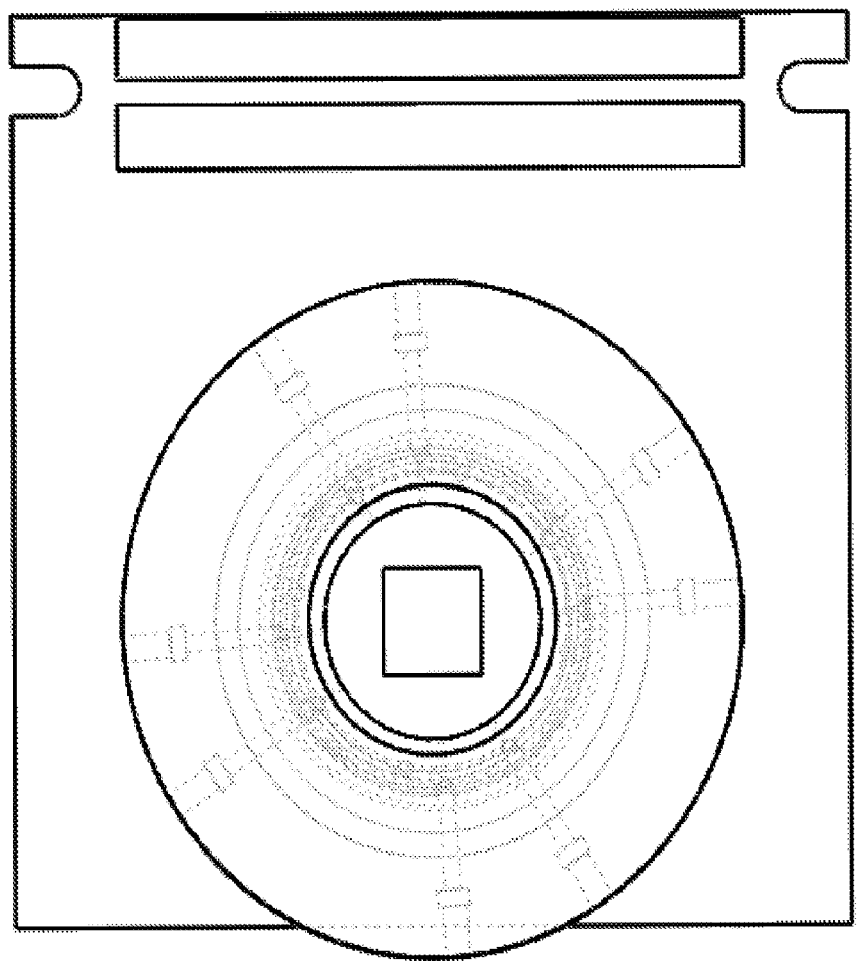
Figure 14G:
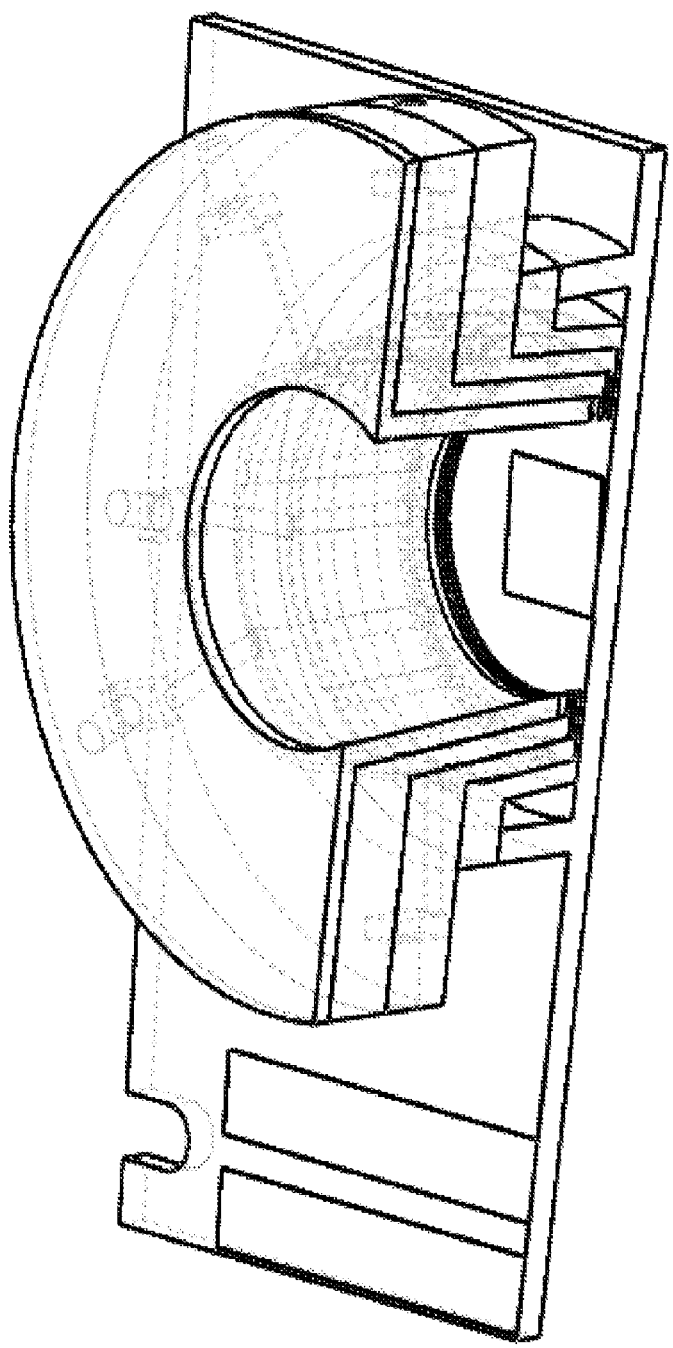
Figure 14H:
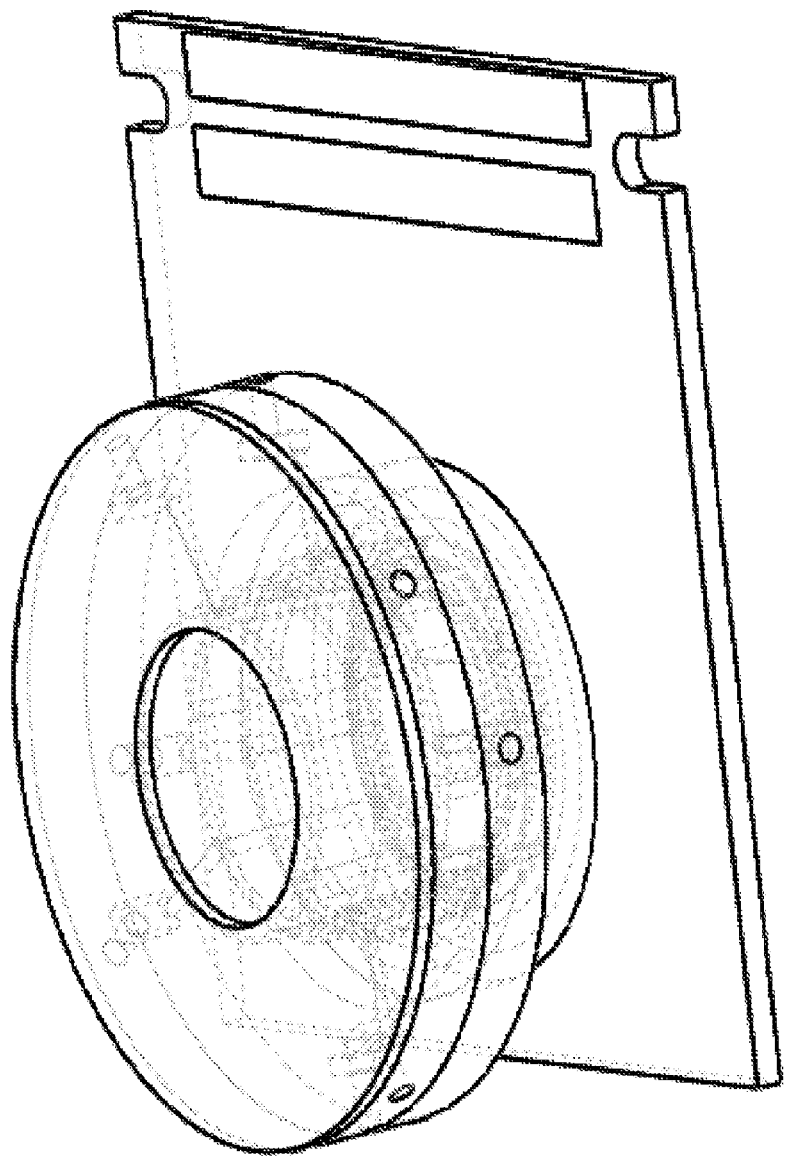

In certain aspects, the present invention relates to assembling the stacked transwell inserts on electrodes. It is important in the study of the neurovascular unit to be able to record the electrical activity of the neurons to determine the extent to which they are affected by the permeability of the blood-brain barrier and the drugs, toxins, and metabolites that either diffuse or are transported across it. One common means to accomplish this is to pattern the substrate that supports the neurons with a passive microelectrode array (MEA) that is connected to remote amplifiers. Another is use a CMOS MEA, which allows the use of more electrodes with higher measurement bandwidth and fewer cables by creating the actual MEA as part of a CMOS recording microcircuit that includes amplifiers, analog-to-digital converters, multiplexers and signal transfer circuits. FIGS. 12A-12D show one example including the 3Brain GmbH (Landquart, Switzerland) 4096 Multi-Electrode Array (MEA), which can be used to measure the neuronal electrical activity in the neurovascular unit. FIG. 12A shows the CMOS chip and process flow. FIG. 12B has photographs of the 3Brain MEA showing some of the 4096 electrodes. FIG. 12C provides array and electrode dimensions. FIG. 12D shows how action potential reconstruction is accomplished using a commercial frame grabber. In certain embodiments, stacked chambers or nested transwells described above can be interfaced to such an MEA as shown in FIGS. 12A-12B, so as to perform in vitro neuroelectric recording. FIG. 13 shows a cross-section of the 3Brain MEA, with dimensions that are compatible with the technology discussed in the present invention. FIGS. 14A-H show various renderings by which the nested transwell inserts can be interfaced with such an MEA. Note that in this case, since the MEA is not transparent, it will not be possible to image the neurons with transmitted light, but it may be possible were it desired to create an MEA whose electrodes were fabricated from optically transparent indium tin oxide. In the configurations shown in FIGS. 12A-12D, the neurons would be grown on the MEA, and then the other nested layers would be added, either before or after being populated with cells. Similarly, ports on the nested array would make it possible to inject collagen or another matrix, with or without cells, into a chamber after it has been assembled.

Each of the embodiments shown is designed to allow the assembly of layered planar or stackable transwell bioreactors after the cells have grown to confluence, if appropriate, or otherwise certified as suitable for the intended studies, thereby minimizing the risk of failure when all cells are grown together in bioreactors that are permanently interconnected.

In certain aspects, the present invention relates to a system including at least one microfluidic instrument and a bioreactor having stacked layer or transwell inserts as described above. The fluidic perfusion, control, and sensing of each of the chambers in a multi-chamber stacked or nested bioreactor presents significant challenges. Those microfluidic instruments are able to solve the challenges. In certain embodiments, as shown in FIGS. 15A-15C, three classes of microfluidic instruments are provided.

Figure 15A:
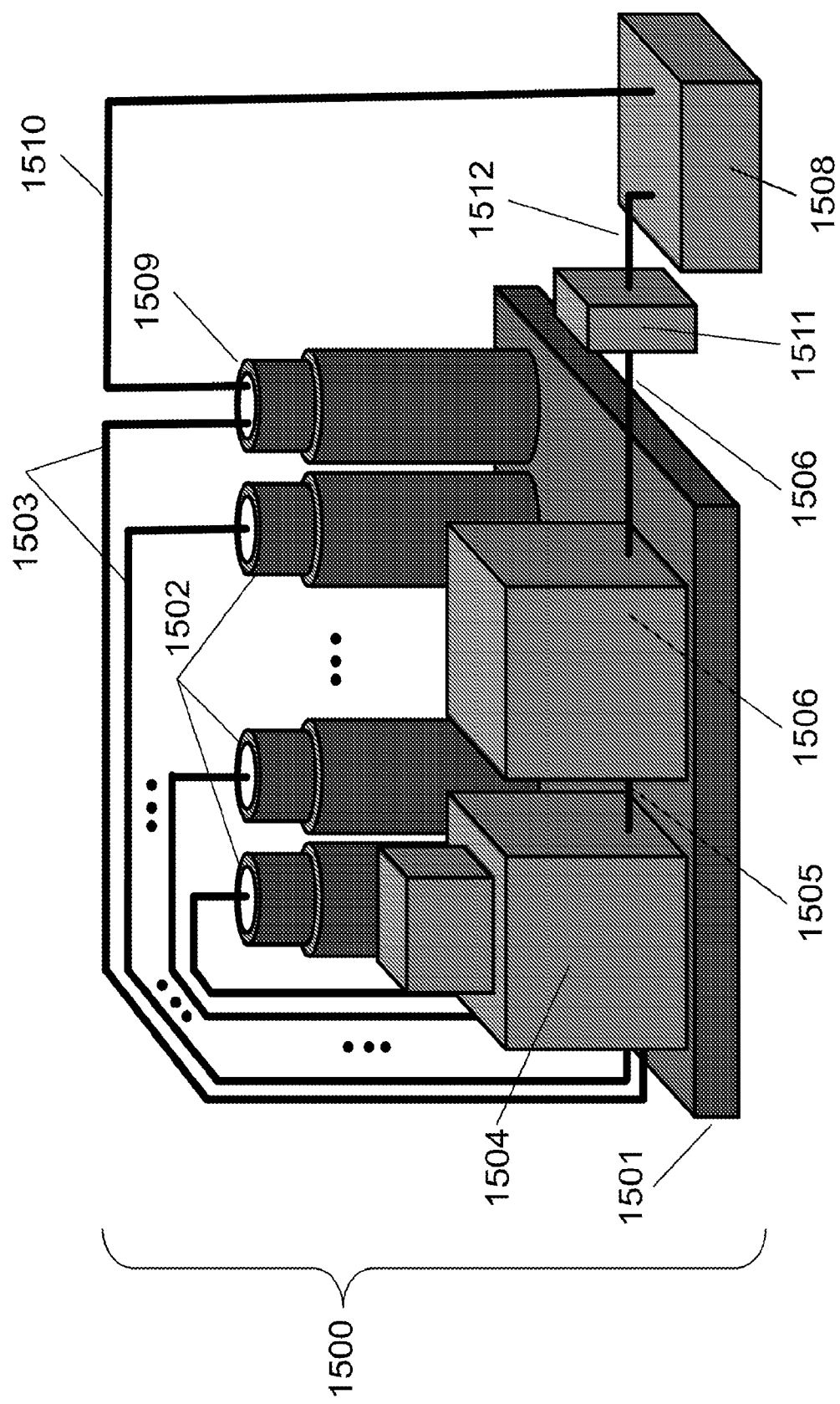
FIG. 15A is a schematic view of a perfusion controller according to one embodiment of the present invention.

As shown in FIG. 15A, the Perfusion Controller 1500 has a base 1501, multiple reagent reservoirs 1502 and lines 1503 that are connected to an input control valve 1504. Fluidic line 1505 connects the output of 1504 to pump 1506, which then can withdraw upon command fluid from reservoirs 1502 and 1509 through one of multiple lines 1503. Reservoir

1509, in this implementation, is for recirculation of media through line 1510 that is connected to the output of bioreactor 1508. The input 1512 to the bioreactor first passes from the pump 1506 through line 1507 and bubble trap 1511. Similar configurations will allow the media to be pulled through the bioreactor 1508 rather than being pushed through as shown.

Figure 15B:
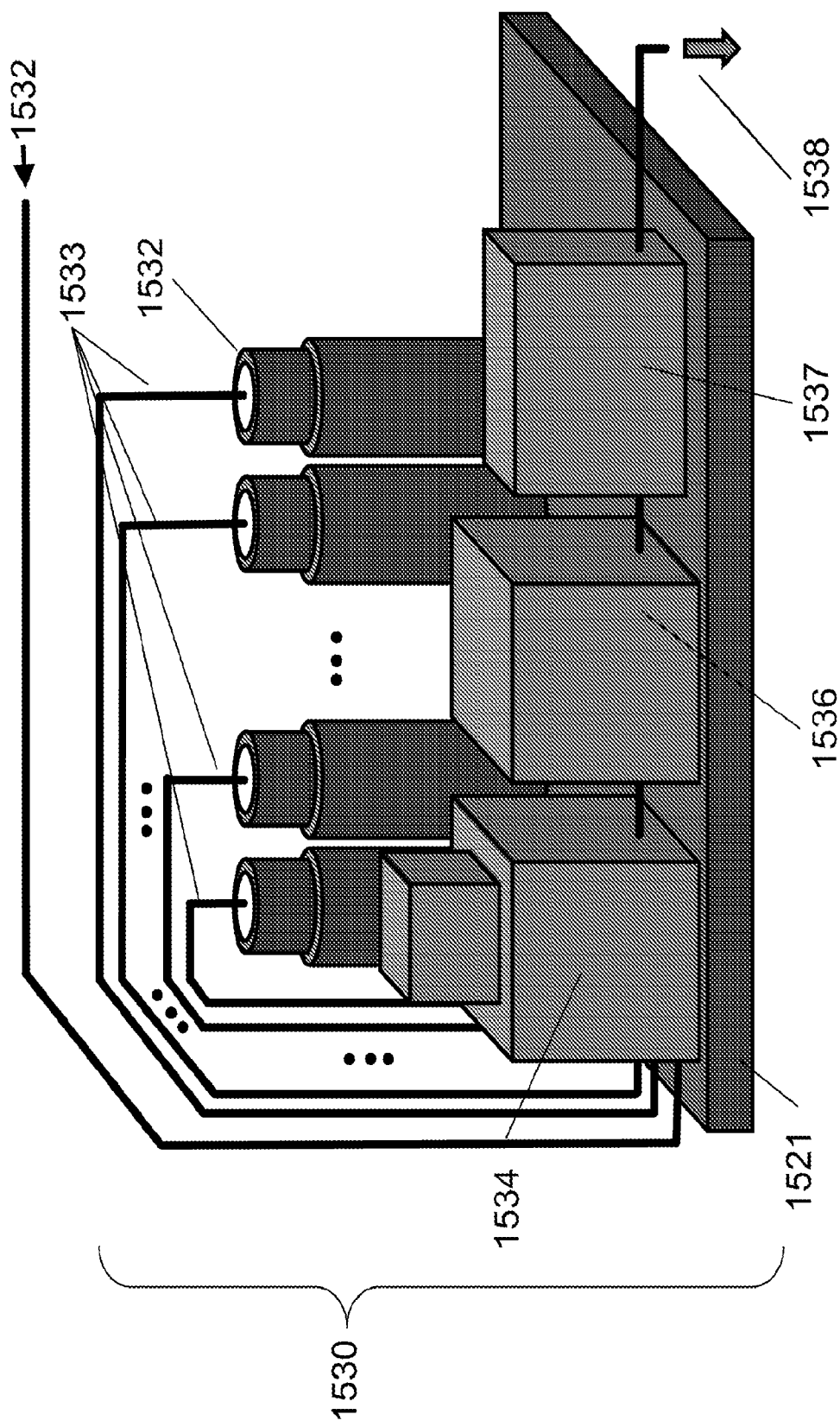
FIG. 15B is a schematic view of a microclinical analyzer according to one embodiment of the present invention.
Figure 15C:
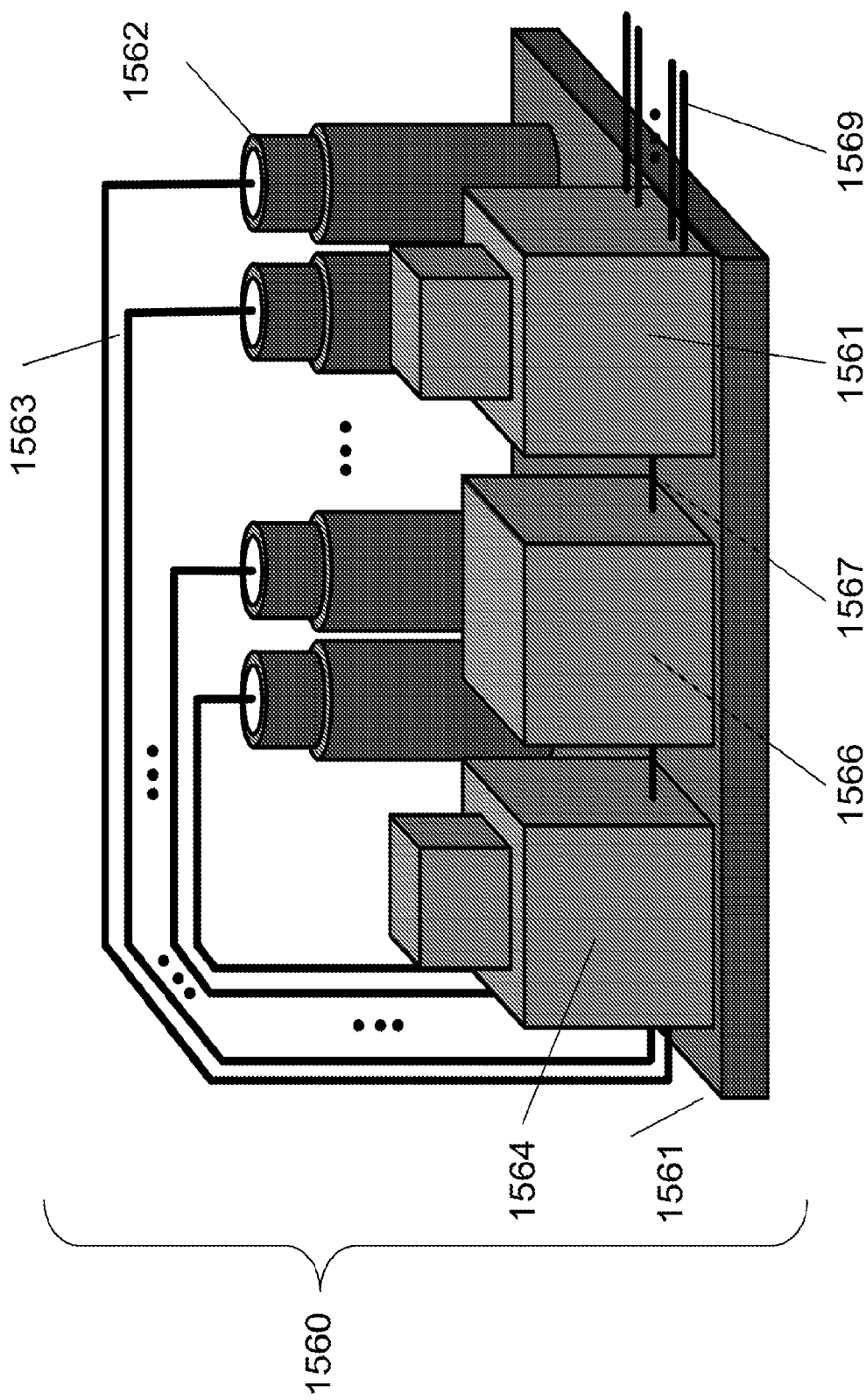
FIG. 15C is a schematic view of a microformulator according to one embodiment of the present invention.

As shown in FIG. 15B, the MicroClinical Analyzer 1530 uses similar hardware to provide in real time the electrochemical or other measurements of the metabolic activity of cells growing in a bioreactor chamber. Pump 1536 draws fluid from valve 1534, which can select between one of the multiple calibration reagent vials 1532 via tubes or channels 1533, or from the bioreactor effluent 1532. The output of the pump is directed to an electrochemical sensor array 1537 and then to waste.

As shown in FIG. 15C, the MicroFormulator 1560 has an input selector valve 1564 whose inputs are connected by a plurality of tubes 1563 with media, reagent, drug or toxin vials 1562. The output of input valve 1564 is connected to a pump 1566, and then in turn to an output director valve 1561. The multiple outputs of 1561 are directed through any one of tubes 1569 to any of a plurality of devices or bioreactors, for example the chambers of a layered or nested bioreactor. The temporal control of input valve 1564 allows adjustment of the concentration of chemicals that are then delivered to any one of the output lines 1569 through time-division multiplexing.

Figure 16A:
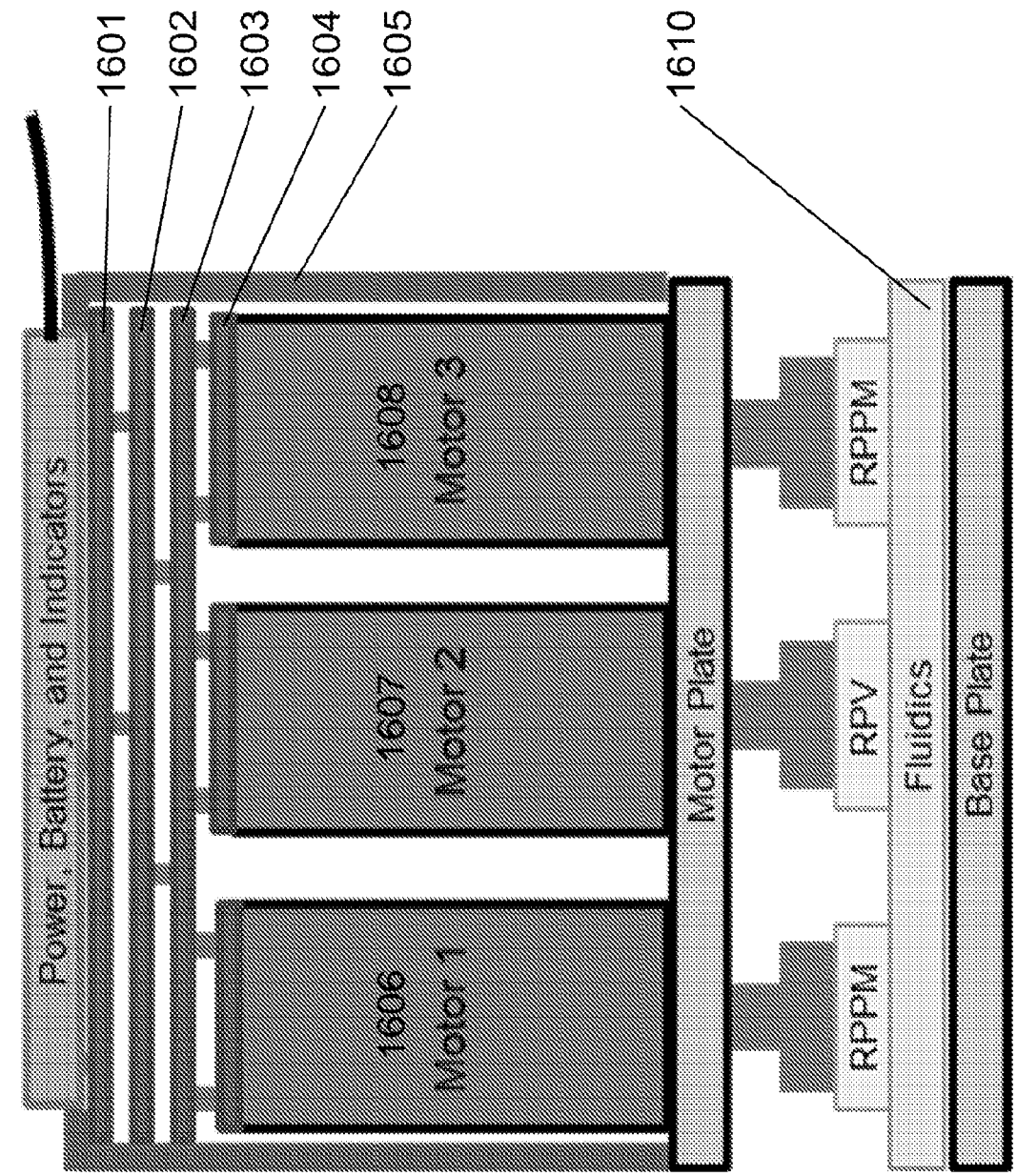
FIG. 16A is a schematic view of a compact smart motor unit according to one embodiment of the present invention.

The functions of the Perfusion Controller, MicroClinical Analyzer, and MicroFormulator can be implemented using a compact SmartMotor unit 1600 shown in FIG. 16A. The unit utilizes three small footprint motors (1606-1608) such as NEMA-8 stepping motors or DC gearhead motors, each of which has a motor connector board 1604. The motor control circuit board 1603 contains a shaft encoder and a motor driver chip for each of the three motors, pogo-pins to deliver four power lines to each motor, and fifty-pin connectors to connect to the logic board 1602, which contains a microprocessor for each motor and a more powerful processor to control complex calculations and synchronize timing with the motor microprocessors and manage communication through the wireless module on the interface board 1601. Both 1601 and 1602 also contain SD memory cards for program and data storage. All boards and motors are enclosed by a hermetic enclosure 1605. As shown in FIG. 16A, the three motors drive a rotary planar peristaltic micropump (RPPM), a rotary planar valve (RPV), and a second RPPM. Other configurations of pumps and valves are easily utilized, with appropriate modifications to the fluidic circuit 1610.

FIG. 16B shows a fluidic circuit 1610 that would enable independent or synchronized perfusion of both sides of a two-chamber BBB bioreactor as described above to accomplish as shown in FIG. 16C the functions 1620 and 1630 for each side of the BBB. FIG. 16D shows a fluidic circuit 1690 that can accomplish the functions for a single MicroClinical Analyzer to analyze electrochemically or by other means the metabolic activity of seven separate bioreactor chambers, and also calibrate the sensors using known calibration solutions.

Figure 16C:
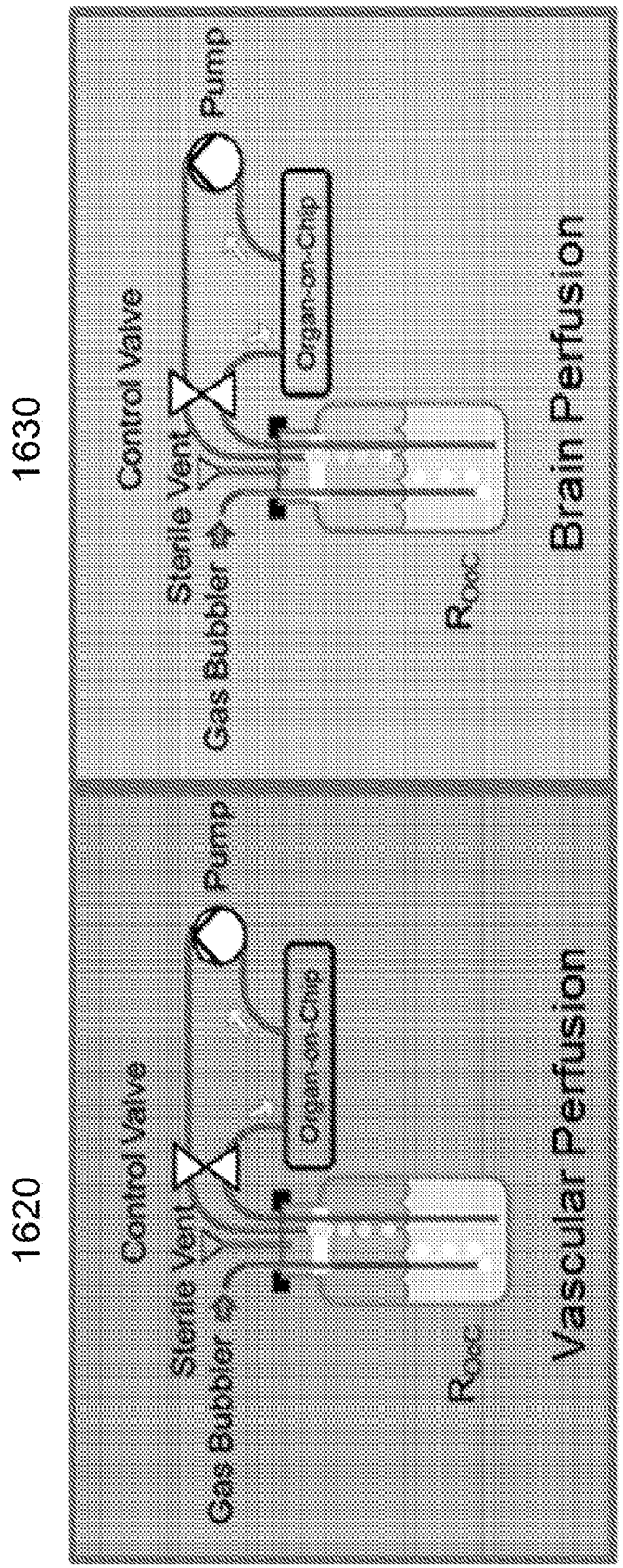
FIG. 16C shows schematically independent or synchronized perfusion of both sides of a two-chamber BBB bioreactor according to one embodiment of the present invention.
Figure 16D:
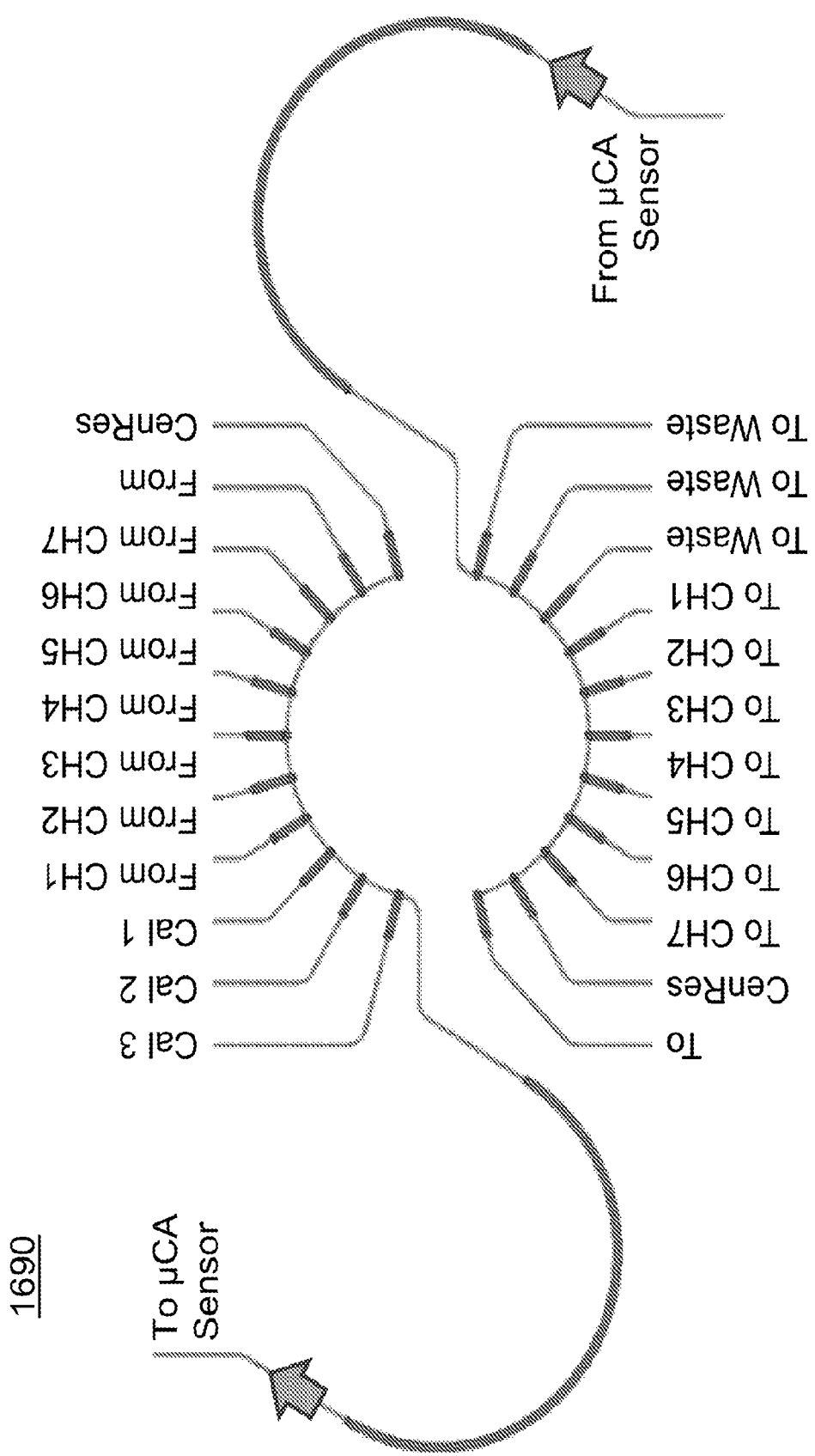
FIG. 16D shows schematically a fluidic circuit for controlling a microclinical analyzer according to one embodiment of the present invention.
Figure 16E:
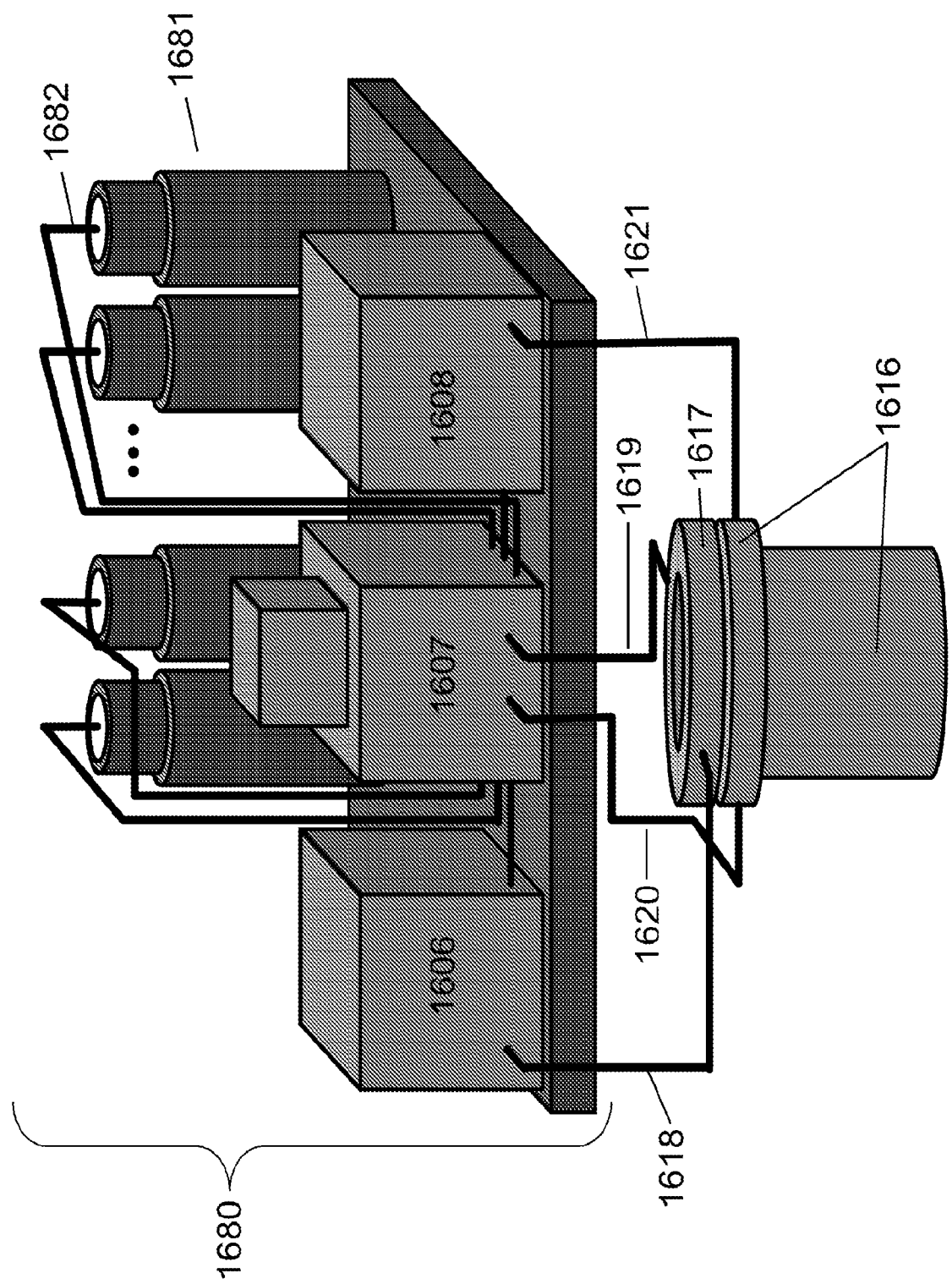
FIG. 16E shows use of the perfusion controller to perfuse and control two nested transwell inserts according to one embodiment of the present invention.

FIG. 16E shows how the perfusion controller in FIGS. 16A-C could be used to perfuse and control two nested transwell inserts 1616 and 1617. The three-motor controller 1680, with RPPM 1606, RPV 1607, RPPM 1608 and vials 1681 allows the connection of pump 1606 to the input side of insert 1617 via line 1618, and RPPM 1608 to the input side of insert 1616 via line 1621.

Figure 17A:
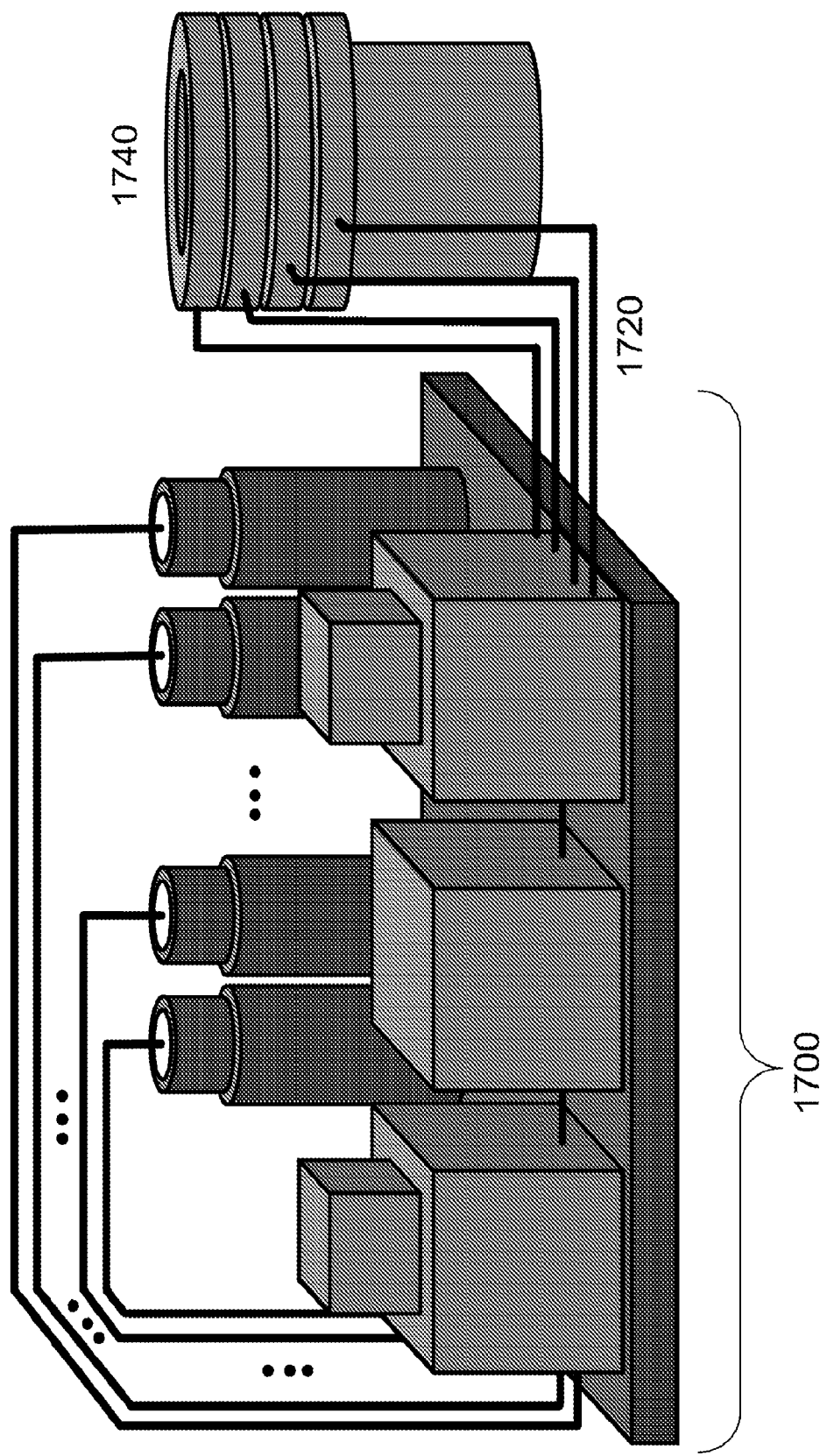
FIG. 17A shows schematically use of the micro formulator to control the perfusion of multiple nested transwell inserts according to one embodiment of the present invention.

One difficulty with perfusing and controlling a larger number of inserts is the need for a large number of motors, pumps, and valves. This requirement can be overcome by modifying the MicroFormulator to control multiple nested or layered chambers. FIG. 17A shows how MicroFormulator 1700 can control the perfusion of multiple nested transwell inserts 1740 by lines 1720. Given the ability of a MicroFormulator to deliver fluid to any of 24 lines connected to 24 input ports in nested or layered bioreactors, the system in FIG. 17A would allow the single-line control of six four-chamber systems 1740, 12 two-chamber systems, or four six-chamber ones.

In another embodiment, a second microformulator could be added to actively pump fluid from each well of the bioreactor and thereby direct this fluid to another set of reservoirs, as well as to ensure that the bioreactor chambers are all at the same atmospheric pressure since the pressure drop within the input microformulator would be balanced by the pressure drops on the outlet microformulator. Otherwise, with a single microformulator driving fluid through the devices, a higher pump pressure would be required to drive the fluid both into and out of the bioreactor and hence the pressure drop on the input and output circuits would add rather than cancel, thereby biasing the reservoirs at a higher-than-atmospheric pressure. In this case, the two microformulators would provide two-line control of of six four-chamber systems, 12 two-chamber systems, or four six-chamber ones.

Figure 17B:
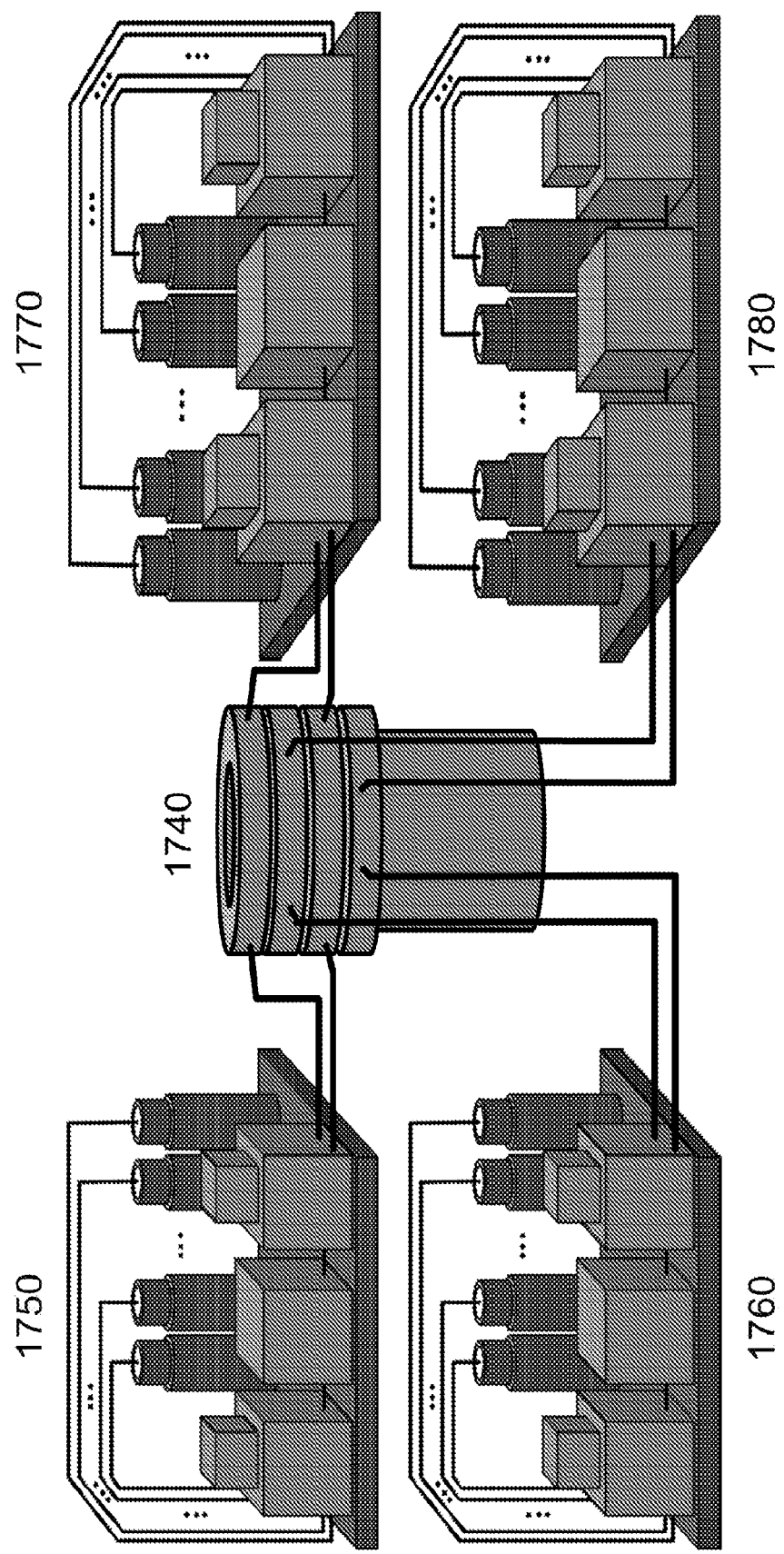
FIG. 17B shows schematically use of four micro formulators to control both inputs and outputs of each insert, according to one embodiment of the present invention.

Given the need to control both inputs and outputs of each insert treated as pairs with a barrier between them, such full control of a transwell system can be accomplished with four MicroFormulators 1750, 1760, 1770, and 1780, as shown in FIG. 17B. The staggered configuration of the connections to the flanges in the nested insert set 1740 is required to provide independent control of the solutions in the two chambers on either side of a particular barrier.

A critical requirement of barrier experiments using transwell inserts is to be able to measure the electrical impedance across each barrier, termed the TransEndothelial Electrical Resistance (TEER) when measured at DC or a single AC frequency, and the impedance spectrum when measure over a range of frequencies. As we discussed in FIG. 6G, this is typically done in transwell inserts with WPI EVOM2 electronics and chopstick electrodes. We have developed a four-wire swept-frequency impedance analyzer that can measure both the TEER and the impedance spectrum. We introduce a device based upon the modules discussed above to create an instrument 1800 shown in FIG. 18A that can automatically measure the TEER or the impedance spectrum for each well in a 24 transwell plate 1860 using four twenty-four port MicroFormulators (1820, 1830, 1840, and 1850) to control the electrical connections between the wells and inserts and the impedance analyzer 1870 that are made through the saline filled tubes entering each well and insert. This instrument has the advantage over the EVOM2 of not only measuring the TEER/impedance spectrum but also controlling the delivery and removal of fluid from each well and insert under computer control without the need to either remove the system from the incubator or remove the top from the well plate. The system uses MicroFormulators 1820 and 1830 to draw fluid from vials 1801-1805 and 1806-1810, respectively and direct it to either outside the insert in the well or the inside the insert within the well for each well in any of twenty-four well plate 1860 via twelve distribution networks 1890. Fluid is removed from the corresponding wells using MicroFormulators 1840 and 1850, the latter removing fluid from the volume of the well outside the insert and depositing it for analysis in the sample-collecting well plate 1880. In another embodiment, the fluid removed from the insert within the well could be directed to another sample-collecting well plate. The Micro-Formulator has the capability to back wash all of the pumps and valves and deposit the waste solution in vials 1825 and 1845. Most importantly, since each fluidic line in the distribution networks 1890 is connected through the valve to the input of the four 24-port valves, these fluidic lines, when selected, are filled with a saline solution and hence can be used to connect electrically both sides of an individual well/transwell-insert to both current (+I and −I) electrodes (1871 and 1872) and voltage (+V and −V) electrodes (1875 and 1876) that are located between the 24 port valve and the corresponding pump in each of the four microformulators. Note that the pump, because of its peristaltic operation, will break the electrical circuit beyond the electrodes. Wires 1873 and 1874 deliver the current produced by the impedance analyzer 1870 to current electrodes 1871 and 1872, and wires 1877 and 1878 are used to measure the voltage between voltage electrodes 1875 and 1876 that is developed across the transwell barrier as a result of the current flowing through it. The fluid filled tubes have some resistance associated with the electrical conductivity of the saline within them, but the use of a four-wire measurement allows a proper measurement of the barrier impedance independence of the resistance of the fluid in the tubes.

The electrodes 1871, 1872, 1875, and 1876 are inserted into punched or molded holes in the fluidic path between the pump and valve in such a way as to allow a conductive fluid path through any of the individual wells in a plate when all four perfusion vales are addressing the same well. The ability to analyze the impedance spectrum of the conducting region between the openings of the four active fluid ports (two on each side of the membrane between the two chambers) allows elucidation of cell layer confluence and health, TEER, fluid level control, detection of bubbles, and even pumping speed calibrations for each perfusion module.

Figure 18A:
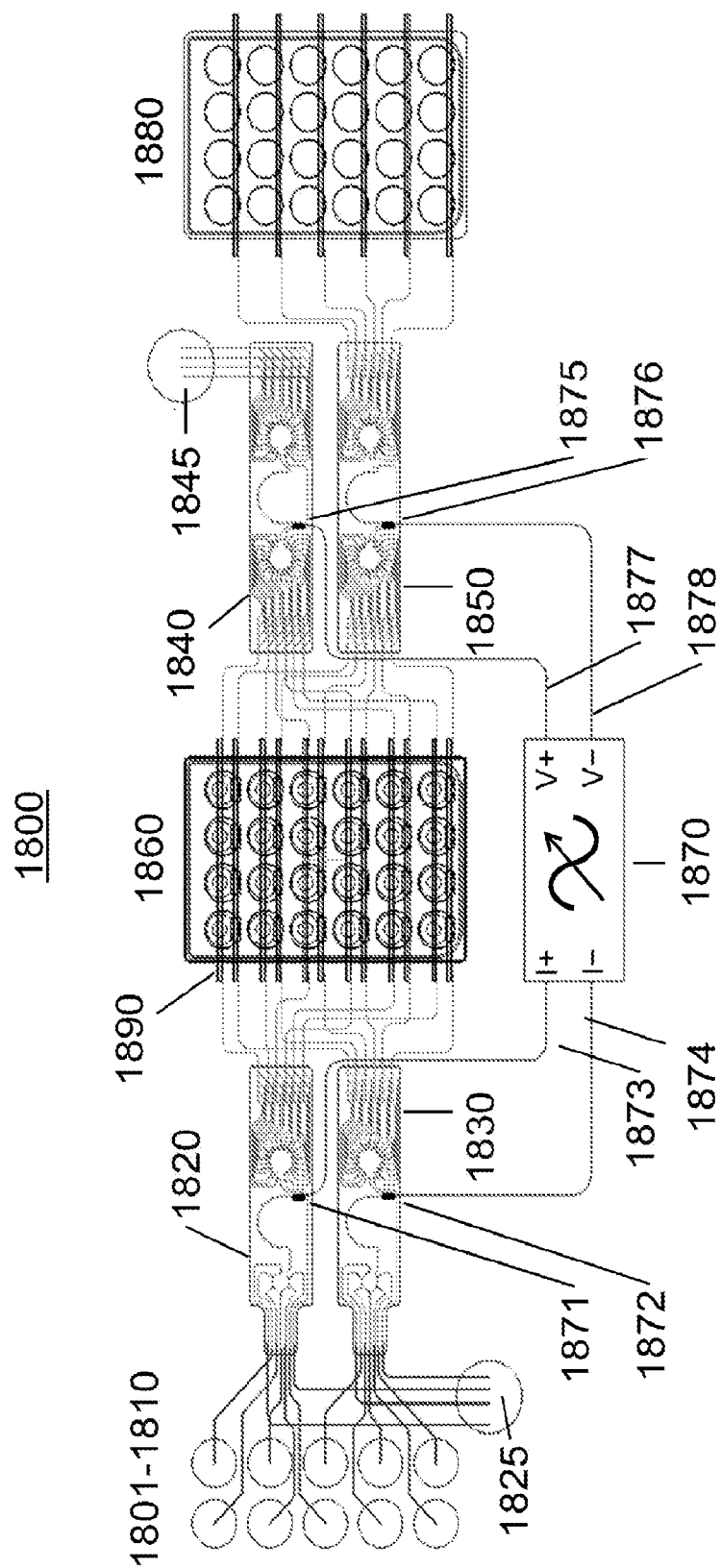
FIG. 18A shows an instrument that comprises four 24-channel microformulators, electrodes, and a swept-frequency impedance analyzer that together can control each well in a 24 transwell plate and measure the electrical impedance spectrum of the cells growing on each insert, according to one embodiment of the present invention.

With the addition of electrodes, cables, and the electronics to four otherwise independent microformulators, we have created a new instrument that far exceeds the capabilities of existing TEER or impedance spectroscopy systems, which measure one membrane at a time and require either specialized bioreactors with internal electrodes in each chamber, or the removal of the well plate from an incubator, removal of the lid, and insertion of a four-electrode tweezer-like probe (FIG. 6G) to make electrical contact with the fluids on both sides of the transwell membrane. Hence this configuration 1800 enables the high through-put measurement of TEER from either 24 individual transwells as shown in FIG. 18A, or combinations of nested transwells as shown in FIG. 17B.

Figure 18B:
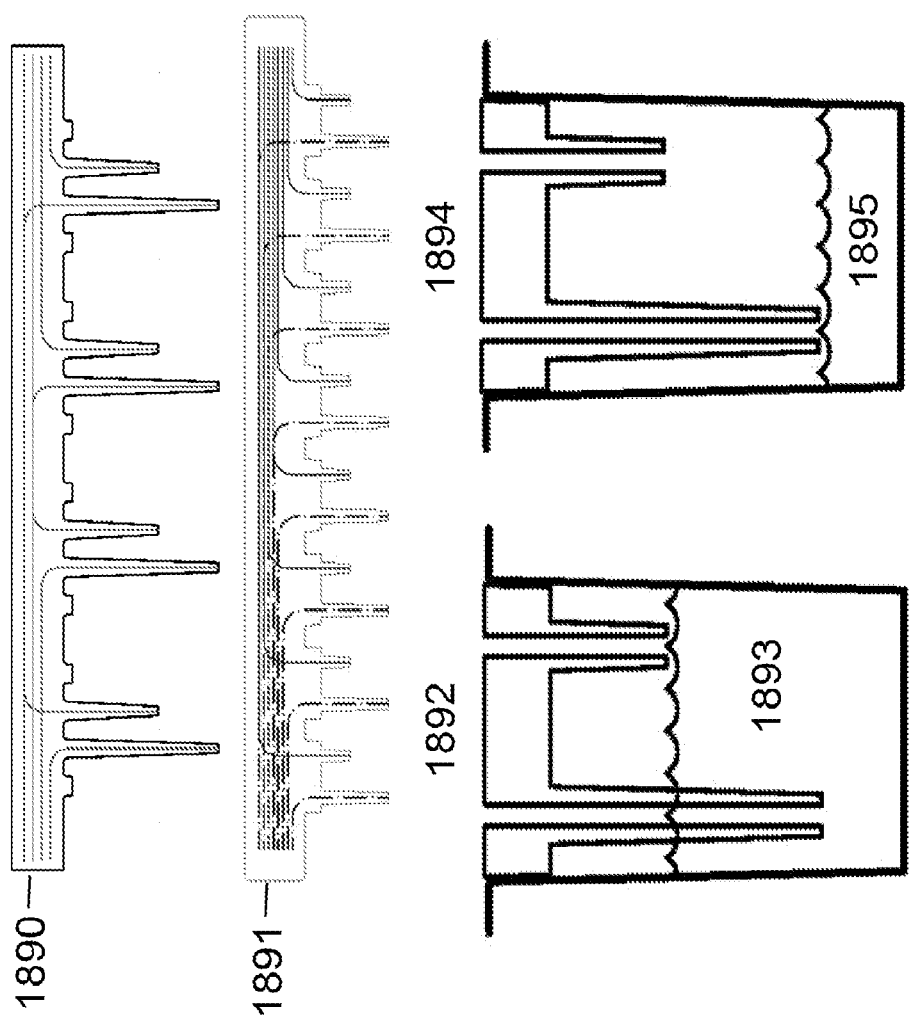
FIG. 18B provides details of how a machined, hot-embossed, or laser-cut, two-sided fluidic network can provide two fluidic connections to either a row of four wells (1890) in a 24-well plate or 12 wells (1891) in a 96 well plate, according to certain embodiments of the present invention.

FIG. 18B provides details of how a machined, hot-embossed, or laser-cut, two-sided fluidic network can provide two fluidic connections to either a row of four wells (1890) in a 24-well plate or 12 wells (1891) in a 96 well plate. This figure also shows how the high fluid level 1893 in well 1892 could be detected during filling using the TEER configuration in FIG. 18A. A slight modification of the TEER circuitry would also allow detection of the lowest level 1895 in a well 1894 being emptied. The lengths of the fluidic tubes on the distribution networks 1890 extending into the well cavity of plates can be tuned to a variety plate types and transwell inserts in such a way that there is always fluid over cell layers and to insure that no air is pulled under transwell inserts during fluid changes. This length tuning also allows for predictable fluid volumes in the wells as a passive function of extracting liquid from either the upper level tube or the lower level tube. By tracking the volumes in combination with this inherent level control systems can be configured to provide predictable fluid levels at three different, repeatable levels, e.g., ⅓, ⅔ and full operating volumes.

Figures 18C, 18D, 18E:
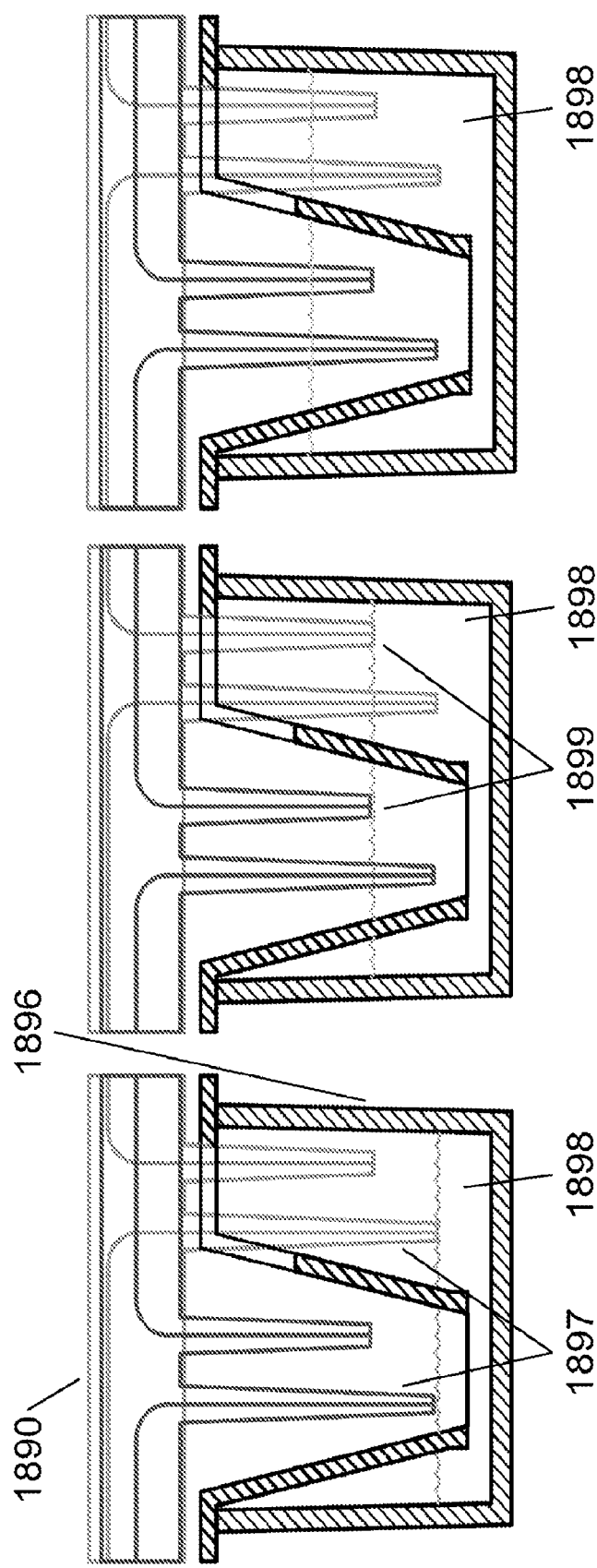
FIGS. 18C-18E shows how the electrical impedance measuring circuits in FIG. 18A enable the measurement and control of fluid volumes according to certain embodiments of the present invention.

FIG. 18C show how the ends of fluid removal tubes 1897 in the fluidic network 1890 are exposed when the level of fluid 1898 in the transwell and the well is at its lowest limit. This state could be detected using the impedance analyzer. Similarly, in FIG. 18D the fluid delivery tubes 1899 can be used with the impedance analyzer to sense the upper level of fluid. Metering by the pumps could be used to increase the fluid level to higher than the upper-sensed level, as shown in FIG. 18E.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

EXAMPLE 1

A Wet-Assembleable Layered NVU Bioreactor

In certain embodiments, one NVU design uses permanently bonded PDMS layers that must be completely assembled prior to cell seeding, thus precluding disassembly for tissue acquisition and additional examinations for proteomic or genetic analysis such as RNAseq. Furthermore, the NVU is useful only if all cell types within all chambers achieve the required cell confluence and viability on the same timescale.

As an improvement of the above NVU, the present invention provides a design by moving from PDMS to COC or another material. The design includes a stackable planar device that can be assembled into an NVU after cell seeding and maturation, creating four 300 µm-thick chambers (vascular, neuronal, CSF, and vascular, bottom-to-top) with glass coverslips sealing the bottommost and topmost chambers.

In this improved design, a clamped bioreactor is provided with a brass clamp providing the force to keep multiple layers in fluid-tight proximity as required to grow endothelial cells.

As shown in FIG. 3A, in one example, a five-layer layer bioreactor is implemented in PDMS using monolithic casting techniques or in COC or another thermoplastic/resin. The membranes that can be used in the bioreactor include commercial track-etched or 1002F photoresist membranes.

In certain embodiments, PDMS or hot-embossed COC may be used for producing the bioreactor. In certain embodiments, the layers may also be bonded before seeding. In certain embodiments, leukocyte extravasation from the upper vascular chamber into the CSF chamber may require membranes with larger pores.

EXAMPLE 2

Generation of Functionally Validated Human Cortical Neurons for the NVU-IOM System Because of the recognized differences between human and mouse/rat/dog physiology, there is general recognition that human cells need to be incorporated as early as possible in the drug discovery pipeline. However, there are severe limitations in the commercial supply of human cortical neurons. Therefore, in certain embodiments, a NVU is provided with incorporated human glutamatergic dorsal forebrain (cortical pyramidal) neurons and co-differentiating astrocytes.

De-identified human induced pluripotent stem cells (iPSCs) derived from control subjects, previously published by the Bowman and Neely group, are used to generate the neuronal/glial cultures. A dual SMAD inhibition monolayer method is used which exposes iPSCs for the first 11 days to LDN 193189 and SB431542, inhibitors of the Bone Morphogenetic Protein (BMP) and Tumor Growth Factor-β1 (TGF-β1) pathways, respectively, to induce ontogeny-recapitulating Pax6, FoxG1, Tbr2 positive cerebral cortical pyramidal neuron progenitor cells (NPC) with high efficiency. Terminal differentiation into post-mitotic, electrically active, cortical glutamatergic pyramidal-like neurons is initiated by passaging the NPCs with accutase onto a poly-ornithine and laminin coated surface, leading to the sequential production of deep layer, then upper layer, cortical pyramidal neurons, as well as GFAP, S100 morphologically defined astrocytes. Greater than 95% of the neurons generated by this approach are positive for markers of glutamatergic cortical pyramidal neurons. Furthermore, the astrocytes that differentiate in these cultures are derived from the same neuroprogenitors (radial glia) and are thus reflective of the true developmental lineage relationships that exist in vivo between cortical neuronal/glial subpopulations. The functional and developmental identity of the post-mitotic cortical neurons and astrocytes are validated at days 30, 60, and 90 (final stage) by assessment of neuron and stage-specific markers by quantitative RT-PCR, immunocytochemistry, and electrophysiological activity, as described in the following example 3.

Experimental approach. The neurons and co-differentiated astrocytes are functionally validated ahead of plating into the lowest level (brain side) of the NVU. The neural tissue is either plated onto a Complementary Metal Oxide Semiconductor multielectrode array (CMOS MEA) and/or a layered NVU, as well as on a cell culture-quality plastic for longitudinal functional assessment of the BBB qualities of the NVU and neuronal health.

Assessment of Neuronal Marker Expression and Synaptic Maturation: The expression of differentiation stage- and neuron-specific markers is assessed by qPCR and immunocytochemistry using published methods. NPCs (day 15) are assessed for expression of PAX6, FOXG1, SOX1, OTX1/2, EMX1, TBR2, nestin and vimentin. At day 30 it is expected to observe the expression of β3-tubulin, MAP2, double cortin (DCX), glutamate and VGluT1, as well as TBR1 and CIPT 2, two markers of deep layer V+VI cortical neurons, which are the first to develop. By day 60 of differentiation it is expected to see abundant expression of glutamatergic synaptic markers, including PSD-95, Homer1, synapsin I, Munc13-1, and markers of neurons belonging to cortical layers II-IV, including BRN2, CUX1, and SATB2. By day 90 cortical cultures contain astrocytes that will be identified by their expression of S1000 and GFAP and morphological characteristics. The number of physical synapses present in the neuronal/glial network is quantified by high-content imaging of synaptic puncta double-labeled for a presynaptic marker (synapsin 1/Munc13-1) and a postsynaptic marker (PDS95/Homer1).

EXAMPLE 3

Electrophysiological Validation of Human Cortiacl Neurons in the Stackable Layered NVU In certain embodiments, to confirm cortical neuron functionality, their electrophysiological activity is recorded using a high-resolution CMOS MEA already been proven to capture spatiotemporal signaling dynamics.

As preliminary data, a 3Brain MEA was used to confirm that the iPSC-derived neurons of the present invention are electrically active and respond pharmacologically. It is observed that spontaneous activity of >90 day cortical neurons that was completely and reversibly inhibited by tetrodoxin and partially inhibited by NBQX).

In this example, a subset of each batch of cortical neurons differentiated for 90 days is plated onto a high resolution CMOS (Complementary Metal Oxide Semiconductor) MEA (3Brain GmbH, Landquart, Switzerland) coated with poly-L-ornithine and laminin. The array contains 4096 independently addressable 21 μm×21 μm recording electrodes pitched at 42 μm and sampled at 7.7 kHz and 16 interleaved stimulating electrodes in a 5.12 mm×5.12 mm working area. Seven days after the plating of the neurons, a time needed to reestablish synaptic connectivity via neurite outgrowth and maturation, the density of healthy neurons is confirmed by calcein staining. Once established, the remaining stackable layers NVU is placed over the neurons as described below. Both spontaneous and evoked electrical activity are recorded. The effects of AP5 (NMDA receptor antagonist), NBQX (AMPA receptor antagonist), and tetrodoxin (TTX, voltage-gated $Na^+$ channel antagonist) are also incorporated into the functional validation to ensure that the activity is consistent with excitatory glutamatergic neural transmission. Spike analysis is performed using BrainWave software (3Brain GmbH) to calculate mean firing rates (MFR) and temporal spike rasters.

EXAMPLE 4

Alternative Material and Designs of the Stackable Layered NVU

PDMS has become the dominant material for microfluidic devices because of favorable features such as optical transparency, elastomeric properties, gas permeability, biocompatibility, ease of bonding to glass or itself, chemical inertness, and low production cost. These advantages are offset by drawbacks that complicate experimental design, such as hydrophobicity and surface hydrophobic recovery, high compliance, low aspect ratio, permeability to water vapor, and adsorption of molecules and nanoparticles. The high adsorption of materials affects soluble factor signaling studies involving small hydrophobic molecules. Therefore, a plethora of surface modifications are used to reduce non-specific adsorption of hydrophobic substances, and improve stability and wettability, based upon the application.

Barriers between compartments in tissue-chips are either made from PDMS, more rigid membranes such as dialysis membranes, track-etched membranes, fluorocarbon foils, or highly porous alumina. The PDMS membranes sag unless thicker than desired, whereas the others are of low optical quality. The development of strong, thin, high-porosity, and optically transparent membranes is a priority. Biocompatible high-porosity membranes produced with 1002F photoresist have ideal optical and mechanical properties.

In certain embodiments, bioreactors are treated with surface modifications, for example plasma/sol-gel treatments. In one example, UPLC-IM-MS techniques are applied which focuses on materials, surface modifications, and UPLC-IM-MS analysis of the affinities of chemicals to bioreactor surfaces. With the aid of interfacing microfluidic devices to UPLC-IM-MS for effluent analysis and conducting MS studies off-line on collected samples, COC microinjection molding, a COC NVU is created according to certain embodiments of the present invention. A variety of filters are tested in the NVU. In certain embodiments, an 8 μm thick 1002F photoresist membrane with 2 μm pores and 40% porosity was use in the NVU.

In certain embodiments, the 1002F porous membranes were incorporated into the layered NVUs and transwell NVUs according to certain embodiments of the present invention. UPLC-IM-MS was used to analyze the role of materials in NVU and control fluidics performance. To minimize elastomer volumes in the NVU-IOM systems, the effects of very thin, flexible membranes present within the RPPM and RPV were examined using proven designs with a thin PDMS membrane between rigid materials.

EXAMPLE 5

A Wet-Stackable Perfused Transwell Insert System

The transwell insert has proven to be a staple of biological barrier membrane research. The impact of microfluidics and organs-on-chips can be increased if they can be implemented in a manner that represents less of a departure from accepted tools and techniques. In certain embodiments, the multicompartment NVU in a nested transwell format would allow investigators to scale existing cell culture applications for immediate use and also be compatible with the neuroelectric MEA.

In certain embodiments, custom PDMS transwell inserts have been molded, which have been attached with various filter membranes, including polycarbonate and anodized aluminum.

In certain embodiments, the stackable transwell design was implemented using a high-quality 3D printer, then in either PDMS or another polymer using molds, and finally with custom developed molds. The design incorporated microfluidic features that permit each compartment to be individually supplied with nutrients or pharmacological treatments via a RPPM/RPV combination.

In certain embodiments, the sealing between individual layers are ensured by different designs. In certain embodiments as described above, the design allows for small vertical gaskets between the sides of the nested inserts. In certain embodiments, a test protocols is developed based on transport of fluorescent dyes and particles to ensure complete fluidic separation.

EXAMPLE 6

Optimization of the NVU Perfusion Controller, Microclinical Analyzer and Microformulator for the Stackable NVU Long-term maintenance and analysis of Organ-on-Chip/Tissue-Chip devices and their interconnection present a series of engineering challenges, particularly the "volume problem" in which the signaling factors and metabolites secreted by cells are diluted below the levels of physiological effect and/or detection. In certain embodiments, the present invention meets the requirement using compact, autonomous control and sensing modules.

According to certain embodiments, the present invention has developed new classes of compact, low-cost microfluidic pumps. Specifically, the present invention provides prototype well-plate sized modules that serve as a Perfusion Controller (PC) that allows fluid delivery or sampling on a nanoliter scale; a MicroClinical Analyzer (μCA) that performs multianalyte microphysiometry (MAMP) of metabolic response; and a MicroFormulator (μF) to perform on-demand mix and delivery of nutrients, drugs/toxins, or calibrants for the μCA.

This invention supports the overall goal of creating an integrated NVU System that builds upon the RPPM and RPV, which are miniaturized by utilizing small frame motors and eliminating the stand-alone pump controller. The motor driver, microcontroller, and position sensing, wireless communication, and feedback electronics are physically placed on top of each motor's housing itself, thus creating a "smart motor" that operates each pump or valve autonomously and with on-board calibration. Materials and fabrication improvements increase flexibility and reliability of the system while reducing cost, size, and wire clutter.

Example 7

Integrated Organ Microfluidics (IOM) for NVU Control and Sensing

Long-term autonomous Organ-on-Chip (OoC) operation for drug and physiology studies, the "volume problem," and the need to optimize size, cost, and ease of NVU use suggest that acceptance of OoCs for drug development and basic biology will be accelerated by the introduction of Integrated Organ Microfluidics (IOM) modules that put PC, μCA, and μF on a single microfluidic chip. The OoC can either be on that chip or an immediately adjacent chip or in a stacked/layered bioreactor.

The various operations in creating, maintaining, and analyzing an NVU involve different fluidic operations, such as cell loading, media recirculation and replacement, injection of indicator dyes, control of salinity, and withdrawal of samples, each requiring multiple pumps and valves. In certain embodiments, a five-motor system is unwieldy, but smaller motors could be implemented. The RPVs with the smaller motors are more sophisticated than the five-motor system, and hence have the potential to reduce overall module size and fluidic topology.

EXAMPLE 8

Optimization of UPLC-IM-MS Workflows for Materials Assessment and NVU Validation Small tissue and media volumes present a significant challenges to analytical chemists charged with assessing organ-on-chip health and response to drugs and toxins. IM-MS is a sensitive analytical technique that has shown great potential as a detection tool for cellular processes, chromatography, and composition analysis, particularly for small volumes.

In certain embodiments, microbioreactor effluent was analyzed by UPLC-IM-MS, while new informatics tools have been developed.

In certain embodiments, IM-MS was used to examine the effluent from all NVU and transwell chambers and a metabolic profile of the NVU and its response to drugs and toxins was developed. Furthermore, as described above, UPLC-IM-MS was used to analyze the effects of bioreactor materials, including COC, on overall device performance by assessing drug and/or toxin interactions with the NVU, RPPM, and RPV surfaces.

EXAMPLE 9

Longitudinal Assessment of Neuronal Health and Function within the NVU-IOM System The reciprocal interactions that occur across the BBB between the vascular and neuron/astrocyte compartments in the CNS ensure the appropriate uptake of nutrients and removal of waste products, while also providing a barrier to the distribution of chemical, pharmaceutical, and infectious agents. A successful NVU needs to model these characteristics and ensure neuronal health. In this example, the ability of the NVU BBB of the present invention to maintain neuronal health and function by a longitudinal study of basic neuronal attributes in the context of optimized nutrient/waste exchange across the BBB (nutrient enriched blood/serum on the vascular side and non-nutrient artificial cerebral spinal fluid (ACSF) on the brain side) was assessed. This example ensures continued neuronal health and function by confirming the maintenance or improvement of the validated functional qualities of the cortical neuron/glial network defined above in Example 2.

The neurons used in the present invention were described in the above Example 2 and Example 3. In this example, the alternative strategy of evaluating whether compromised neuronal health is being driven by energetics or metabolism (e.g., failure of appropriate nutrient delivery across the BBB) can be examined by measuring the relative glucose consumption, lactate production, and acidification rate of the neurons and other cells in the NVU BBB. The mitochondrial membrane potential of neurons can be used as a sensitive marker of cellular stress. This direct measurement of mitochondrial function can be measured by high-content imaging of neurons/astrocytes stained with MitoID (Enzo Life Sciences Kit #51019-KP002), a dye that is taken up by mitochondria in a mitochondria membrane potential sensitive way.

In this example, four outcome measures of neuronal health and function can be assessed: (A) cellular viability; (B) continued or enhanced expression of neuronal and glial lineage markers and cellular morphologies (e.g., FOXG1, TBR2, GFAP, etc.) by QRT-PCR and immunohistochemical and cellular morphological analysis; (C) maintenance of neuronal synaptic structures assessed by immunohistochemistry of pre- and post-synaptic markers (e.g., Homer1 and synapsin 1); (D) spontaneous and evoked electrophysiological network activity. Further, these same functional neuronal attributes can be analyzed in the context of other NVU validation approaches under the following Examples 9-11 (e.g., following metabolic, chemical, or viral challenge). Neuronal/glial health and function can be assessed longitudinally at days 1, 7, and 28 in the NVU-IOM system and neuronal/astrocyte networks cultured in the absence of the NVU-IOM system in traditional neuronal maintenance medium. Functional validation over the longitudinal study (outcome measures B, C, and D, above) can be performed as described under Example 2 for the characterization of the neuronal/glial cells placed into the NVU-IOM system. Numerous neuronal/astrocyte viability (outcome measure A above) assays are routinely performed and would be used here by a combination of assays to either quantify live cells (e.g., the fixable "Live-or-Dye" stain (Biotium; #32004)) that allows separate quantification of living neurons and astrocytes, or by determining degree of cell death (e.g., by LDH release or uptake of propidium iodide, measures of plasma membrane integrity, or TUNEL staining, a measure of apoptosis, Promega #G3250)).

As a result, the outcome measures of neuronal-glial network health and function were as good as or improved compared to standard culture conditions. Furthermore, metabolic, chemical, and viral challenge to neuronal health were relatively protected behind the BBB curtain of the NVU-IOM versus in standard culture conditions.

EXAMPLE 10

Validate the NVU for Studies of Nutrient Gradient Across the BBB and a Nutrient Deprivation Model of Neuronal Stress In this example, the microfluidic, in vitro NVUs of the present invention is used to study disease models. To accomplish this purpose, the NVU tissue chambers of the present invention were used to validate the model of nutrient gradients and deprivations across the BBB. This model was validated against expected performance of a real BBB in studies of nutrient deprivation, including transient ischemic attacks (TIA). The three-dimensional microphysiological tissue system 1) recapitulates the multicellular architecture and functional representation of the interfaces between the blood, CNS, and CSF, 2) provides spatiotemporal microenvironmental control enabled by real-time metabolic bioenergetic and optical monitoring, 3) enables near-real-time metabolomic and proteomic analysis of system effluent in support of ADMET and safety screening, 4) reproducibly and viably operates under physiological conditions for at least four weeks, 5) represents both normal and diseased phenotypes by allowing flexible combinations of cells from different genetic pools derived from either humans or lower vertebrates, and 6) allows high-content screening (HCS) using custom-fabricated, microfluidic devices operated in a ThermoFisher ArrayScan microscope system.

In certain embodiments, a realistic microphysiological model of blood/brain/CSF interactions and responses to drugs and toxins was created by combining the technologies of: microfluidic devices and protocols of the present invention enable acute and long-term cell studies, advanced microscopy, cellular control and modeling of metabolic systems, and organs-on-chips. Microfabrication and co-culture bioreactors are being used to study angiogenesis. Specific ion mobility mass spectrometers and pioneering electrochemical measurements of cellular bioenergetics provide novel assays of cellular toxicity, drug response, signaling and metabolism, for simultaneous evaluation of primary and secondary effects of drugs, toxins, pathogens, particulates and other agents on the brain and to facilitate the assessment of biomarkers, bioavailability, efficacy, and toxicity of therapeutic agents prior to entry into clinical trials."

In certain embodiments, multianalyte microphysiometers (MAMP), implemented as the MicroClinical Analyzer (µCA), provides real-time simultaneous detection of key metabolites in a microfluidic chamber, including extracellular glucose, oxygen, lactate, and pH. The MAMP has provided new insights into immediate metabolic effects of protein toxins, the metabolism of cancer cells, responses of murine islets to nutrient stimulation, and oxidative bursts in macrophages. The metabolic compensation and survival of nutrient-deprived neurons relies on neuronal-glial chemical and physical communication. Metabolic adaptation is a critical, but poorly understood, determinant of cell fate. In one example, a MAMP work revealed a strong correlation between metabolic recovery and neuronal survival. Additionally, some MAMP studies observed rapid metabolic changes in neurons and glia suffering from extended nutrient deprivation in vitro and provided the first dynamic measures that identified some of the essential events mediating injury. This also increases the understanding of the steps required to develop predictive biomarkers of injury, an objective not yet possible in clinical settings. Microphysiometry has revealed that the greatest single predictor of neuronal survival was extracellular acidification; however, lactate levels, currently a key clinical indicator of injury, were not correlated with neuronal cell fate. More important, the MAMP allowed direct comparison of the real-time metabolic response of primary pure neurons and mixed cultures exposed to 90 min of glucose deprivation (GD). These studies demonstrates that the NVU-IOM system, for which the MAMP/μCA is an integral component, and is capable of detecting bioenergetic changes in cells from each compartment of the NVU model.

In this example, the events of acute aglycemia and hypoxia associated with embolic stroke were recapitulated to determine the capability of the NVU/IOM system to track rapid changes in cell metabolism associated with exposure to high glutamate and/or acidification as would occur in an ischemic stroke. As a result, the new NVU/IOM recapitulated the natural nutrient gradients across the BBB and the rapid changes in response to OGD. In certain embodiments, the increased physical proximity of the neurons, glia, and endothelial cell layers increased the response to stress because the NVU/IOM environment better represents in vivo conditions, where OGD is a more potent means to induce neuronal cell death.

EXAMPLE 11

Pharmacological NVU Validation

Drug companies cannot predict the active transport of small molecule therapeutics across the BBB. Given the importance of tightly regulated drug exposure in the often delicate balance between efficacy and toxicity, this represents a significant challenge for the pharmaceutical industry. Unfortunately, rodent models of BBB permeability often show large differences in the expression of key transporters that govern drug import and export, making preclinical models unreliable for accurate assessment of CNS exposure. We have demonstrated the ability of some agents and drugs to reduce BBB permeability, and others to increase it. Specific experiments are summarized as follows.

FITC-Dextran Diffusion Across the BBB. Solutions of 10 KDa or 70 KDa FITC-labeled dextran (Sigma-Aldrich, St. Louis, Mo., USA) were prepared at 1 μm/mL (100 nM for 10 KDa and 700 nM for 70 KDa) in cell culture media. Then the vascular compartment of the NVU was perfused with either 70 or 10 KDa solution for 23 hours. At the 23-hour mark, the flows through both the vascular and brain compartments were stopped for 1 hour, allowing the dextran to diffuse across the BBB and accumulate in the brain compartment. After a 1-hour pause, perfusion of both chambers was restarted and individual effluents were collected for fluorescent intensity analysis using a plate reader (TECAN M1000). By measuring FITC-dextran diffusion across the membrane, we are able to evaluate the effectiveness of our BBB.

FITC-dextran diffusion tests showed that our NVU BBB significantly blocked both 70 kD and 10 kD FITC-dextran from diffusing from the vascular chamber into the brain chamber (p=0.01). We also showed that disruption of the BBB by exposing it to 1 mM glutamate, which is known to considerably disrupt tight junctions, does indeed significantly increase diffusion of FITC-dextran across the BBB (FIG. 5A-C). While both are significant effects, the first compares the cellular barrier only to the mechanical properties of the device, while the second is a biologically relevant disruption (but does not destroy the BBB such that the graphs in FIG. 2 have differing scales). In combination, these experiments demonstrate the generation of a functional cellular barrier within our NVU.

Ascorbate Transport Across the BBB. Twenty-four hours before testing, the NVUs were switched into media containing no vitamin C. At time 0, 100 μM ascorbate was added to the vascular media, and samples were collected for both FITC-dextran analysis and ascorbate transport every 15 min for 1 hour. Perfusate samples for ascorbate (20 μL) were treated with 20 μL of 25% metaphosphoric acid, mixed by vortexing, and treated with 80 μL of 0.1M Na2HPO4 containing 0.05 mM EDTA, pH 8.0. After vortexing briefly, the samples were centrifuged at 4° C. for 1 min at 13,000×g. The supernatant was taken for assay of ascorbate by high performance liquid chromatography.

Ascorbate, which is known both to tighten the BBB and be actively transported across the barrier, can be used as an indication of active transport. In looking at ascorbate concentration over time, we saw a significant increase in all four NVUs tested (p=0.01). In contrast, FITC-dextran diffusion across the barrier was significantly reduced (p=0.0012) by the addition of ascorbate, and then remained steady over time. Since diffusion cannot account for the increase in ascorbate on the brain side, this is an indication of active transport.

Cold Shock and Glutamate Exposure. We used cold shock and exposure to glutamate to evaluate the quality of the BBB established within the NVU and its physiological responses to chemical and environmental perturbations. For glutamate exposure, NVUs were first maintained under normal culture conditions for 14 days to develop a mature BBB, then the media perfusing the vascular compartment was switched to one containing 1 mM of glutamate (Sigma-Aldrich, St. Louis, Mo., USA) and flowed through the reactor for 1 hour. At the end of a 1-hour exposure to glutamate, the state of the BBB was evaluated using FITC-dextran as described above. For cold shock exposure, the NVUs were cultured normally for 18 days and then were placed for 12 hours at 33° C. The disruption of the BBB was evaluated as changes in transendothelial electrical resistance (TEER) measured between the vascular compartment and the brain layer. We concluded that both cold shock and brain glutamate will weaken the BBB.

TEER Measurements in the NVU. Transendothelial electrical resistance (TEER) measurements were performed using our custom-built impedance analyzer based on an AD5933 chip (Analog Devices, Nashua, N.H., USA) and utilizing a four-probe approach. Electrical connections to the NVU chambers were created by incorporating 5-mm long sections of 23 ga stainless steel tubing into the media-supply Tygon tubing 2.5 cm away from the NVU inlets. While it might still suffer from the cable properties outlined in the literature, these measures did change as the biology of the cells changed, indicating its biological relevance. The current source probes were connected between the inlet of the brain layer and the vascular chamber outlet, ensuring that the excitation current flowed across the brain compartment and through the endothelial layer. The sensing voltage probes were connected between the vascular chamber inlet and the brain layer outlet. Unlike commercially available TEER instruments, such as the WPI EVOM2, where impedance measurements are performed at a single frequency of 12.5 Hz, we have the ability to monitor impedance as a function of probe frequency between 3 and 100 KHz, allowing us to determine the range of frequencies with the highest sensitivity to cell-to-cell junction formation. Impedance measurements were taken once a week with the full range frequency sweep. Changes of impedance at 15 kHz showed the largest change as a function of BBB maturation.

There is a significant increase in TEER around Day 12 of approximately 30% (p=0.05). The percent increase is typical of reports for TEER and tight junctions, although our values are higher, as the NVU itself has a high natural impedance. This correlates well with the histology verifying tight junction formation. In addition to detecting tight junction formation, TEER was also useful for evaluating cell viability. In devices in which perfusion was occluded by 50% at Day 14 in culture, TEER showed a large drop at Day 21, which was later shown to correlate with cell survival. When tight junctions (but not cell survival) were impaired via cold shock of 33° C. for 12 hours, TEER decreased significantly (p=0.001) (FIG. 7C). Furthermore, these measures of impedance show that the NVU device acts as a capacitor, with its peak impedance between 15-20 kHz, and that we can use the shape of this capacitance to monitor the health of our devices over time. These findings demonstrate not only the reliability of our custom TEER device in our NVU, but also show that our BBB is functioning as expected with regard to its endothelial cell resistance.

Response of the BBB to Inflammatory Cytokines. We utilized new advances in microfluidics, organs-on-chips, and metabolomics to examine the complex relationship of inflammation and its effects on blood-brain barrier function ex vivo and the metabolic consequences of these responses and repair mechanisms. In this study we paired our novel dual-chamber, organ-on-chip microfluidic NVU with small-volume cytokine detection and mass spectrometry analysis to investigate how the blood-brain barrier responds to two different but overlapping drivers of neuroinflammation, lipopolysaccharide and a cytokine cocktail of IL-1β, TNF-α, and MCP1,2. In this study we showed that 1) during initial exposure to lipopolysaccharide, the blood-brain barrier is compromised as expected, with increased diffusion and reduced presence of tight junctions, but that over time the barrier is capable of at least partial recovery; 2) a cytokine cocktail also contributes to a loss of barrier function; 3) from this time-dependent cytokine activation, metabolic signature profiles can be obtained for both the brain and vascular sides of the blood-brain barrier model; and 4) collectively, we can use metabolite analysis to identify critical pathways in inflammatory response. Taken together, these findings present new data that allow us to study the initial effects of inflammatory stimulation on blood-brain barrier disruption, cytokine activation, and metabolic pathway changes that drive the response and recovery of the barrier during continued inflammatory exposure.

The foregoing description of the exemplary embodiments of the present invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. A planar layered device, comprising:
a top planar layer; and
a bottom planar layer stacked together,
wherein the top planar layer comprises a top base having an upper surface and a lower surface, a top cover covering the upper surface of the top base, and a top membrane attached to the lower surface of the top base, the top base has a top through hole formed therein, the top through hole is sealed by the top cover and the top membrane to form a top chamber, and the top chamber is in fluid communication with a first input channel and a first output channel located in the top base;
wherein the bottom planar layer comprises a bottom base having an upper surface and a lower surface, and a bottom substrate attached to the lower surface of the bottom base, the bottom base has a bottom through hole formed therein, the bottom through hole is sealed by the top membrane and the bottom substrate to form a bottom chamber, and the bottom chamber is in fluid communication with a second input channel and a second output channel located in the bottom base; and
wherein the top chamber and the bottom chamber correspond to each other and are separated by the top membrane.

2. The planar layered device of claim 1, further comprising at least one middle planar layer disposed between the top planar layer and the bottom planar layer, wherein the at least one middle planner layer comprises a middle base having an upper surface and a lower surface, the top membrane is disposed between the lower surface of the top base and the upper surface of the middle base, a middle membrane is disposed between the lower surface of the middle base and the upper surface of the bottom base, the middle base has a middle through hole formed therein, the middle through hole is sealed by the top membrane and the middle membrane to form a middle chamber, and the middle chamber is in fluid communication with a third input channel and a third output channel located in the middle base.

3. The planar layered device of claim 2, wherein the first input channel and the first output channel are recessed from the lower surface of the top base, the second input channel and the second output channel are recessed from the lower surface of the bottom base, and the third input channel and the third output channel are recessed from the lower surface of the middle base.

4. The planar layered device of claim 2, wherein the at least one middle planar layer comprises a plurality of middle planar layers.

5. The planar layered device of claim 2, wherein a thickness of the top membrane and the middle membrane is in a range of about 5-20 μm, a height of the top chamber, the middle chamber and the bottom chamber is in a range of about 50-150 μm.

6. The planar layered device of claim 2, wherein the top chamber, the middle chamber and the bottom chamber are aligned sequentially with each other, the top membrane is porous or a portion of the top membrane corresponding to the top chamber and the middle chamber is porous, and the middle membrane is porous or a portion of the middle membrane corresponding to the middle chamber and the bottom chamber is porous.

7. The planar layered device of claim 2, wherein each of the top planar layer, the middle planar layer and the bottom planar layer further comprises sidewalls surrounding the top base, the middle base or the bottom base.

8. The planar layered device of claim 1, further comprising a top cell layer disposed between a bottom surface of the top chamber and the top membrane, and a bottom cell layer disposed between the top membrane and an upper surface of the bottom chamber.

9. The planar layered device of claim 8, wherein the top cell layer comprises brain astrocytes and pericytes, and the bottom cell layer comprises brain microvascular cells.

10. The planar layered device of claim 1, wherein the top cover and the bottom substrate are made of glass.

* * * * *